(12) United States Patent
Nguyen et al.

(10) Patent No.: US 11,701,130 B2
(45) Date of Patent: Jul. 18, 2023

(54) ARTHROPLASTY BALANCE AND GAP GAUGE AND CUTTING GUIDANCE

(71) Applicant: Optimotion Implants LLC, Orlando, FL (US)

(72) Inventors: Vuong Binh Nguyen, Windermere, FL (US); Dinesh V. Koka, Winter Springs, FL (US)

(73) Assignee: OPTIMOTION IMPLANTS LLC, Orlando, FL (US)

( * ) Notice: Subject to any disclaimer, the term of this patent is extended or adjusted under 35 U.S.C. 154(b) by 31 days.

(21) Appl. No.: 17/345,271

(22) Filed: Jun. 11, 2021

(65) Prior Publication Data

US 2022/0395281 A1 Dec. 15, 2022

(51) Int. Cl.
*A61B 17/15* (2006.01)
*A61B 17/88* (2006.01)

(52) U.S. Cl.
CPC .......... *A61B 17/155* (2013.01); *A61B 17/157* (2013.01); *A61B 17/8897* (2013.01)

(58) Field of Classification Search
CPC combination set(s) only.
See application file for complete search history.

(56) References Cited

U.S. PATENT DOCUMENTS

| | | | |
|---|---|---|---|
| 4,567,886 A | 2/1986 | Petersen | |
| 6,478,799 B1 | 11/2002 | Williamson | |
| 7,569,060 B2 | 8/2009 | Faoro | |
| 7,641,663 B2 | 1/2010 | Hodorek | |
| 8,137,361 B2 | 3/2012 | Duggineni et al. | |
| 8,162,949 B2 | 4/2012 | Duggineni et al. | |
| 8,454,616 B2 | 6/2013 | Hodorek et al. | |
| 2004/0249386 A1 | 12/2004 | Faoro | |
| 2007/0173848 A1 | 7/2007 | Lennox et al. | |
| 2008/0312659 A1 | 12/2008 | Metzger et al. | |

(Continued)

FOREIGN PATENT DOCUMENTS

GB 2516674 A 2/2015

OTHER PUBLICATIONS

Mihalko et al., "Soft-Tissue Balancing During Total Knee Arthroplasty in the Varus Knee",*Journal of American Academy of Orthopaedic Surgeons*, Dec. 2009 p. 766-774 http://upload.orthobullets.com/journalclub/free_pdf/19948701_19948701.pdf.

(Continued)

*Primary Examiner* — Sameh R Boles
(74) *Attorney, Agent, or Firm* — David Meibos; Maywood IP Law

(57) ABSTRACT

A gap gauge is disclosed for facilitating an arthroplasty procedure on a first bone and a second bone of a patient. The gap gauge may include a first plate positionable in contact with the first bone, a second plate positionable in contact with the second bone. The second plate may be displaced from the first plate by a displacement. The gap gauge may further include a balance indicator configured to indicate a balance status between the first plate and the second plate and a pin guide. The pin guide is configured to couple to one of the first plate and second plate and includes a pin hole that is configured to guide a pin for insertion into the second bone. The pin can be used to couple a cutting guide to the second bone to resect the second bone to adjust the balance status.

20 Claims, 30 Drawing Sheets

(56) References Cited

U.S. PATENT DOCUMENTS

| | | |
|---|---|---|
| 2009/0264890 A1 | 10/2009 | Duggineni et al. |
| 2010/0145343 A1 | 6/2010 | Johnson et al. |
| 2012/0323246 A1 | 12/2012 | Catanzarite et al. |
| 2013/0296860 A1 | 11/2013 | Chana et al. |
| 2014/0288563 A1* | 9/2014 | Claypool ........... A61B 17/1764 606/88 |
| 2016/0074053 A1 | 3/2016 | Hutchison et al. |
| 2017/0156736 A1 | 6/2017 | Claypool et al. |
| 2020/0352556 A1 | 11/2020 | Walker |

OTHER PUBLICATIONS

Stryker Corporation, "Triathlon Knee System: Gap Balancing Technique Surgical Protocol Addendum", Orthopaedics, 2015, 10 pgs.
Abdel, et al., "Gap Balancing versus measured resection in TKA", 6 pgs., last accessed Dec. 23, 2020, https://aorecon.aofoundation.org/education/surgical-insights/124.html.
International Search Report dated Sep. 1, 2022 for PCT/US 2022/027162.

\* cited by examiner

ARTHROPLASTY BALANCE AND GAP GAUGE AND CUTTING GUIDANCE

TECHNICAL FIELD

The present disclosure relates to surgical devices. More specifically, the present disclosure relates to improved surgical instruments for arthroplasty procedures.

BACKGROUND

Arthroplasty procedures can be used to relieve pain in or restore function of a joint due to conditions such as osteoarthritis, rheumatoid arthritis, or other joint conditions through minimally invasive or invasive surgery. An arthroplasty procedure can be performed on any joint and may include a partial or total joint replacement with a replacement prosthesis or prostheses. During an arthroplasty procedure, a surgeon may want to measure a size of an opening between two bones of the joint. In addition, the surgeon may also want to measure a balance of the joint in addition to a size of an opening (referred to as a gap) between two bones of the joint. Further, a surgeon may also want to determine where and how to resect one or more of the bones of the joint in order to adjust for a measured balance status (e.g., imbalance or balance) between two bones of the joint. For example, during partial or total knee replacement (TKR) arthroplasty, a surgeon may desire to gauge or measure a displacement between two bones of the joint and a balance of the joint and make a resection that counters a measured balance status. Taking such measurements during minimally invasive or invasive arthroplasty can be a challenge given forces applied to the joint by ligaments and other soft tissue of or around the joint. Accordingly, a need exists for improved systems and methods to measure the gap and/or angulation between bones and guide a surgeon in making any further resection of the bones in the course of an arthroplasty procedure.

SUMMARY

The various apparatus, devices, systems, and/or methods of the present disclosure have been developed in response to the present state of the art, and in particular, in response to the problems and needs in the art that have not yet been fully solved by currently available arthroplasty balance gauges, arthroplasty gap gauges, or cutting guides. The apparatus, devices, systems, and/or methods of the present disclosure may provide arthroplasty balance, gap gauge, and cutting guide adjustment in a single device that remedy shortcomings of prior art separate arthroplasty balance gauges, arthroplasty gap gauges and/or cutting guides.

To achieve the foregoing, and in accordance with the disclosure as embodied and broadly described herein, a gap gauge for facilitating an arthroplasty procedure on a first bone and a second bone of a patient may be provided. One general aspect of the gap gauge can include a first plate positionable in contact with the first bone. The gap gauge also includes a second plate positionable in contact with the second bone, where the second plate is displaced from the first plate by a displacement. The gap gauge also includes a balance indicator configured to indicate a balance status between the first plate and the second plate. The gap gauge also includes a pin guide configured to couple to one of the second plate and the first plate, the pin guide may include a first pin hole configured to guide insertion of a first pin into the second bone.

In one aspect, the pin guide may include an attachment feature configured to removably couple the pin guide to the second plate such that the pin guide guides insertion of the first pin into the second bone according to the balance status between the first plate and the second plate. The pin guide further may include an attachment feature configured to removably couple the pin guide to the second plate such that the pin guide guides insertion of the first pin into the first bone according to the balance status between the first plate and the second plate.

In another aspect, the pin guide may include a second pin hole configured to guide insertion of a second pin into the second bone. In one aspect, the pin guide couples to the first plate and extends from the first plate such that the pin guide guides insertion of the first pin and the second pin into the second bone such that the first pin and the second pin align at an angle relative to the second plate that counters the balance status between the first plate and the second plate.

In one aspect, the first pin hole guides insertion of the first pin into one of a medial condyle and a lateral condyle of the second bone and the pin guide may include a second pin hole configured to guide insertion of a second pin into the other one of the medial condyle and the lateral condyle of the second bone.

In another aspect, the pin guide may include: a second pin hole configured to guide insertion of a second pin parallel to the first pin into the second bone and an adjustment feature configured to rotate the first pin hole and the second pin hole together to counter different angular offsets of the balance status.

In one aspect, the pin guide may include: a base configured to connect to the second plate; an arm that may include the first pin hole; and a mast extending from the base, the mast connecting the arm and the base. The arm may include a second pin hole, the first pin hole and the second pin hole each positioned in the arm on one of a medial side and a lateral side of a knee when the gap gauge is in place relative to the knee.

In another aspect, the pin guide may include a second pin hole configured to guide insertion of a second pin into the second bone such that the first pin and the second pin align with each other at an orientation relative to the second plate that matches the balance status; and where coupling a cutting guide to the second bone by way of the first pin and the second pin communicates the balance status to the cutting guide.

In one aspect, a cutting guide may include an alignment feature that may include a plurality of sets of holes, each member (each set) of the sets of holes configured to accept one of the first pin and the second pin. Each set of holes may be configured to adjust for a different angular offset for the balance status.

In another aspect, the cutting guide may include: a guide feature configured to guide motion of a cutter to resect a bone; an alignment feature configured to accept the first pin and the second pin and position the cutting guide on the bone; and an adjustment feature configured to rotate the guide feature relative to the alignment feature to adjust for different angular offsets from the balance status.

In one aspect, the first plate and the second plate are sized for insertion between the first bone that may include a tibia and the second bone that may include a femur.

One general aspect can include a gap measurement and correction assembly for facilitating an arthroplasty procedure on a femur and a tibia of a patient. The gap measurement and correction assembly also includes a gap gauge that may include: a superior plate extending from a superior body; an inferior plate extending from an inferior body, where the superior plate is displaced from the inferior plate by a displacement; a separator connected to the superior body and the inferior body to adjust the displacement; a balance indicator connected to one of the superior plate and the inferior plate and configured to indicate a nonparallel orientation of the superior plate relative to the inferior plate; and a pin guide configured to guide insertion of a first pin into one of the tibia and the femur of the patient. The gap measurement and correction assembly also includes a cutting guide attachable to one of the tibia and the femur via the first pin, where the cutting guide is configured to guide resection of the one of the tibia or the femur that counters the nonparallel orientation.

In one aspect, the assembly where the pin guide further may include an attachment feature configured to removably couple the pin guide to the superior plate such that the pin guide guides insertion of the first pin into the femur according to the nonparallel orientation of the superior plate relative to the inferior plate. The pin guide further may include an attachment feature configured to removably couple the pin guide to the superior plate such that the pin guide guides insertion of the first pin into the tibia according to the nonparallel orientation of the superior plate relative to the inferior plate.

In another aspect, the pin guide is further configured to guide a second pin into the other one of the tibia and the femur of the patient; and where the pin guide further may include an attachment feature configured to removably couple the pin guide to the inferior plate such that the pin guide guides insertion of the first pin and the second pin into the femur such that the first pin and the second pin align at an angle relative to the superior plate that counters the nonparallel orientation of the superior plate relative to the inferior plate.

In one aspect, the pin guide may include: a base configured to connect to the superior plate; an arm may include a first pin hole; and a mast extending from the base, the mast connecting the arm and the base. The cutting guide may include an alignment feature that may include a plurality of sets of holes each member of the sets of holes configured to accept one of the first pin and a second pin, each set of holes configured to adjust for a different angular offset for the nonparallel orientation.

In another aspect, the cutting guide may include: a guide feature configured to guide motion of a cutter to resect a bone; an alignment feature configured to accept the first pin and a second pin and position the cutting guide on the bone; and an adjustment feature configured to rotate the guide feature relative to the alignment feature to adjust for different angular offsets from the nonparallel orientation.

One general aspect can include a method for measuring and correcting imbalance for an arthroplasty procedure on a femur and a tibia of a patient. The method includes inserting a first plate and a second plate of a gap gauge between the femur and the tibia of a knee joint of a patient. The method also includes actuating the first plate and the second plate apart such that the first plate is in contact with a resected surface of the femur and the second plate is in contact with a resected surface of the tibia. The method also includes reading a balance indicator of the gap gauge to obtain a balance status between the femur and the tibia, inserting a first pin through a pin guide of the gap gauge, securing the first pin to one of the femur and the tibia, and coupling a cutting guide to the one of the femur and the tibia using the first pin. The method also includes using the cutting guide to guide resection of one of the femur and the tibia to counter a nonparallel orientation of the first plate relative to the second plate.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

Figure 1A:
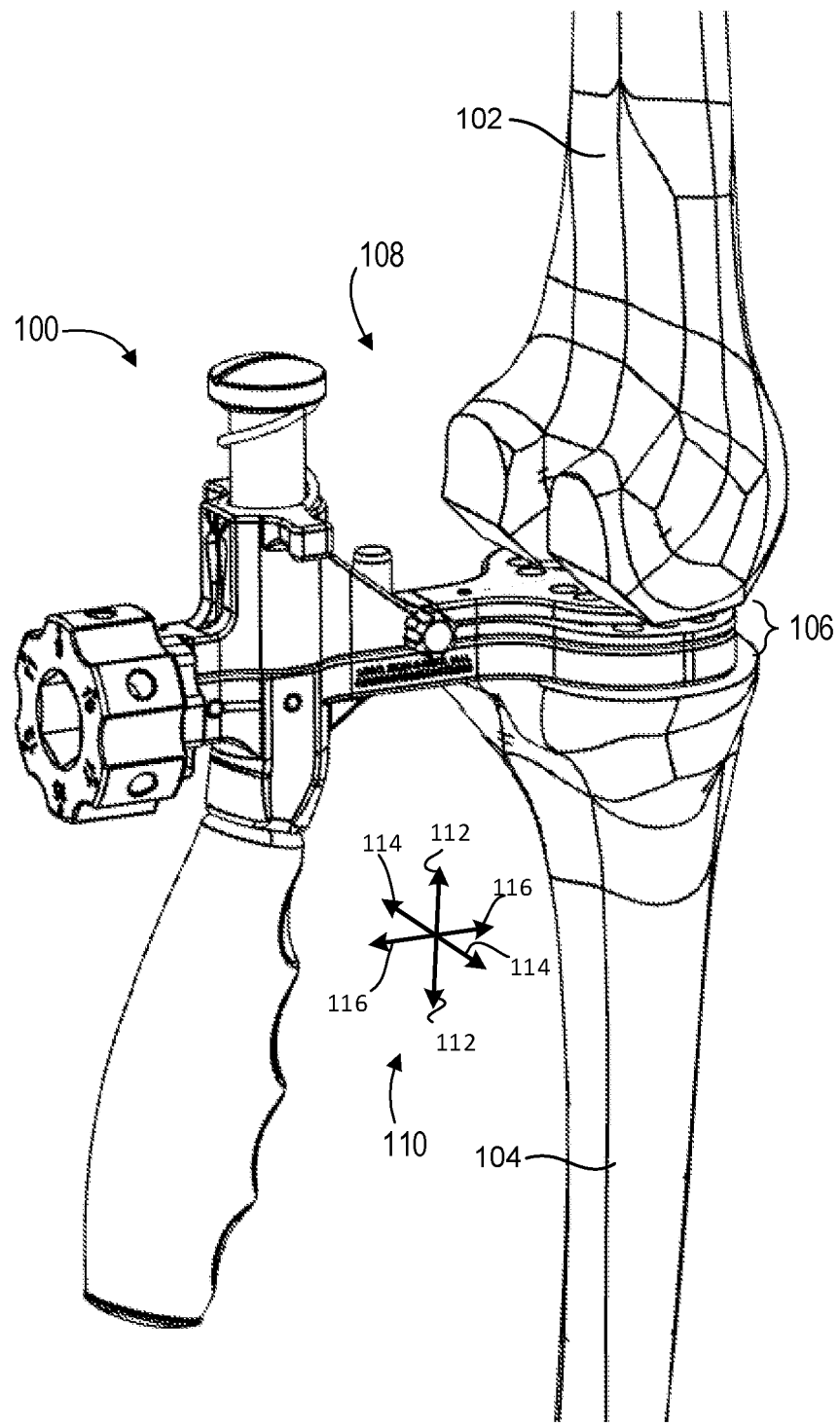
FIG. 1A is a perspective view of a gap gauge, according to one embodiment of the present disclosure.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application, but is merely representative of exemplary embodiments of the present disclosure.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions.

An anterior-posterior axis is an axis perpendicular to the coronal plane. A medial-lateral axis is an axis perpendicular to the median plane. A cephalad-caudal axis is an axis perpendicular to the transverse plane. These descriptive terms may be applied to an animate or inanimate body.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The present disclosure discloses a gap gauge for facilitating an arthroplasty procedure on a first bone and a second bone of a patient. During an arthroplasty procedure, a surgeon may need to confirm that the gap between two bones of the joint is of a desired displacement and that the joint has a desired balance (e.g. balanced, varus condition, or valgus condition). Using separate instruments to get either the displacement or the balance status can complicate the procedure and may require more personnel to assist in the procedure. As one instrument is exchanged for another (e.g., an instrument that only measures displacement exchanged for an instrument that only measures balance status), parts of a joint can shift and thus alter a displacement already measured or alter a balance status read using an instrument that cannot provide both displacement measurements and a balance status, or balance measurement in a single instrument. Consequently, a need exists for an improved gap gauge. In particular, a need exists for gap gauge that can provide both a displacement measurement and a balance status (e.g., balance measurement) using a single instrument. Furthermore, the present disclosure provides for a gap gauge that enables a user to optionally disengage/disable a balance indicator or balance gauge 168 during use for that a user can use the same instrument to only measure displacement between two joint bones, if desired.

FIG. 1A is a perspective view depicting one exemplary embodiment of a gap gauge 100 for facilitating an arthroplasty procedure on a first bone and a second bone of a patient. As used herein, an "arthroplasty procedure" refers to a surgical procedure for restoring and/or improving function and/or operation of a joint of a patient. An arthroplasty procedure can be done for a toe joint, ankle joint, knee joint, hip joint, arm joint, elbow joint, finger joint, or the like. In the illustrated embodiment, the first bone can be a femur 102 and the second bone can be a tibia 104. As used herein, a "gap gauge" refers to an apparatus, instrument, structure, device, component, system, assembly, hardware, software, firmware, circuit, module, or logic structured, organized, configured, programmed, designed, arranged, or engineered to measure an attribute, characteristic, state, or condition of another structure or object or set of structures or objects. In one embodiment, the gap gauge is structured, organized, configured, programmed, designed, arranged, or engineered to measure a displacement between two structures.

As part of an arthroplasty procedure, the gap gauge 100 can be inserted into an opening 106, also referred to as a gap, between the first bone and the second bone. The gap gauge 100 can be used to determine how much displacement exists between the first bone and the second bone within the opening 106. As used herein, an "opening" refers to a gap, a hole, an aperture, a void in a structure, or the like. In certain embodiments, an opening can refer to a structure configured specifically for receiving something and/or for allowing access. The amount of displacement can be referred to herein as measuring a gap, or space, between the first bone and second bone.

In addition, or alternatively, the gap gauge 100 can be used to determine a balance status of a joint 108 that is part of the arthroplasty procedure. The joint 108 can be a toe joint, ankle joint, knee joint, hip joint, arm joint, elbow joint, finger joint, or the like. In the illustrated embodiment, the joint 108 is a knee joint and the first bone is a femur 102 and the second bone is a tibia 104. Gap gauge 100 can be used to determine both displacement within the opening 106 and a balance status using a single device. Alternatively, a user, such as a surgeon, can use the gap gauge 100 to determine displacement or a balance status using a single convenient device with the first bone and second bone in flexion, in extension, or at an angle between flexion and extension.

FIG. 1A illustrates a three-dimensional axis 110. The three-dimensional axis 110 includes a cephalad-caudal axis 112, a medial-lateral axis 114, and an anterior-posterior axis 116. The three-dimensional axis 110 is used to identify how a gap gauge 100 is positioned and/or oriented with respect to an anterior-posterior axis 116 of a patient who is in a reference anatomical position.

Figure 1B:
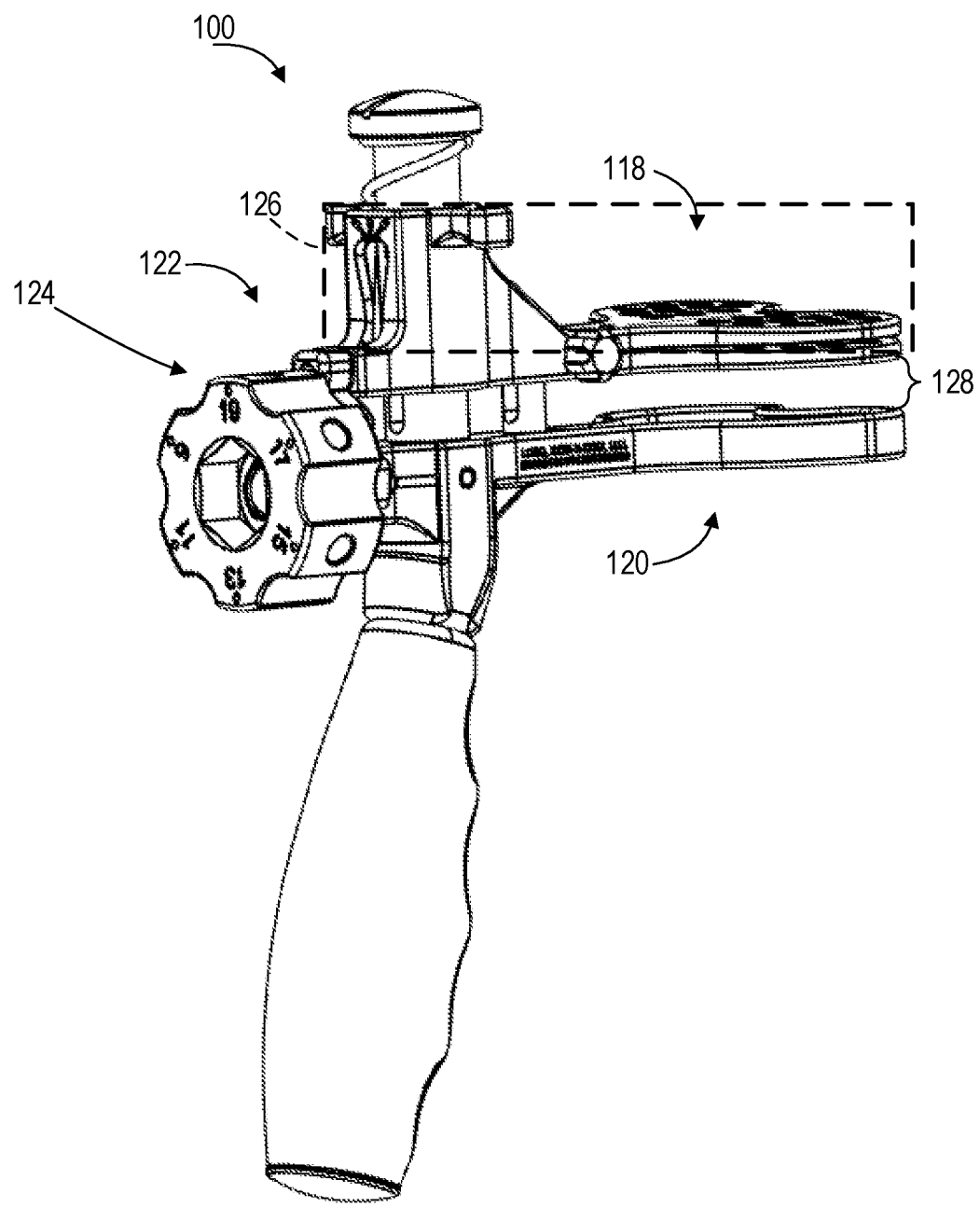
FIG. 1B is a perspective view of the gap gauge of FIG. 1A.

FIG. 1B is a perspective view of the gap gauge 100 of FIG. 1A. FIG. 1B illustrates the gap gauge 100 without a first bone or second bone shown. The gap gauge 100 may generally include a first plate, a second plate, a separator, a separation indicator, and a balance indicator. In the illustrated embodiment, the first plate may be an inferior plate 120 and the second plate may be a superior plate 118. The illustrated gap gauge 100 also includes a separator 122, a separation indicator 124, and a balance indicator 126.

In one embodiment, the superior plate 118 is a plate. As used herein, a "plate" refers to a flat structure or a generally flat structure. In certain embodiments, a plate can be configured to support a load. In certain embodiments, a plate may comprise a generally planar structure. A plate can be a separate structure connected to, or integrated with, another structure. Alternatively, a plate can be connected to part of another structure. A plate can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. A plate can be made from a variety of materials including, metal, plastic, ceramic, wood, fiberglass, or the like. The inferior plate 120 can also be a plate.

The superior plate 118 can be positioned opposite the inferior plate 120. The superior plate 118 can be positioned in contact with a first bone (e.g., a femur 102). The inferior plate 120 can be positioned in contact with a second bone (e.g., a tibia 104). The superior plate 118 and inferior plate 120 can be parallel to each other and cooperate to slide into an opening or gap.

In one embodiment, the superior plate 118 and inferior plate 120 have a structural integrity that permits them to be positioned, (e.g., inserted) between a femur 102 and a tibia 104. When initially positioned between two bones, the superior plate 118 and inferior plate 120 may contact each other as illustrated in FIG. 1A. Once positioned between two bones, a user may move the superior plate 118 relative to the inferior plate 120 which adjusts a displacement 128 between the superior plate 118 and the inferior plate 120. When the superior plate 118 and inferior plate 120 contact each other, the displacement 128 may be zero. In one embodiment, the superior plate 118 and inferior plate 120 may be displaced from each other by a displacement 128 when the gap gauge 100 is initially manufactured/assembled.

As used herein, a "displacement" refers to a vector that measures how much a structure, member, object, component, or part has moved, changed position, from a starting position to an ending position, or measures the distance between two objects. Displacement can be measured using a variety of units of measure including imperial units, metric units, angular units and the like. In certain embodiments, the displacement is measured in millimeters. In one embodiment, the displacement 128 may range from zero to twenty-five or more millimeters.

A user may adjust the displacement 128. A user may separate the superior plate 118 and the inferior plate 120 by manually pulling them apart and/or the user may use the separator 122 to separate the superior plate 118 and the inferior plate 120. A user may bring the superior plate 118 and the inferior plate 120 together by manually positioning them and/or the user may use the separator 122 to bring the superior plate 118 and the inferior plate 120 together.

The separator 122 connects to the superior plate 118 and to the inferior plate 120. The separator 122 can adjust the displacement 128. In one embodiment, actuation of the separator 122 adjusts the displacement 128. As used herein, a "separator" refers to an apparatus, instrument, structure, device, component, system, assembly, or module structured, organized, configured, programmed, designed, arranged, or engineered to separate a first structure from another structure. In one embodiment, the separator is structured, organized, configured, programmed, designed, arranged, or engineered to separate a first plate from a second plate and thereby create a distance between the first plate and the second plate. The separator 122 can actively adjust the displacement 128 and/or retain the superior plate 118 and inferior plate 120 in a certain state of separation, thereby maintaining a desired displacement 128.

The separation indicator 124 indicates the displacement 128 between the superior plate 118 and the inferior plate 120. The separation indicator 124 can be coupled to the separator 122. As used herein, a "separation indicator" refers to an apparatus, device, component, system, assembly, hardware, software, firmware, circuit, module, or logic structured, organized, configured, programmed, designed, arranged, or engineered to indicate a displacement between two or more structures to a user. The separation indicator can include one or more of an audible signal, a tactile signal, a visual signal or indication, and the like. In one embodiment, a visual indicator for the separation indicator may comprise a number or set of numbers that represent a unit of measure for the displacement (or distance) between the two or more structures. Alternatively, or in addition, the separation indicator may comprise a mechanical device, an electromechanical device, an electronic device (analog or digital), and the like.

The balance indicator 126 indicates a balance status. As used herein, a "balance indicator" refers to an apparatus, device, component, system, assembly, mechanism, hardware, software, firmware, circuit, module, or logic structured, organized, configured, programmed, designed, arranged, or engineered to indicate a balance status to a user of a device or apparatus that includes the balance indicator. The balance indicator can include one or more of an audible signal, a tactile signal, a visual signal or indication, and the like. Alternatively, or in addition, the balance indicator may comprise a mechanical device, an electromechanical device, an electronic device (analog or digital), and the like. As used herein, a "balance status" refers to a condition, state, attribute, value, and/or characteristic, of one or more members, components, structures, and/or openings relative to a state of desired, correct, and/or equal proportions, configuration, alignment, and/or orientation between a reference set of one or more members, components, structures, and/or openings and the one or more members, components, structures, and/or openings being evaluated, measured, or examined. In certain embodiments, the balance status can be a binary condition, state, attribute, value, and/or characteristic. For example, a relationship between the one or more structures or openings and a reference set of one or more structures or openings may be either balanced or unbalanced (also referred to as imbalanced).

Alternatively, or in addition, a balance status can be a condition, state, attribute, value, and/or characteristic within a range of possible conditions, states, attributes, values, and/or characteristics. For example, in one embodiment, a balance status may be measured with respect to a scale or range of degrees between a positive maximum value and a negative minimum value where a balance status of zero on the range represents a balanced state and a non-zero value along the range represents an unbalanced state. In one embodiment, a range used to measure the balance status may extend from −5 degrees to +5 degrees.

In certain embodiments, a balance status can represent whether, or not, a superior resection of one bone of a joint is parallel to an inferior resection of another bone of the joint. In another embodiment, a balance status can represent a degree to which a superior resection of one bone of a joint is, or is not, parallel to an inferior resection of another bone of the joint. In another embodiment, a balance status can represent how two bones of a joint and space/opening between them relate to a medial collateral ligament and a lateral collateral ligament interact to each other to achieve a desired relationship with the joint.

In one embodiment, the balance indicator 126 indicates a balance status between the superior plate 118 and the inferior plate 120. Alternatively, or in addition, the balance indicator 126 may indicate a balance status for a joint 108 and/or between a medial collateral ligament and a lateral collateral ligament of a joint 108. Alternatively, or in addition, the balance indicator 126 may indicate a balance status between a first bone and a second bone. In the context of knee arthroplasty, the balance indicator 126 may indicate whether the arthroplasty procedure, if completed with implants on the measured bone surfaces, is likely to be varus, valgus, or balanced.

The balance indicator 126 can be connected to one, or the other, or both, of superior plate 118 and the inferior plate 120. In one embodiment, the balance indicator 126 connects to the superior plate 118. The balance indicator 126 is illustrated as a dashed region of the gap gauge 100 because one or more components or elements in the dashed region can serve as the balance indicator 126 in different embodiments. For example, in one embodiment, a user may observe a non-parallel position of the superior plate 118, or part of the superior plate 118, and such observation may serve as the balance indicator 126.

Figure 1C:
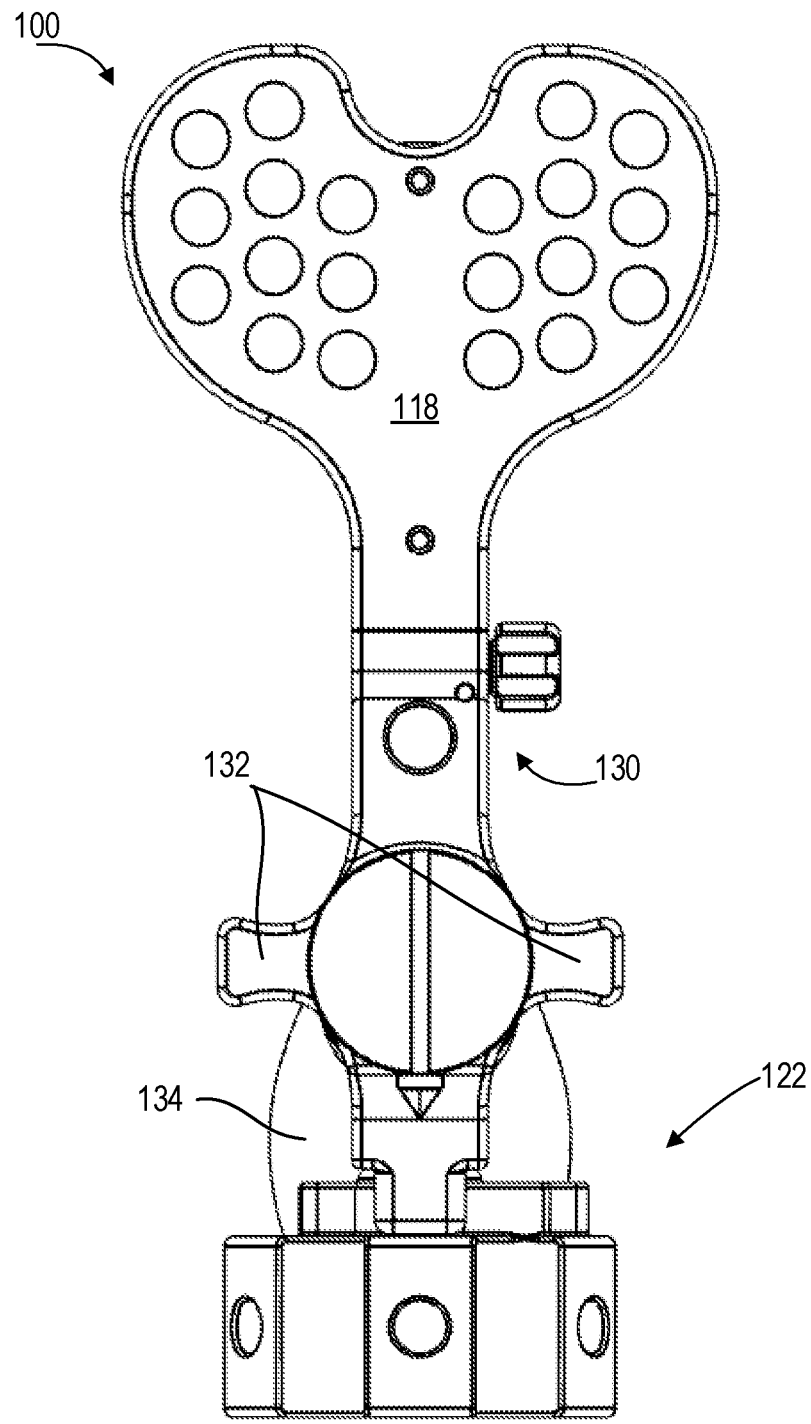
FIGS. 1C-1I are a top view, bottom view, side views, rear view, and front view of the gap gauge of FIG. 1A, according to one embodiment of the present disclosure.

FIGS. 1C-1I illustrate a top view (FIG. 1C), bottom view (FIG. 1D), side views (FIG. E-G), rear view (FIG. 1H), and front view (FIG. 1I) of one embodiment of a gap gauge 100. FIG. 1C illustrates an embodiment that includes a lock-out mechanism 130, a pair of grips 132, and a handle 134. As used herein, a "handle" refers to a structure used to hold, control, or manipulate a device, apparatus, component, tool, or the like. A "handle" may be designed to be grasped and/or held in one or more hands of a user.

In certain embodiments, the lock-out mechanism 130 can be used by a user to disable, prevent, or turn off actuation of the balance indicator 126 to indicate a balance status. As used herein, a "lock-out mechanism" refers to an apparatus, instrument, structure, device, component, system, assembly, hardware, software, firmware, circuit, module, or logic structured, organized, configured, programmed, designed, arranged, or engineered to prevent, mitigate, or stop operation of a balance indicator of a gap gauge such that the balance indicator does not report a balance status when the gap gauge is actuated. In one embodiment, the lock-out mechanism can prevent rotation of a plate connected to the balance indicator of a gap gauge. The pair of grips 132 can be used by a user to position the superior plate 118 relative to the inferior plate 120. For example, a user may grab the pair of grips 132 with one hand and hold the handle 134 with another hand and pull up on the grips 132 to separate the superior plate 118 and the inferior plate 120.

Figure 1D:
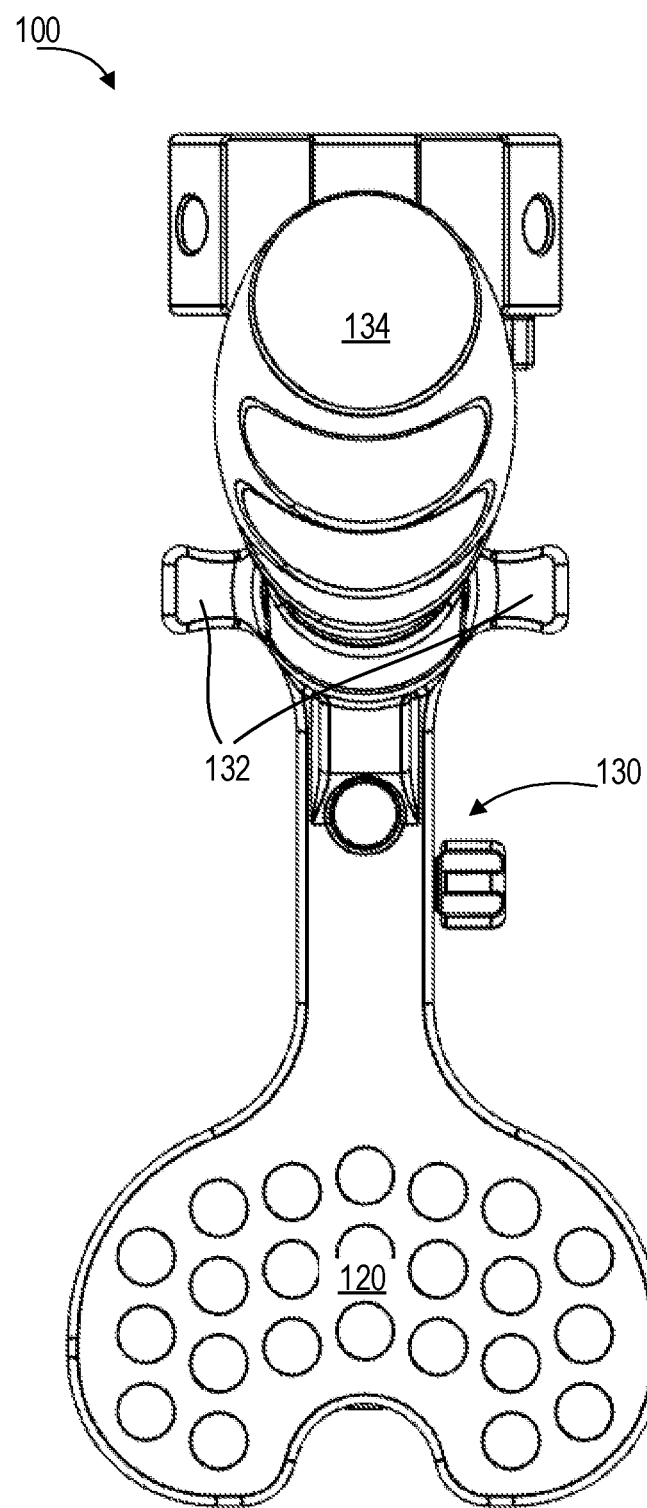

FIG. 1D illustrates a bottom view of one embodiment of the gap gauge 100. The view shows the inferior plate 120, lock-out mechanism 130, grips 132, and handle 134.

Figure 1E:
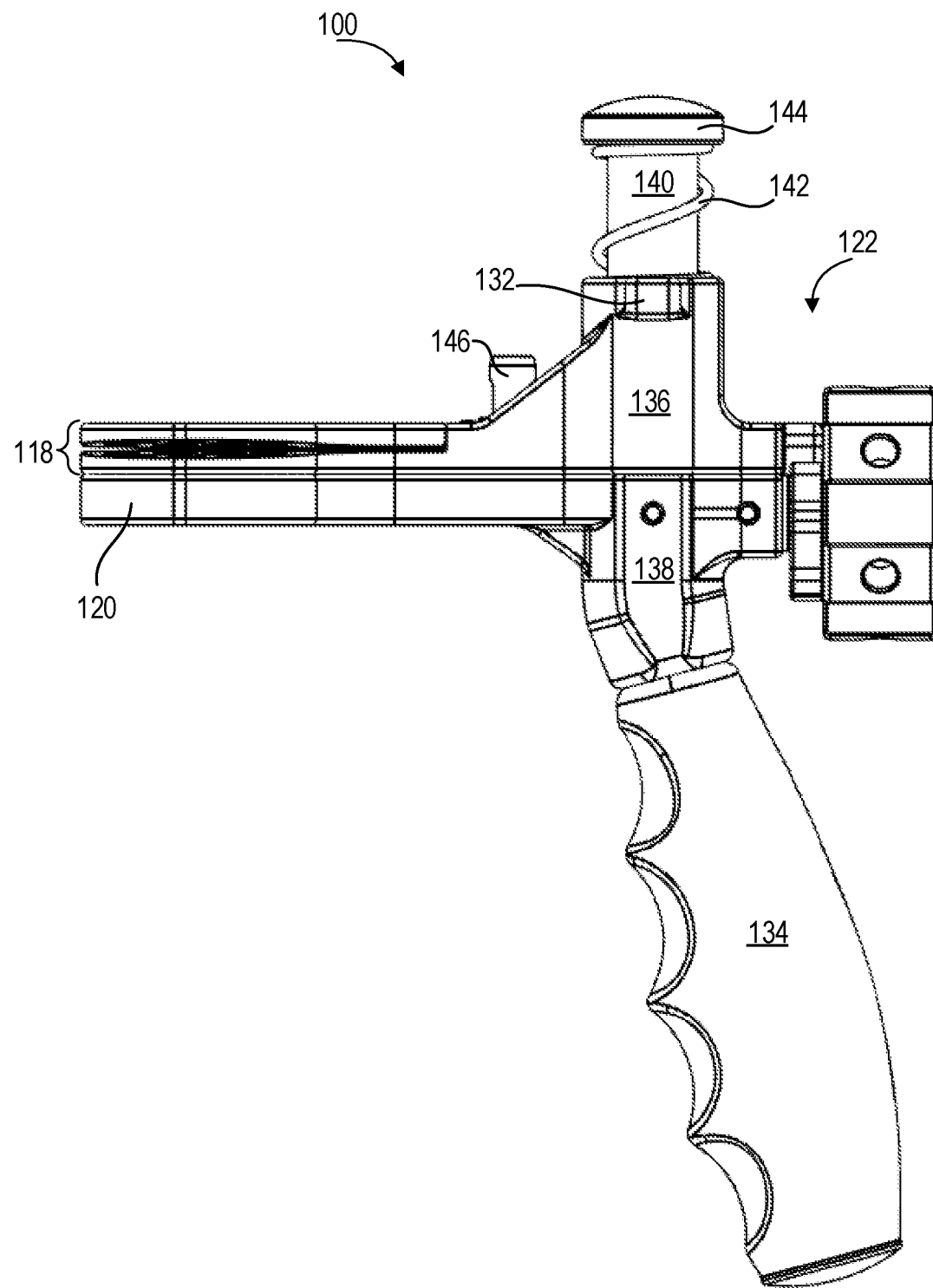

FIG. 1E illustrates a side view of one embodiment of the gap gauge 100. The view shows the superior plate 118, inferior plate 120, separator 122, a grip 132, and a handle 134. In addition, the illustrated embodiment includes a superior body 136, an inferior body 138, a shaft 140, and a spring 142. As used herein, a "body" refers to a main or central part of a structure. In one embodiment, a body may include a housing or frame or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like. As used herein, a "spring" refers to an elastic structure that stores mechanical energy. Springs can be made of a variety of elastic material such as spring steel and can be cylindrical and/or helical in shape. Various types of springs can be used including coil springs, torsion springs, and the like. (Search "spring (device)" on Wikipedia.com Nov. 28, 2020. Modified. Accessed Jan. 6, 2020.)

The superior body 136 provides structural support and integrity for the gap gauge 100 and may house one or more parts of the gap gauge 100. The inferior body 138 provides structural support and integrity for the gap gauge 100 and may house one or more parts of the gap gauge 100. In one embodiment, the superior plate 118 extends from the superior body 136 and the inferior plate 120 extends from the inferior body 138.

The shaft 140 may couple or connect the superior body 136 to the inferior body 138. The shaft 140 may slidably couple with the superior body 136 to the inferior body 138. The slidable coupling between the shaft 140, the superior body 136, and the inferior body 138 permits adjustment of the displacement 128.

In one embodiment, the shaft 140 may fit within an opening in the superior body 136 and pass through the superior body 136 to engage the inferior body 138. In certain embodiments, the shaft 140 can include threads on the outside of one end of the shaft 140. The threads of the shaft 140 may engage threads of an opening in the inferior body 138 to connect the shaft 140 to the inferior body 138. The shaft 140 may include a head 144 on one end opposite an end that includes the threads.

The opening in the superior body 136 can be sized to accept the shaft 140 and the spring 142 coiled around the outside of the shaft 140. The spring 142 may contact the superior body 136 and the head 144. The shaft 140 and spring 142 cooperated to retain the superior body 136 connected to the inferior body 138. In one embodiment once assembled in the gap gauge 100, the spring 142 may be biased against the head 144 and the superior body 136. The spring 142 can bias the superior body 136 in opposition to movement of the superior plate 118 away from the inferior plate 120.

In certain embodiments, the gap gauge 100 may include a post 146. The post 146 may slidably engage the superior body 136 and be connected to the inferior body 138. In one embodiment, the post 146 may be screwed into an opening in the superior body 136. The post 146 may cooperate with the shaft 140 to maintain movement of the superior body 136 along a single axis.

Figure 1F:
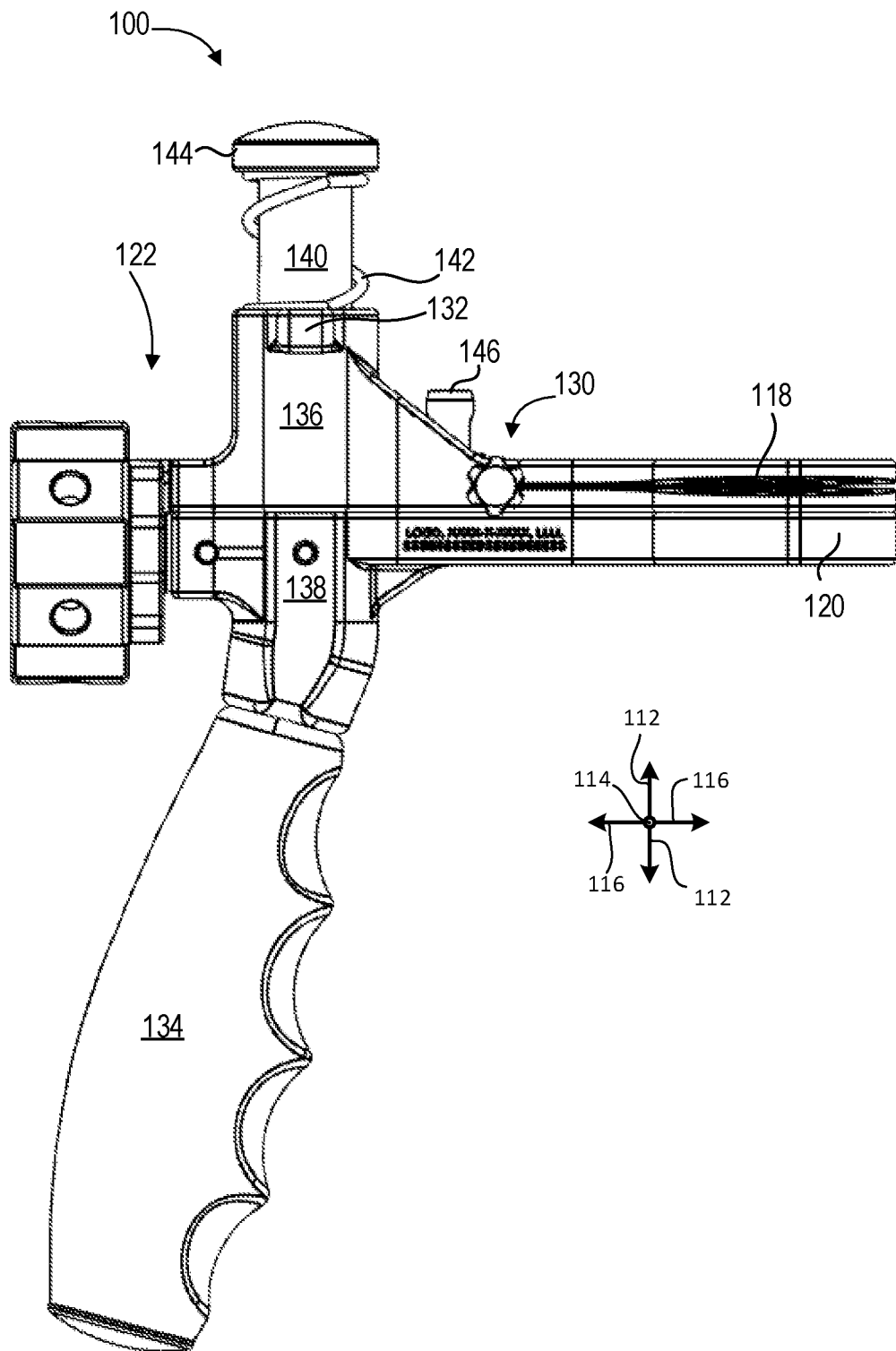

FIG. 1F illustrates a side view of one embodiment of the gap gauge 100. The side view shows the superior plate 118, inferior plate 120, separator 122, a lock-out mechanism 130, a grip 132, a handle 134, a superior body 136, inferior body 138, a shaft 140, a spring 142, and a post 146.

Figure 1G:
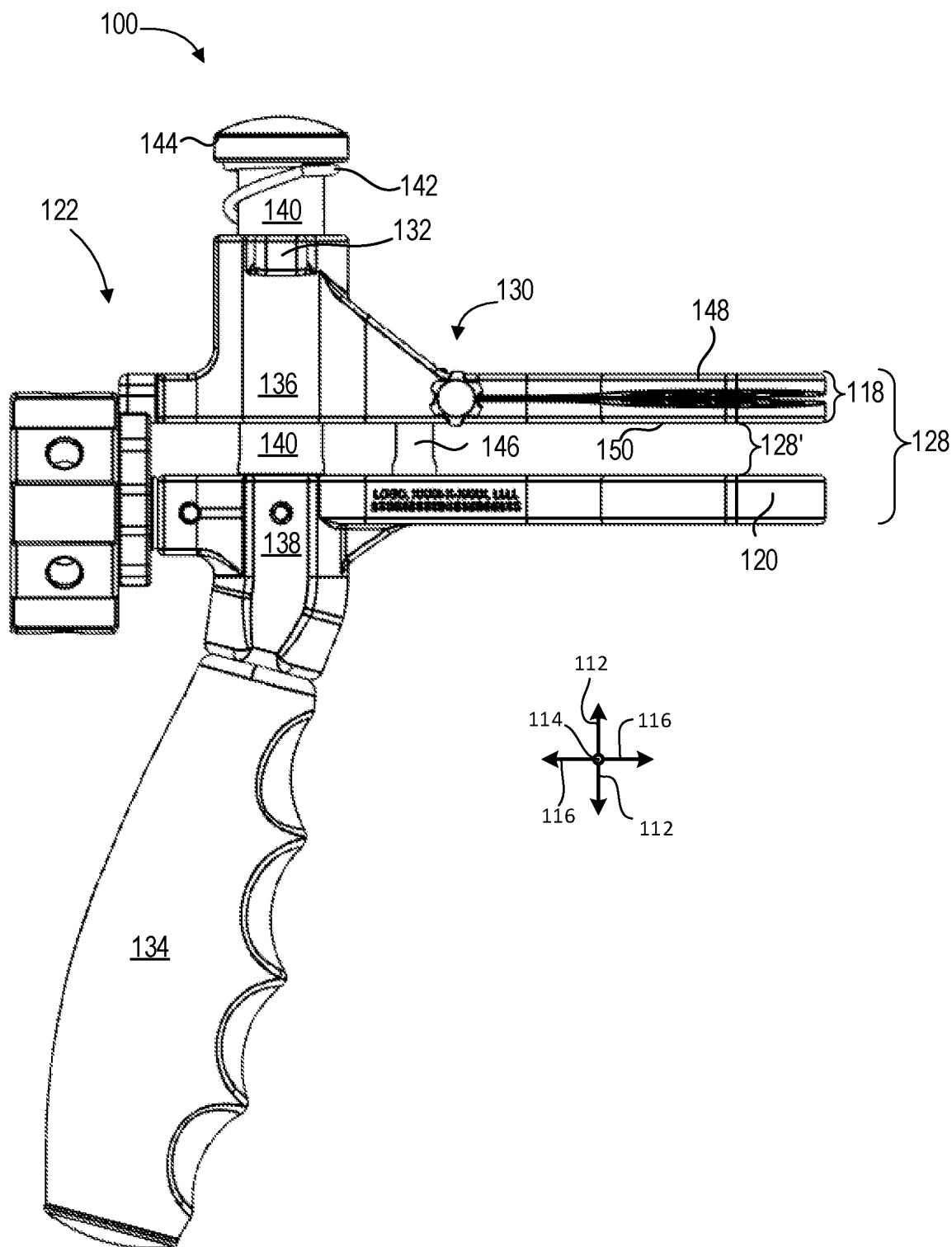

FIG. 1G illustrates a side view of one embodiment of the gap gauge 100. The side view shows the superior plate 118, inferior plate 120, separator 122, a lock-out mechanism 130, a grip 132, a handle 134, a superior body 136, inferior body 138, a shaft 140, spring 142, and a post 146.

FIG. 1G illustrates the gap gauge 100 with the separator 122 actuate such that the superior plate 118 and inferior plate 120 are displaced from each other by a displacement 128. In one embodiment, the displacement 128 is a measure between an external surface of the superior plate 118 and an external surface of the inferior plate 120. Those of skill in the art will recognize that a displacement can also be a measure between an internal surface of the superior plate 118 and an internal surface of the inferior plate 120 indicated by displacement 128'.

In the illustrated embodiment, the gap gauge 100 may include a superior plate 118 that includes a pivot plate 148 and a support plate 150. The pivot plate 148 can be connected, or coupled, to the support plate 150 such that the pivot plate 148 can serve as a balance indicator 126. In one embodiment, the pivot plate 148 can pivot about the anterior-posterior axis 116 relative to the support plate 150. As used herein, a "support plate" refers to a plate structured, organized, configured, programmed, designed, arranged, or engineered to support a load.

Figure 1H:
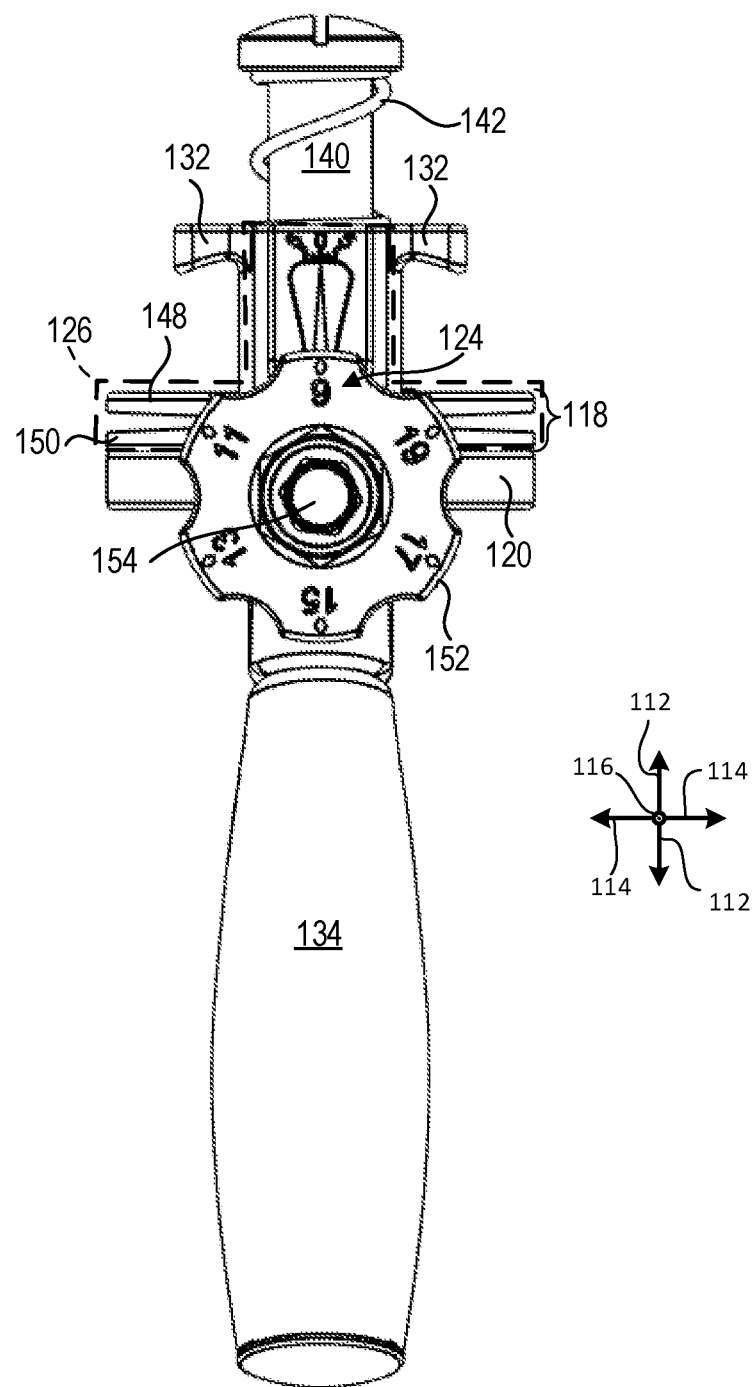

FIG. 1H illustrates a rear view of one embodiment of the gap gauge 100. The rear view shows the superior plate 118, inferior plate 120, separation indicator 124, balance indicator 126, grips 132, handle 134, shaft 140, spring 142, pivot plate 148, and support plate 150. In one embodiment, the inferior plate 120 can be a first plate and the superior plate 118 can be a second plate, or vice versa. Furthermore, in certain embodiments, the inferior plate 120 can be a second plate and the pivot plate 148 can be the first plate, or vice versa. In such embodiments, the gap gauge 100 may not include a support plate 150.

FIG. 1H illustrates an embodiment of a gap gauge 100 that includes a driver 152 and a fastener 154. The driver 152 serves to actuate the separator 122. The driver 152 can include a circumference having curved slots that facilitate rotating the driver 152. In one embodiment, the driver 152 serves to engage the separator 122 such that a displacement 128 is maintained. As used herein, a "driver" refers to a mechanical piece, component, or structure for imparting motion to another piece, component, or structure. ("driver." Merriam-Webster.com. Merriam-Webster, 2021. Web. 6 Jan. 2021. Modified.) In certain embodiments, a driver can be a wheel configured or connected to other parts such that rotation or motion of the driver causes motion of other interconnected or intercoupled parts of a component, system, apparatus, or device.

The fastener 154 secures the driver 152 to the gap gauge 100. In one embodiment, the fastener 154 is a bolt that screws into the inferior body 138 and permits the driver 152 to rotate freely about the bolt.

Figure 1I:
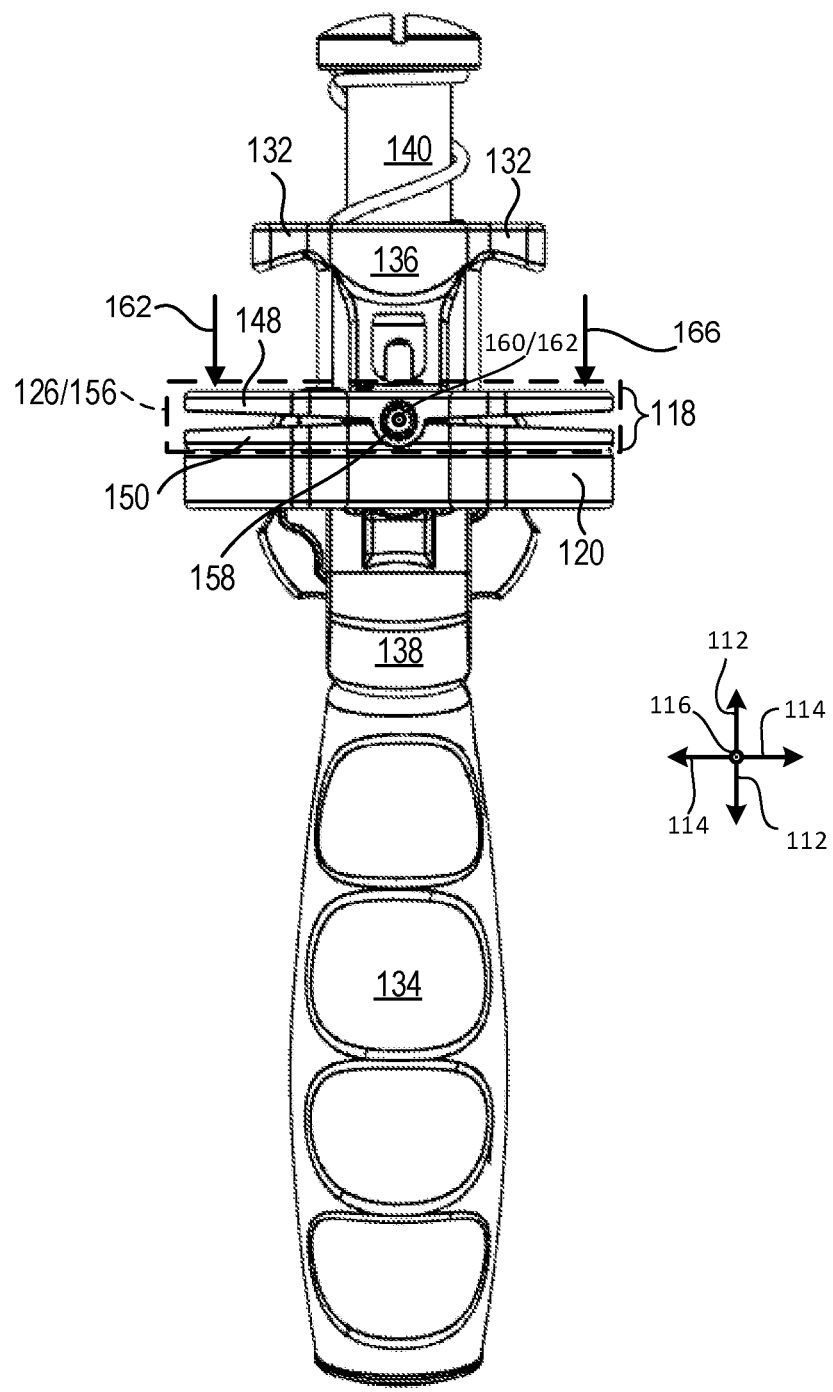

FIG. 1I illustrates a front view of one embodiment of the gap gauge 100. The front view shows the superior plate 118, inferior plate 120, grips 132, handle 134, shaft 140, spring 142, pivot plate 148, and support plate 150. In one embodiment, the balance indicator connects to a second plate, such as superior plate 118, and the balance indicator includes a hinge 156 that pivotally connects the superior plate 118 to the gap gauge 100. In one embodiment, the hinge 156 connects to the support plate 150.

As used herein, a "hinge" refers to an apparatus, instrument, structure, device, component, member, system, assembly, or module structured, organized, configured, designed, arranged, or engineered to connect two structures such that one structure can rotate about a fixed longitudinal axis of the hinge with respect to the other structure. In one embodiment, a hinge may be considered a mechanical bearing that restricts relative movement of the two structures to a desired kind of movement. In certain embodiments, various types of hinges can be used including a barrel hinge, a butt hinge, a butterfly hinge, a case hinge, a concealed hinge, a continuous/piano hinge, a flag hinge, an H hinge, an HL hinge, a pivot hinge, a self-closing hinge, a spring hinge, a living hinge, a coach hinge, a flush hinge, or the like.

A hinge can include a pin, one or more knuckles (also referred to as loops, joints, nodes, curls, etc.), and one or more leaves. As used herein, a "pin" refers to a cylindrical structure having a cross-sectional diameter small enough to fit within openings of one or more knuckles of a hinge. In certain embodiments, the pin can include a head on one end, the head can be larger than a diameter of the openings of the one or more knuckles such that the head prevents the pin from passing completely through the openings of the one or more knuckles. A pin can be made from a variety of material including metal, plastic, wood, or the like. A leaf is a structure that extends laterally from the one or more knuckles and can be integrated with or connected to a structure that is intended to pivot or rotate about the pin. In certain embodiments, a hinge can include two or more leaves. A leaf can be a planar structure.

A knuckle is a structure with an opening sized to receive the pin. A knuckle connects to at least one leaf. A knuckle can have a circular longitudinal cross-section and can be cylindrical. In certain embodiments, each leaf includes a knuckle that can be aligned along a longitudinal axis of the hinge. Once the one or more knuckles are aligned along the longitudinal axis of the hinge, the pin can be inserted into openings of the one or more knuckles to secure the leaf/leaves connected to each knuckle.

FIG. 1I includes a front view of one embodiment of a balance indicator 126. In such an embodiment, the superior plate 118 can include a pivot plate 148 coupled to the gap gauge 100 by the hinge 156. In certain embodiments, the hinge 156 may serve both as a hinge and as a balance indicator 126. For example, a user may view the hinge 156 during an arthroplasty procedure and detect that the pivot plate 148 (or the superior plate 118) is oriented non-parallel to an inferior plate 120. In this manner, a user can determine a balance status.

In one embodiment, the hinge 156 can include a pin 158. The pin 158 can couple, or connect, to the pivot plate 148.

The pin 158 can connect the support plate 150 and the pivot plate 148. In another embodiment, the hinge 156 may not connect to a support plate 150. The pin 158 has a longitudinal axis 160 that is a pivot axis 162 for the pivot plate 148. A force (e.g., a force in the direction of arrow 164 or arrow 166) applied to the pivot plate 148 can rotate the pivot plate 148 about the pin 158. As used herein, a "pivot axis" refers to an axis about which a structure pivots or rotates.

During an arthroplasty procedure, a user may align the longitudinal axis of the pin 158, and hence the pivot axis of the pivot plate 148, with an anterior-posterior axis 116 of a patient in order to determine a balance status. Alternatively, or in addition, during an arthroplasty procedure, a user may position the longitudinal axis of the pin 158, and hence the pivot axis of the pivot plate 148, parallel to an anterior-posterior axis 116 of a patient in order to determine, or measure, a varus condition, a balanced condition, or a valgus condition.

If the pivot plate 148 pivots about the pin 158 in the direction of arrow 164, this may indicate a varus condition of a first bone relative to a second bone. If the pivot plate 148 pivots about the pin 158 in the direction of arrow 166, this may indicate a valgus condition of a first bone relative to a second bone. If the pivot plate 148 does not pivot about the pin 158, this may indicate a balanced condition of a first bone relative to a second bone.

Figure 2:
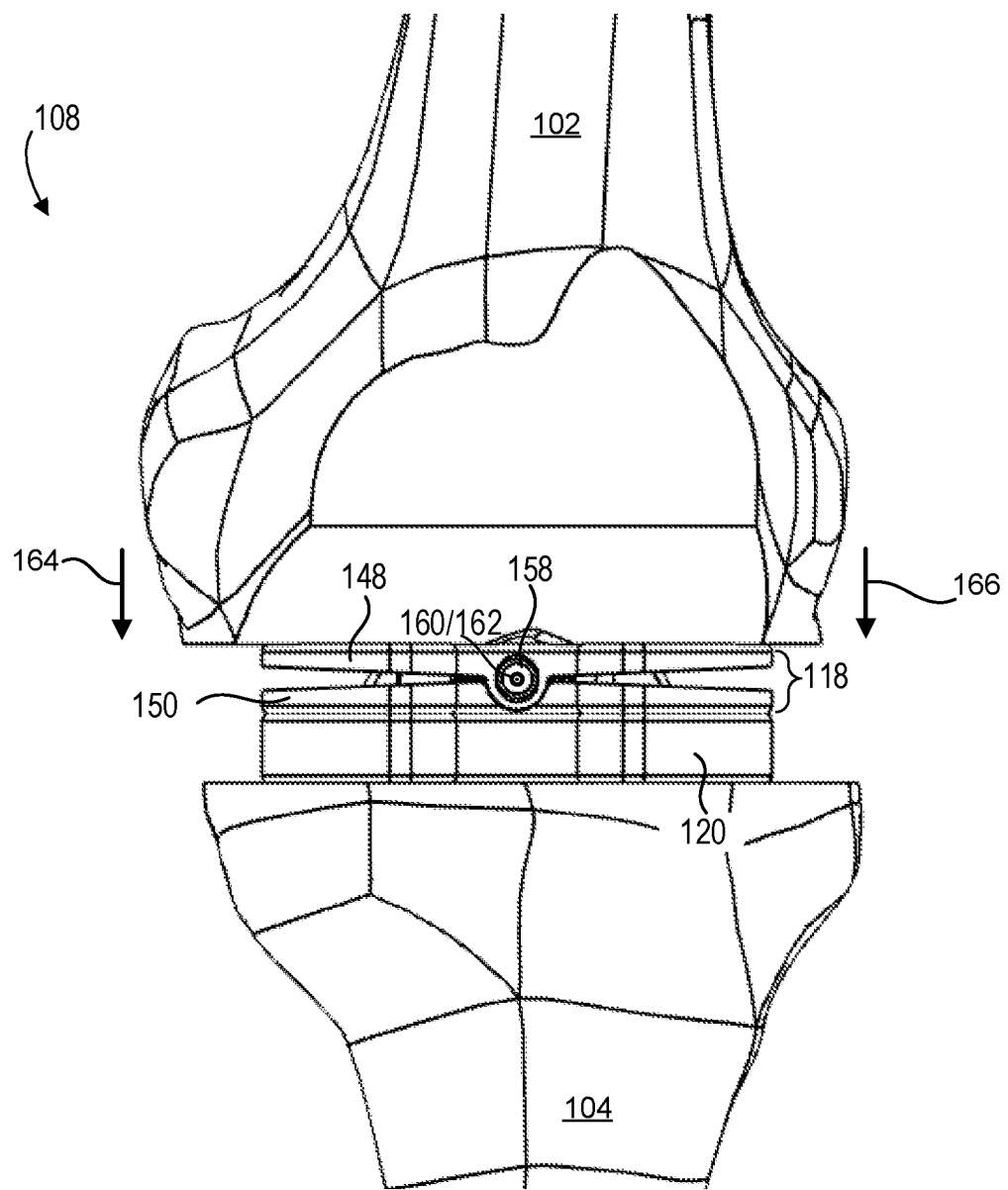
FIG. 2 is an anterior view of a knee joint with the gap gauge of FIG. 1A inserted between two bones.
Figure 3:
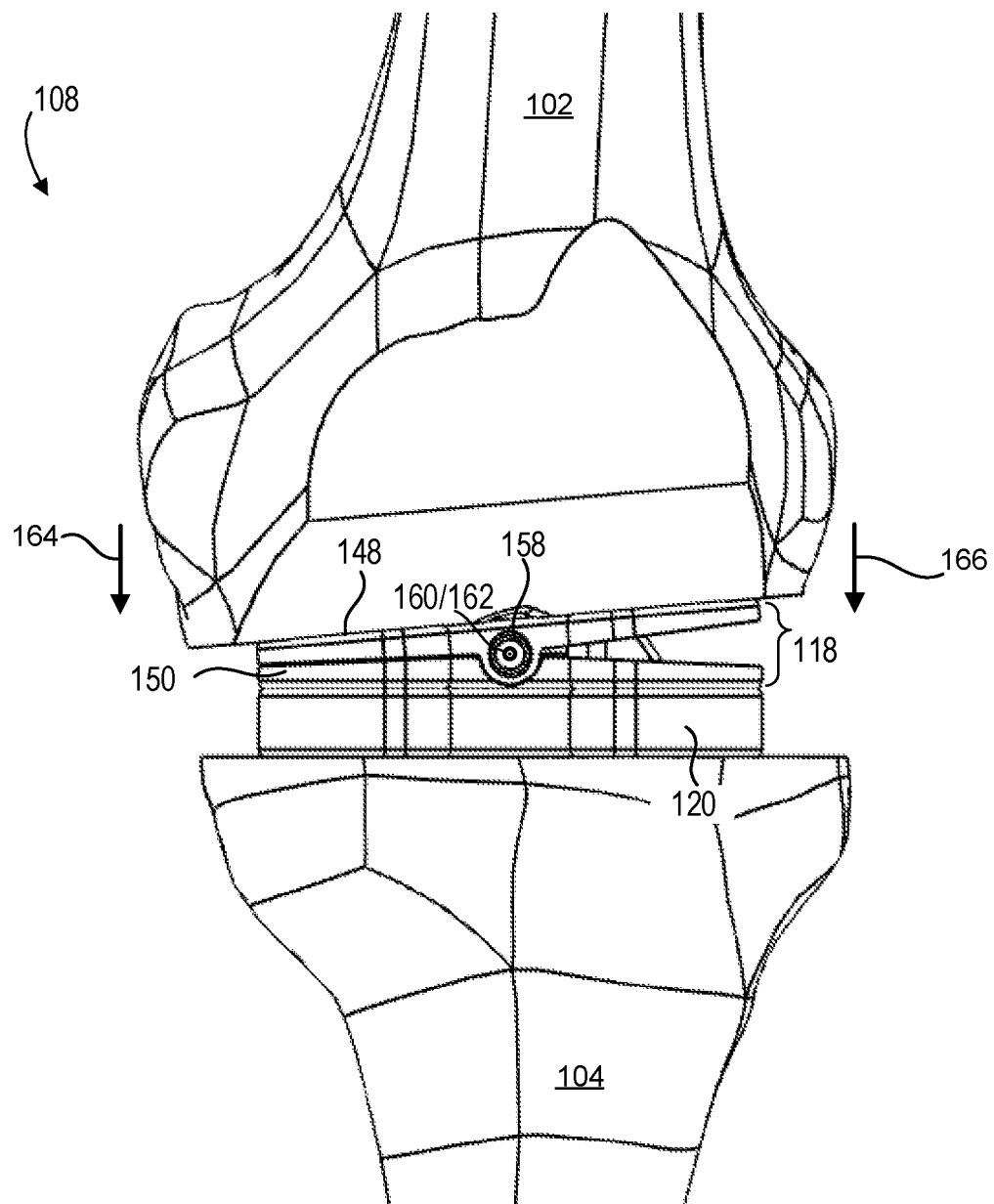
FIG. 3 is an anterior view of a knee joint with the gap gauge of FIG. 1A inserted between two bones.

FIGS. 2 and 3 are anterior views of a knee joint with the gap gauge 100 of FIG. 1A inserted between two bones and show a balanced condition and a varus condition, respectively. A figure showing bones of a joint for a valgus condition is not specifically shown; however, those of skill in the art will appreciate that a valgus condition is simply an angle, or orientation, of the bones of FIG. 3 such that the pivot plate 148 pivots in the direction of arrow 166 rather than arrow 164.

As used herein, a "valgus condition" refers to a state of a bone or joint having an undesired outward angulation (angled laterally, away from the body's midline) of the distal segment of a bone or joint. For example, in a valgus condition of the knee, the distal part of the leg below the knee is deviated outward, in relation to the femur, resulting in a knock-kneed appearance. The opposite of varus is called valgus. A varus condition at the knee results in a bowlegged appearance with the distal part of the leg deviated inward, in relation to the femur. (Search "valgus deformity" on Wikipedia.com Oct. 20, 2020. Modified. Accessed Jan. 6, 2020.) A valgus condition can be experienced in a variety of joints, including but not limited to, ankle joints, elbow joints, foot joints, hand joints, hip joints, knee joints, toe joints, wrist joints, and the like. As used herein, a "varus condition" refers to a state of a bone or joint having an undesired inward angulation (medial angulation, that is, towards the body's midline) of the distal segment of a bone or joint. The opposite of varus is called valgus. The terms varus and valgus refer to the direction that the distal segment of the joint points. For example, a varus condition at the knee results in a bowlegged appearance with the distal part of the leg deviated inward, in relation to the femur. In a valgus condition of the knee, the distal part of the leg below the knee is deviated outward, in relation to the femur, resulting in a knock-kneed appearance. (Search "varus deformity" on Wikipedia.com Oct. 20, 2020. Modified. Accessed Jan. 6, 2020.) A varus condition can be experienced in a variety of joints, including but not limited to, ankle joints, elbow joints, foot joints, hand joints, hip joints, knee joints, toe joints, wrist joints, and the like. As used herein, a "balanced condition" refers to a state of a bone and/or joint having a desired alignment of the bone or joint with a central axis of a limb or anatomical structure that includes the bone and/or joint. In certain embodiments, a balanced condition refers to a condition of the bone or joint that is not a varus condition and is not a valgus condition.

FIG. 2 illustrates a balanced condition for the joint 108. The superior plate 118 and/or pivot plate 148 contacts the femur 102. The inferior plate 120 contacts the tibia 104. The pivot plate 148 is parallel to the inferior plate 120. In the illustrated embodiment, a force, or tension, in the joint 108, or movement in direction of arrow 164 is offset by a force, or tension, in the joint 108 or movement in direction of arrow 166. As used herein, a "tension" refers to a tensile force that is applied across an elongated structure. For example, a ligament such as a lateral collateral ligament may experience tension due to how the ligament is attached to a femur bone and tibia bone and stretched during flexing of the knee joint.

FIG. 3 illustrates a varus condition for a joint 108. The superior plate 118 and/or pivot plate 148 contacts the femur 102. The inferior plate 120 contacts the tibia 104. The pivot plate 148 is not parallel to the inferior plate 120. A slant in the superior plate 118 and/or pivot plate 148 can be caused by various factors, including but not limited to, an angle at which the femur 102 and/or tibia 104 has been sectioned, forces acting on the joint 108 by soft tissue and/or ligaments, and the like. In the illustrated embodiment, a force, or tension, in the joint 108, or movement in direction of arrow 164 by a surface of the femur 102 or tibia 104 is greater than a force, or tension, in the joint 108 or movement in direction of arrow 166 by a surface of the femur 102 or tibia 104.

Those of skill in the art recognize that a valgus condition can exist in the joint 108 illustrated in FIG. 3 if the superior plate 118 and/or pivot plate 148 rotates about the longitudinal axis 160 in the direction of arrow 166. Such a slant can be caused by various factors, including but not limited to, an angle at which the femur 102 and/or tibia 104 has been sectioned, forces acting on the joint 108 by soft tissue and/or ligaments, and the like. In such an embodiment, a force, or tension, in the joint 108, or movement in direction of arrow 166 by a surface of the femur 102 or tibia 104 is greater than a force, or tension, in the joint 108 or movement in direction of arrow 164 by a surface of the femur 102 or tibia 104.

Figure 4:
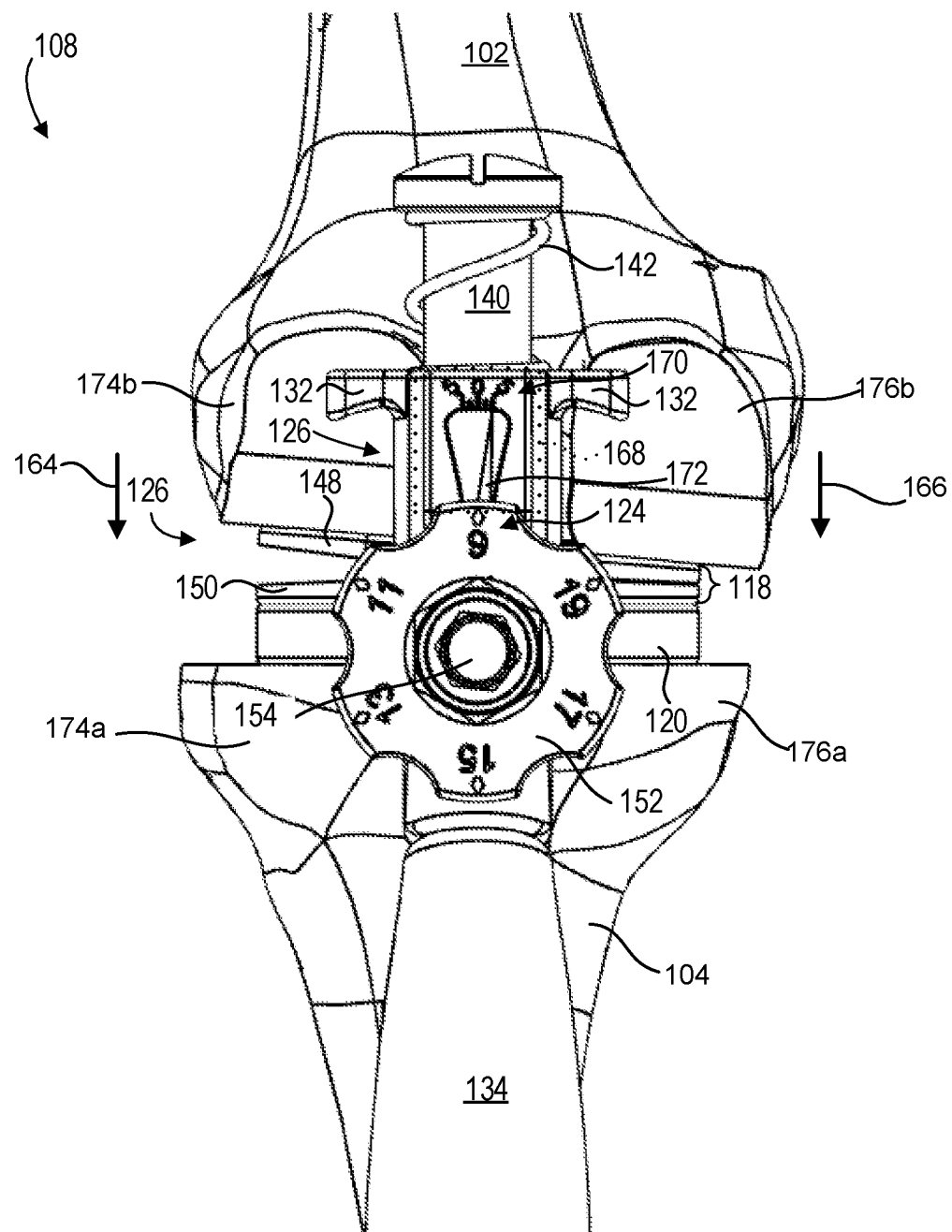
FIG. 4 is a posterior view of a knee joint with the gap gauge of FIG. 1A inserted between two bones.

FIG. 4 is a posterior view of a knee joint with a gap gauge 100 inserted between a femur 102 and a tibia 104. FIG. 4 illustrates a rear view of the gap gauge 100. FIG. 4 shows the superior plate 118, inferior plate 120, separation indicator 124, balance indicator 126, grips 132, handle 134, shaft 140, spring 142, pivot plate 148, support plate 150, driver 152, and fastener 154. The illustrated embodiment includes a balance gauge 168. In one embodiment, the balance gauge 168 can include a dial 170 and a needle 172.

FIG. 4 illustrates medial condyles 174a, 174b and lateral condyles 176a, 176b of a first bone (e.g., tibia 104) and a second bone (e.g., femur 102). As used herein, a "medial condyle" refers to one of the two projections on the lower extremity, distal end, of femur, the other being the lateral condyle. The medial condyle is larger than the lateral (outer) condyle due to more weight bearing caused by the center of mass being medial to the knee. (Search "medial condyle" on Wikipedia.com May 12, 2020. Modified. Accessed Jan. 6, 2020.) As used herein, a "lateral condyle" refers to one of the two projections on the lower extremity, distal end, of the femur. The other one is the medial condyle. The lateral condyle is prominent and is broader both in its front-to-back and transverse diameters. (Search "lateral condyle" on Wikipedia.com Apr. 17, 2020. Modified. Accessed Jan. 6, 2020.)

In the illustrated embodiment, the superior plate 118 is positionable to engage, or contact, the femur 102 and the inferior plate 120 is positionable to engage, or contact, the tibia 104. The superior plate 118 can be shaped, or configured, to engage a medial condyle 174b and a lateral condyle 176b of the femur 102. The inferior plate 120 can be shaped, or configured, to engage a medial condyle 174a and a lateral condyle 176a of the tibia 104. One example of a shape suitable of a superior plate 118 for engaging a medial condyle 174b and a lateral condyle 176b of the femur 102 is illustrated in FIG. 1C. One example of a shape suitable of an inferior plate 120 for engaging a medial condyle 174a and a lateral condyle 176a of the tibia 104 is illustrated in FIG. 1D. Of course, the size and shape of the superior plate 118 and inferior plate 120 can be different depending on the age and size of the patient (e.g., smaller for children and larger for adults).

The balance gauge 168, in one embodiment, provides a visual indication of a balance status and can provide specific information about a magnitude of imbalance or balance of the joint 108 to a user of the gap gauge 100. As used herein, a "balance gauge" refers to an apparatus, instrument, structure, device, component, system, assembly, hardware, software, firmware, circuit, module, or logic structured, organized, configured, programmed, designed, arranged, or engineered to measure an attribute, characteristic, state, or condition of another structure or object or set of structures or objects. In one embodiment, the balance gauge is structured, organized, configured, programmed, designed, arranged, or engineered to measure a balance status between two or more structures. The balance gauge 168 can be connected to the balance indicator 126 such that movement of the balance indicator 126 is reflected and/or reported by the balance gauge 168. In this manner, the balance gauge 168 can measure the balance status.

FIG. 4 illustrates that a user can determine both a displacement, using the separation indicator 124, and a balance status, using the balance indicator 126 and/or the balance gauge 168 in a single view of the gap gauge 100. This can be helpful as other soft tissue or equipment may interfere with determining either, or both, of a displacement and a balance status during an arthroplasty procedure.

Figure 5A:
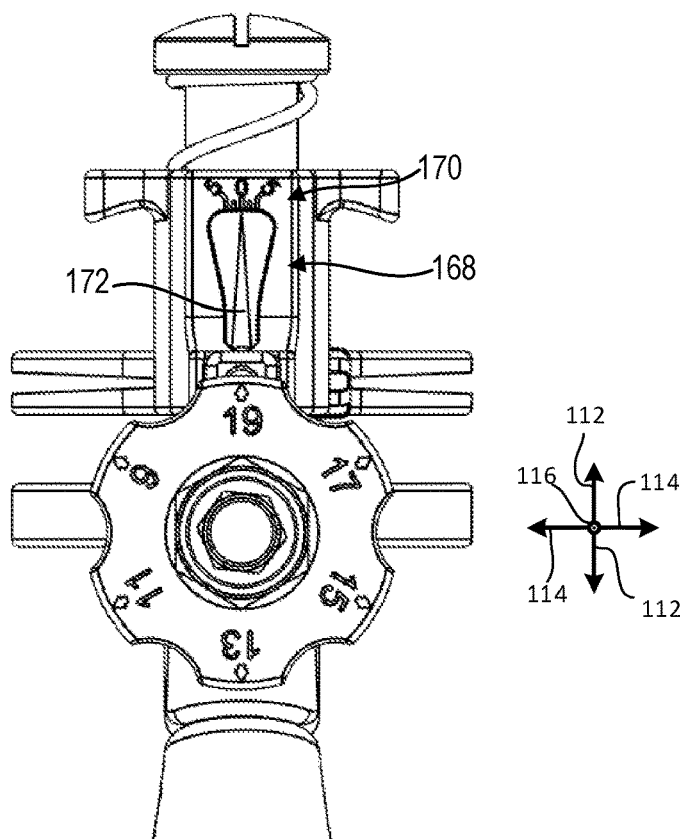
FIGS. 5A-5C are rear views of the gap gauge of FIG. 1A illustrating different balance status states.
Figure 5B:
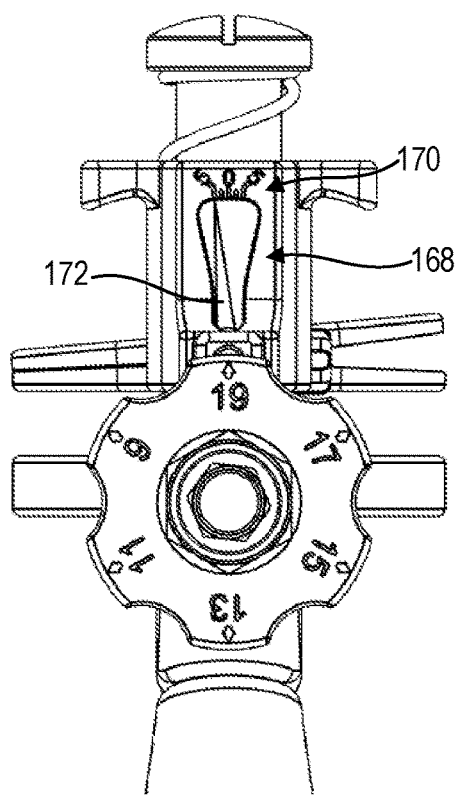
Figure 5C:
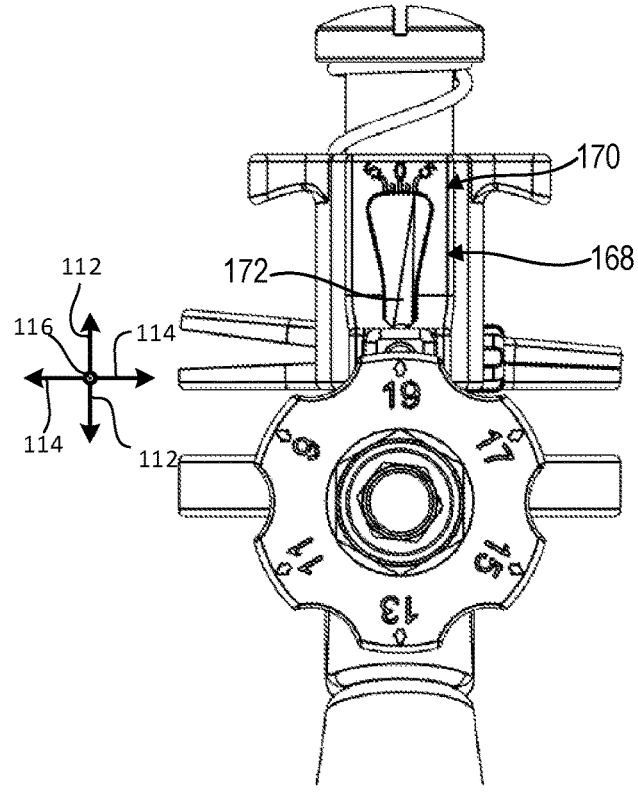

FIGS. 5A-5C are rear views of an exemplary gap gauge 100 illustrating different balance status states. FIGS. 5A-5C illustrate a dial 170 and a needle 172 coupled or connected to a balance indicator 126 in order to measure a balance status. As used herein, a "dial" refers to a face upon which some measurement is registered usually by means of graduations and a pointer, such as a needle. ("dial." Merriam-Webster.com. Merriam-Webster, 2021. Web. 6 Jan. 2021. Modified.) As used herein, a "needle" refers to a long thin structure that may include a point at one end and a coupler for connecting the needle to another structure.

In the illustrated embodiment, the dial 170 includes marks and each mark is positioned on a face of the dial 170. The marks can represent an angle of pivot, or movement, of a superior plate 118 and/or pivot plate 148 about the pin 158. Each mark on the face can represent a different measure of balance status. Alternatively, or in addition, marks positioned on a face of the dial can indicate a measure of the orientation of a superior plate 118 relative to an inferior plate 120.

In certain embodiments, the face can include numbers that identify different measures of a balance status. In one embodiment, the dial 170 includes marks for angles ranging from −5 degrees to +5 degrees with 0 degrees representing a balanced condition. As the superior plate 118 and/or pivot plate 148 pivot or rotate about the pin 158, the rotation is measured by and conveyed to the balance indicator 126. Movement of the balance indicator 126 transfers to the needle 172 and moves the needle 172 to point toward a mark on the face that reflects the balance status. Rotation of the superior plate 118 or the inferior plate 120, about an anterior-posterior axis 116 of a patient, moves the needle 172 to point toward a mark on the face of the dial that reflects the orientation of the plates.

FIG. 5A illustrates an example balance gauge 168 of a gap gauge 100 that can be positioned to contact a first bone (See FIG. 1A) and a second bone (See FIG. 1A). Where the surfaces of the bones are parallel and/or forces within the joint 108 are balanced (e.g., a balance condition), a needle 172 of the balance gauge 168 may point to a middle mark of the dial 170 indicating a balance condition, no positive or negative degree of rotation about a pivot axis 162.

FIG. 5B illustrates an example balance gauge 168 of a gap gauge 100 that can be positioned to contact a first bone (See FIG. 1A) and a second bone (See FIG. 1A). Where the surfaces of the bones are not parallel and/or forces within the joint 108 are not balanced (e.g., a varus condition or valgus condition depending on which joint is being measured), a needle 172 of the balance gauge 168 may point to a mark (e.g., −5 degrees) on the left side of the middle mark of the dial 170 indicating an imbalance or non-balanced condition, a positive or negative degree of rotation about a pivot axis 162.

FIG. 5C illustrates an example balance gauge 168 of a gap gauge 100 that can be positioned to contact a first bone (See FIG. 1A) and a second bone (See FIG. 1A). Where the surfaces of the bones are not parallel and/or forces within the joint 108 are not balanced (e.g., a varus condition or valgus condition depending on which joint is being measured), a needle 172 of the balance gauge 168 may point to a mark (e.g., +5 degrees) on the right side of the middle mark of the dial 170 indicating an imbalance or non-balanced condition, a positive or negative degree of rotation about a pivot axis 162.

Figure 6A:
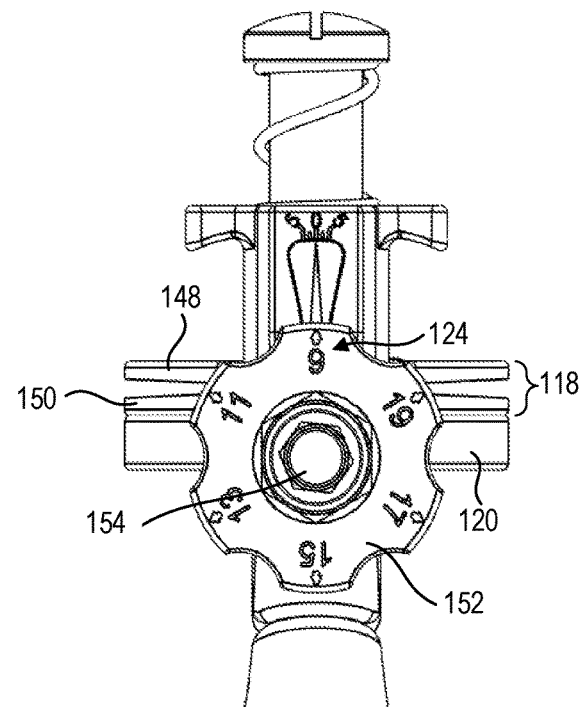
FIGS. 6A-6C are rear views of the gap gauge of FIG. 1A illustrating different displacements.
Figure 6B:
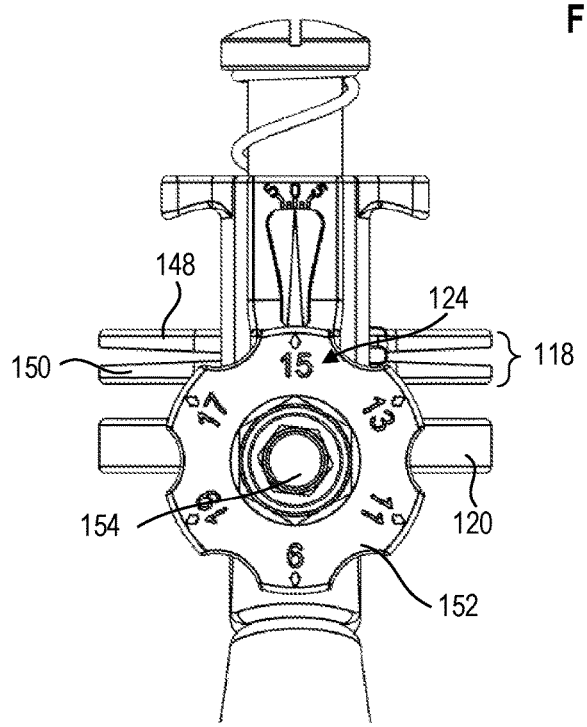
Figure 6C:
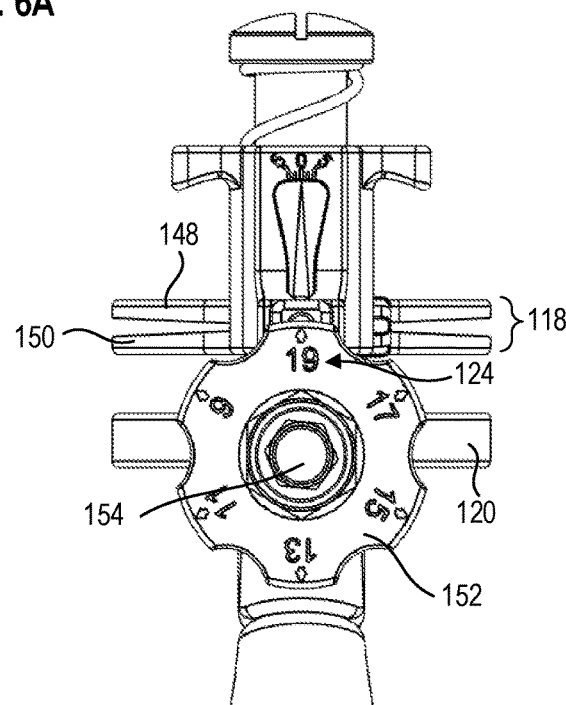

FIGS. 6A-6C are rear views of an exemplary gap gauge 100 illustrating different displacements. FIGS. 6A-6C illustrate a superior plate 118, inferior plate 120, and separation indicator 124. The superior plate 118 can include a pivot plate 148 and a support plate 150. FIGS. 6A-6C also illustrate a driver 152 and a fastener 154.

In the illustrated embodiment, the separation indicator 124 can include a face that may include a number that represents a measure for a displacement between an outer surface of the superior plate 118 and an outer surface of the inferior plate 120. For example, in the illustrated embodiment, a number at the top-most position of the face when viewed as illustrated may represent a current amount of displacement. For example, the "9" may represent a displacement of 9 millimeters. The face on the driver 152 can include a plurality of different marks and/or numbers (e.g., readings) that each may represent a different displacement between the superior plate 118 and inferior plate 120. The fastener 154 may permit the driver 152 to be rotated about a longitudinal axis of the fastener. The driver 152 is rotatable to a plurality of positions and each position may represent a different displacement that corresponds to the number on the face of the driver 152. The illustrated embodiment can include six different displacements and six numbers each representing a different displacement. (e.g., 9, 11, 13, 15, 17, and 19).

FIG. 6A illustrates an example separation indicator 124 of a gap gauge 100 that can be positioned within an opening 106 between a first bone (See FIG. 1A) and a second bone (See FIG. 1A). Once positioned, and the separator 122 is actuated to a desired displacement, a user can read the displacement by reading the number in the top-most position on the separation indicator 124. For example, in FIG. 6A the displacement is nine millimeters. For example, in FIG. 6B the displacement is fifteen millimeters. For example, in FIG. 6C the displacement is nineteen millimeters.

The separator 122 can be actuated to bring the superior plate 118 in contact with a resected surface of a femur 102 and the inferior plate 120 in contact with a resected surface of a tibia 104. As used herein, a "resected surface" refers to an outermost part or layer of a body structure that is exposed after a resection procedure. As used herein, a "resection" refers to a method, procedure, or step that removes tissue from another anatomical structure or body. A resection is typically performed by a surgeon on a part of a body of a patient. (Search "surgery" on Wikipedia.com May 26, 2021. CC-BY-SA 3.0 Modified. Accessed May 26, 2021.) Resection may be used as a noun or a verb. In the verb form, the term is "resect" and refers to an act of performing, or doing, a resection. Past tense of the verb resect is resected.

The superior plate 118 can be shaped, or configured, to facilitate contact with a resected surface of the femur 102. The inferior plate 120 can be shaped, or configured, to facilitate contact with a resected surface of the tibia 104. One example of a shape suitable for the superior plate 118 is illustrated in FIG. 1C. One example of a shape suitable for the tibia 104 is illustrated in FIG. 1D.

The separator 122 may be actuated by securing the handle 134 with one hand and then rotating the driver 152 to one or more of a plurality of displacement positions. Alternatively, or in addition, actuation of the separator 122 may include securing the gap gauge 100 in position using the handle 134, rotating the driver 152, and/or pulling on the grips 132 to separate the plates 118, 120. If the handle 134 is secured, the driver 152 rotated and the grips 132 pulled to separate the plates 118, 120 simultaneously or at about the same time an assistant may help with the actuation.

Figure 7:
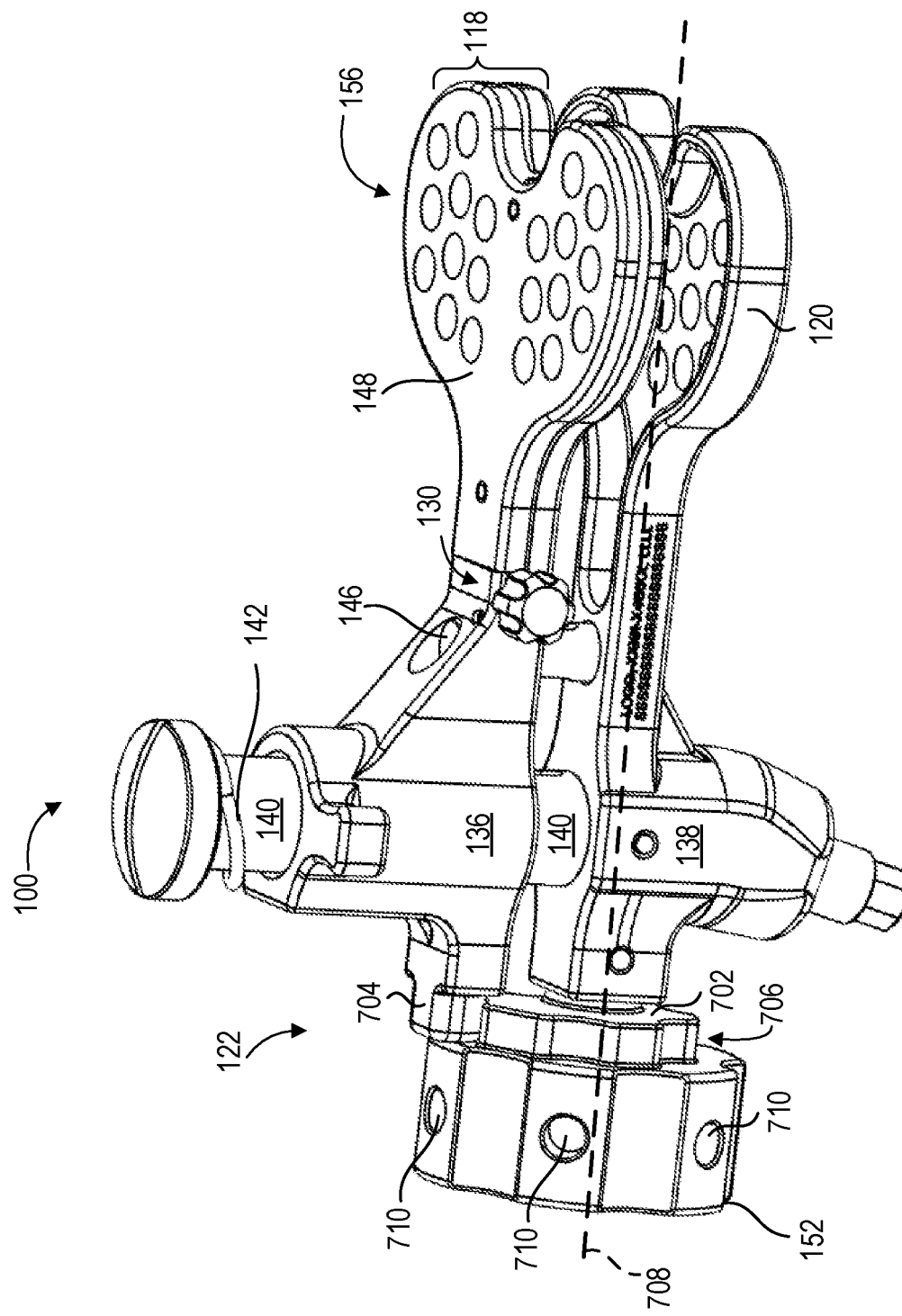
FIG. 7 is a perspective view of the gap gauge of FIG. 1A.

FIG. 7 is a perspective view of an example gap gauge 100. FIG. 7 illustrates a gap gauge 100 that includes a separator 122 that includes a cam 702 and a follower 704. As used herein, a "cam" refers to a mechanical device structured, organized, configured, programmed, designed, arranged, or engineered to translate motion of one form into motion of another form. For example, a cam can translate rotary motion into linear motion. Similarly, a cam can translate linear motion into rotary motion. A cam can be a rotating or sliding piece in a mechanical linkage used in transforming rotary motion into linear motion. A cam can be a part of a rotating wheel (e.g. an eccentric wheel) or shaft (e.g. a cylinder with an irregular shape) that strikes or moves a lever at one or more points on the rotating wheel's circular path. The cam can be a simple tooth or an eccentric disc or other shape that produces a smooth reciprocating (back and forth) motion in the follower, which is a lever configured to make contact with the cam. (Search "cam" on Wikipedia.com Dec. 26, 2020. Modified. Accessed Jan. 6, 2020.) Various types of cams can be used with the present disclosure. For example, the cam can be a radial cam, a disc cam, a cylindrical cam, or the like.

As used herein, a "follower" refers to a rigid structure that contacts a cam lobe profile. In one embodiment, the follower may translate motion of the cam to the follower and/or a structure connected to the follower. In certain embodiments, as the cam rotates the follower may slide along a contacting surface of the cam to thereby convert the rotary motion into a linear motion. A follower may also be referred to as a "cam follower" or "track follower." A cam follower is a type of structure, roller, or needle bearing designed to follow and/or contact a cam lobe profile of the cam. (Search "cam follower" on Wikipedia.com Nov. 13, 2020. Modified. Accessed Jan. 6, 2020.)

Various kinds of followers can be used in the present disclosure. The type and shape of a cam follower may be based on the kind of surface of the follower (referred to as a follower face) that contacts a contacting surface of the cam. In one embodiment, the follower is a stud that comes to a point to form a knife edge follower. Alternatively, or in addition, the follower face can have a variety of other shapes including, but not limited to a flat face, a mushroom face, a cylindrical face, a curved face, a semispherical face, and the like. In addition, the follower can include a roller on the end that contacts the contacting surface of the cam. The roller on the end of the follower can enable the follower to roll and or slide along the contacting surface of the cam.

In the illustrated embodiment, the cam 702 is connected to, or integrated with, the driver 152. The driver 152 connects to the inferior body 138 by way of the fastener 154. In this manner, the cam 702 connects to the inferior body 138. The cam 702 includes a contacting surface 706. As used herein, a "contacting surface" refers to a surface of a cam that contacts a follower. The orientation, placement, and position of the contacting surface can vary with the type of cam being used. In embodiments that use a radial cam the radial cam can have a central axis 708 and the contacting surface can be a surface of the cam that follows a circumference of the radial cam about the central axis 708.

Rotation of the driver 152 also rotates the cam 702. Rotation of the cam 702 moves the superior body 136 which adjusts the displacement of the superior plate 118 relative to the inferior plate 120. In one embodiment, the cam 702 is a radial cam and rotates about a common axis, the central axis 708, with the fastener 154. As used herein, a "radial cam" refers to a type of cam in which the cam has a central axis, and the contacting surface follows a circumference of the cam about the central axis. In a radial cam, the follower moves in a linear motion in a direction perpendicular to the central axis. The follower 704 can contact, or rest, on the cam 702.

The follower 704 is connected to the superior body 136. In one embodiment, the follower 704 may be biased against the contacting surface 706 by the spring 142 around the shaft 140. The follower 704 is sized and shaped to move the superior body 136 along the shaft 140 relative to the inferior body 138 as the follower 704 slides along, or is positioned along, the contacting surface 706. FIG. 7 illustrates one example embodiment, in which the support plate 150 couples to the separator 122 (e.g., by way of the cam 702, follower 704, and superior body 136) such that actuation of the separator 122 moves the support plate 150 vertically relative to the inferior plate 120.

FIG. 7 also illustrates one embodiment of a driver 152 that includes holes 710, or pockets, around the circumference of the driver 152. When the gap gauge 100 is used, a user may insert rods into the holes 710 to provide leverage for rotating the driver 152.

Figure 8A:
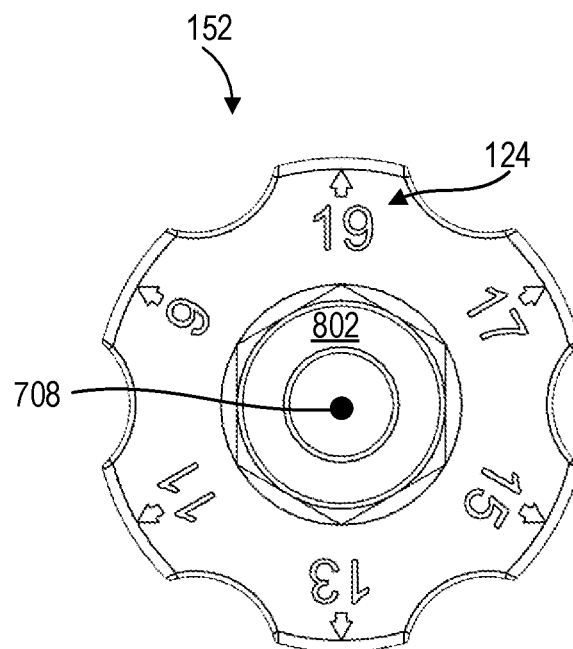
FIG. 8A is a front view of a driver of a gap gauge, according to one embodiment of the present disclosure.

FIG. 8A is a front view of a driver 152 of a gap gauge 100, according to one embodiment of the present disclosure. FIG. 8A illustrates the separation indicator 124, the driver 152, the central axis 708, and an opening 802. The opening 802 may be an area between an outer surface of the driver 152 and a head of the fastener 154. The opening 802 may have a polygonal cross-sectional shape. In the illustrated embodiment, the opening 802 is has a hexagon cross-sectional shape. The opening 802 may be sized and configured to receive a shaft or drive head of a separate tool such as a wrench (not shown). A user may use the wrench in the opening 802 to achieve a mechanical advantage in rotating the driver 152 about the central axis 708.

Figure 8B:
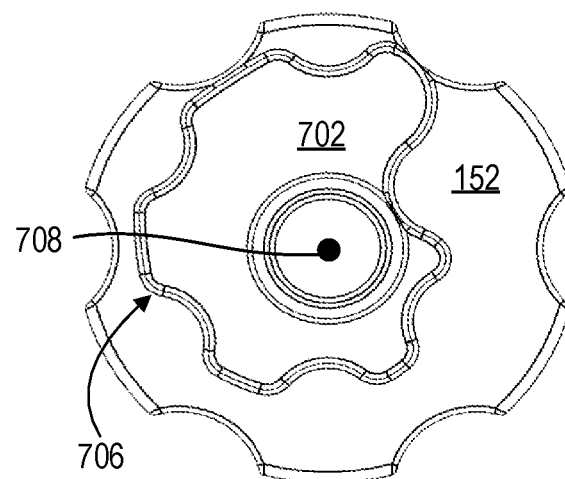
FIG. 8B is a rear view of a driver and cam of a gap gauge, according to one embodiment of the present disclosure.

FIG. 8B is a rear view of a driver 152 and cam 702 of a gap gauge 100, according to one embodiment of the present disclosure. FIG. 8B illustrates that the cam 702 may have an irregular radius that varies about the central axis 708. The length of the radius about the central axis 708 may be designed or engineered to achieve or maintain a desired displacement between the superior plate 118 and inferior plate 120 connected to the cam 702 and the follower 704.

Figure 9:
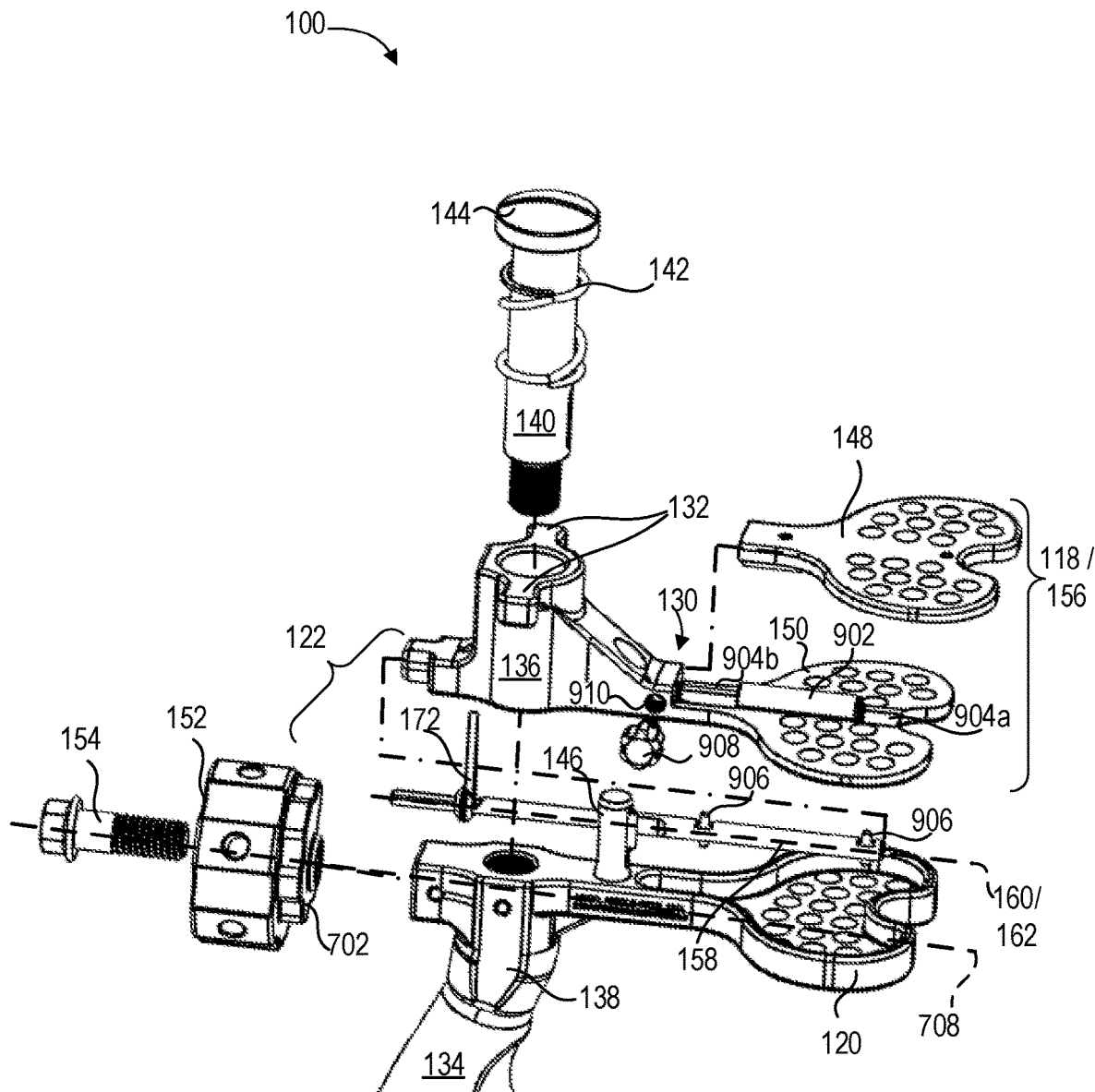
FIG. 9 illustrates an exploded view of a gap gauge, according to one embodiment of the present disclosure.

FIG. 9 illustrates an exploded view of an exemplary gap gauge 100, according to one embodiment of the present disclosure. FIG. 9 illustrates details about how the hinge 156, pin 158, and needle 172 can cooperate to provide a balance indicator 126. In certain embodiments, the balance indicator 126 includes a lock-out mechanism 130 that can prevent rotation of the pivot plate 148 relative to the inferior plate 120 and/or the support plate 150 when the lock-out mechanism 130 is in a set configuration.

FIG. 9 illustrates a support plate 150 that includes a knuckle 902 and openings 904a, 904b for at least one corresponding knuckle of the pivot plate 148. The knuckle 902 can connect the support plate 150 to the hinge 156 and the pivot plate 148. In such an embodiment, the support plate 150 and the pivot plate 148 can each serve as leaves of the hinge 156. When assembled, one or more knuckles of the pivot plate 148 align with one or more knuckles 902 of the support plate 150 and receive the pin 158. In this manner, the pivot plate 148, the pin 158, and the support plate 150 serve as a hinge to implement one embodiment of a balance indicator 126.

In certain embodiments, the pivot plate 148 may rotate freely about the pin 158. In such an embodiment, the pin 158 may include one or more pins 906. The pins 906 engage the pin 158 and the pivot plate 148 such that rotation of the pivot plate 148 causes rotation of the pin 158. In addition, if the pin 158 is fixed, or prevented from rotating about the pivot axis 162, the pins 906 may also retain the pivot plate 148 from rotating.

The pin 158 can extend within the superior body 136 and couple to the needle 172. In this manner, rotation of the pin 158 causes the needle 172 to move and point in a different direction. In certain embodiments, the pin 158 may pass through a slot in the post 146 to enable both rotation of the pin 158 and movement of the pin 158 away from the inferior body 138 when the gap gauge 100 is used.

FIG. 9 illustrates a lock-out mechanism 130 that can include a set screw 908. The set screw 908 has threads that engage with threads of an opening 910 in the superior body 136. Moving the set screw 908 into the opening 910 activates the lock-out mechanism 130 and prevents rotation of the pin 158 and connected pivot plate 148. Moving the set screw 908 out of the opening 910 deactivates the lock-out mechanism 130 and permits rotation of the pin 158 and connected pivot plate 148.

As used herein, a "set screw" refers to a type of screw generally used to secure a first object within, or against, second object, usually without using a nut. Set screws can be headless, meaning that the screw is fully threaded and has no head projecting past the thread's major diameter. If a set screw does have a head, the thread may extend to the head. A set screw can be driven by an internal-wrenching drive, such as a hex socket (Allen), star (Torx), square socket (Robertson), or a slot. A set screw can be driven by a knob on or part of a head of the set screw. The knob may be sized to facilitate rotation by a user using their fingers and may be referred to as a thumb screw. In one embodiment, the set screw passes through a threaded hole in the second object (an outer object) and is tightened against the first object (an inner object) to prevent the inner object from moving relative to the outer object. The set screw can exert a compressional and/or clamping force through an end of the set screw that projects through the threaded hole. (Search "set screw" on Wikipedia.com Aug. 17, 2020. Modified. Accessed Jan. 6, 2020.)

Figure 10A:
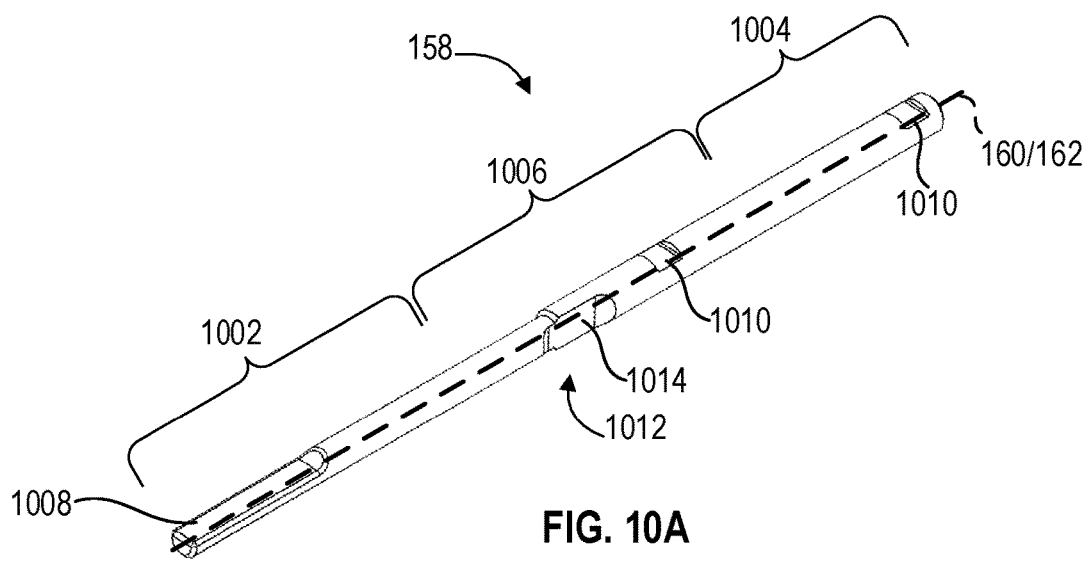
FIG. 10A is a perspective view of a pin of the gap gauge of FIG. 1A, according to one embodiment of the present disclosure.

FIG. 10A is a perspective view of a pin 158 of the gap gauge 100 of FIG. 1A, according to one embodiment of the present disclosure. The pin 158 may be a cylindrical structure with a longitudinal axis 160. The pin 158 can include a proximal end 1002, a distal end 1004, and a middle 1006. In one embodiment, the proximal end 1002 connects to a balance gauge 168. For example, the proximal end 1002 may include a D-shaped cross section that includes a flat part 1008. In one embodiment, the D-shaped cross-section of the proximal end 1002 may be sized to accept a D-shaped opening in a needle 172 that can be slide over the proximal end 1002 and positioned for a balance indicator 126 and/or a balance gauge 168.

The distal end 1004 may serve as a pivot for a hinge 156 of the gap gauge 100. Alternatively, or in addition, the distal end 1004 may serve as a pivot for the balance indicator 126. The pivot may align with the longitudinal axis 160. In addition, the distal end 1004 and/or the middle 1006 may include one or more keyed sections 1010. In one embodiment, the keyed sections 1010 may be used for the pins 906 to connect the pin 158 to the pivot plate 148.

In one embodiment, the middle 1006 may include a section 1012 that includes a planar surface 1014. The planar surface 1014 of the section 1012 may serve as part of the lock-out mechanism 130. For example in one embodiment, the set screw 908 may bias against the planar surface 1014 of the pin 158 to prevent rotation of the pin 158. In the illustrated embodiment, the section 1012 has a D-shaped cross-section. In one embodiment, the D-shaped cross-section of the section 1012 may be offset 90 degrees from a D-shaped cross-section of the proximal end 1002 that includes the flat part 1008. In one example embodiment, the 90-degree offset enables a needle 172 to register/measure no imbalance when the lock-out mechanism 130 is activated to prevent rotation of the pin 158.

Figure 10B:
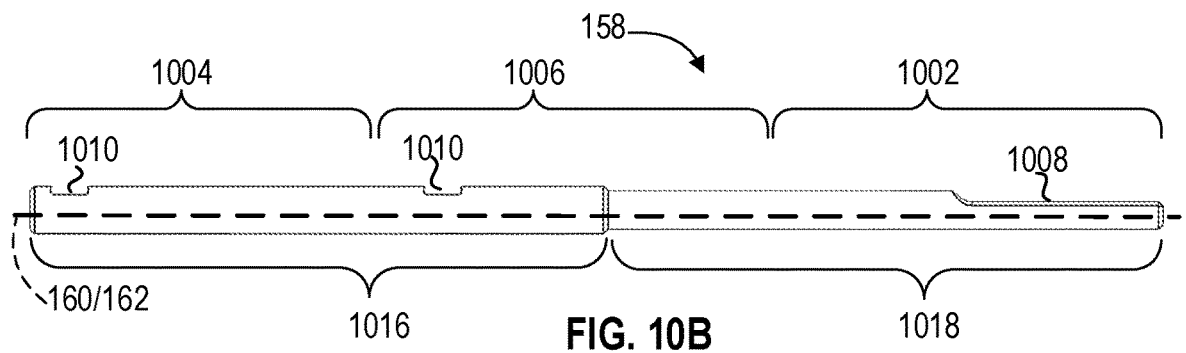
FIGS. 10B and 10C are side views of the pin of FIG. 10A, according to one embodiment of the present disclosure.
Figure 10C:
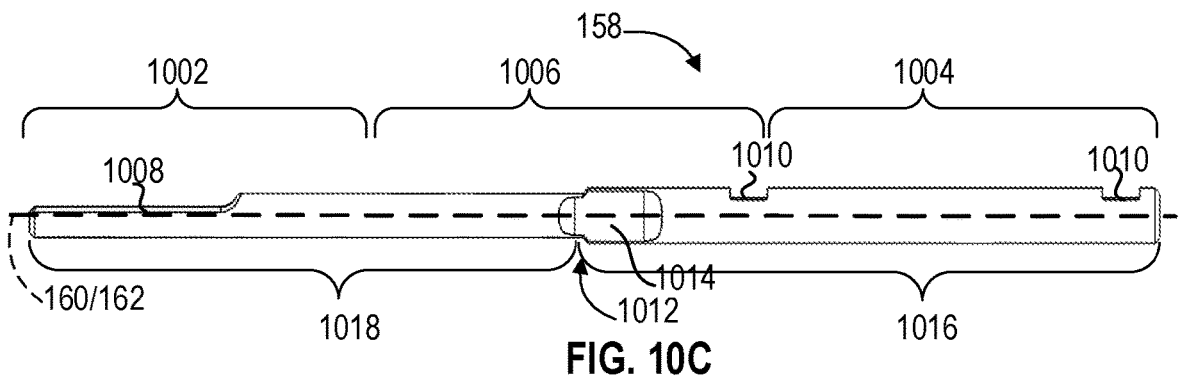

FIGS. 10B and 10C are side views of the pin 158 of FIG. 10A, according to one embodiment of the present disclosure. FIG. 10B illustrates and embodiment of a pin 158 that includes a first section 1016 having a larger diameter than a second section 1018.

Figure 11A:
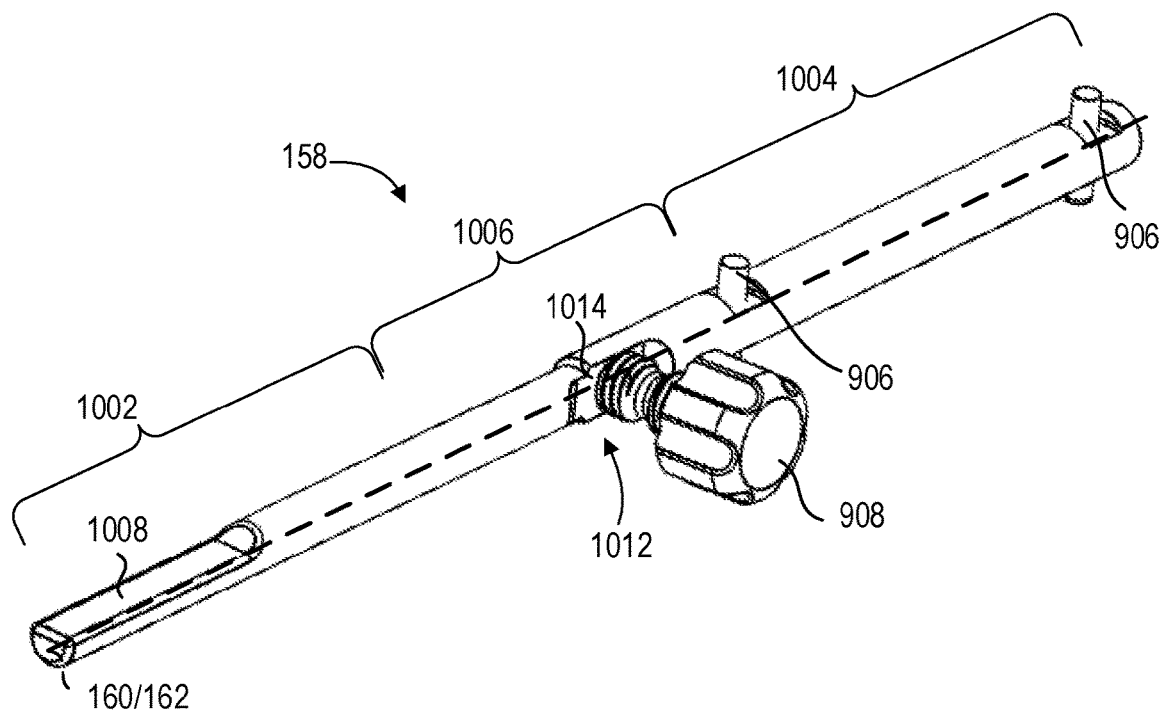
FIGS. 11A and 11B are perspective views of a lock-out mechanism of a gap gauge, according to one embodiment of the present disclosure.
Figure 11B:
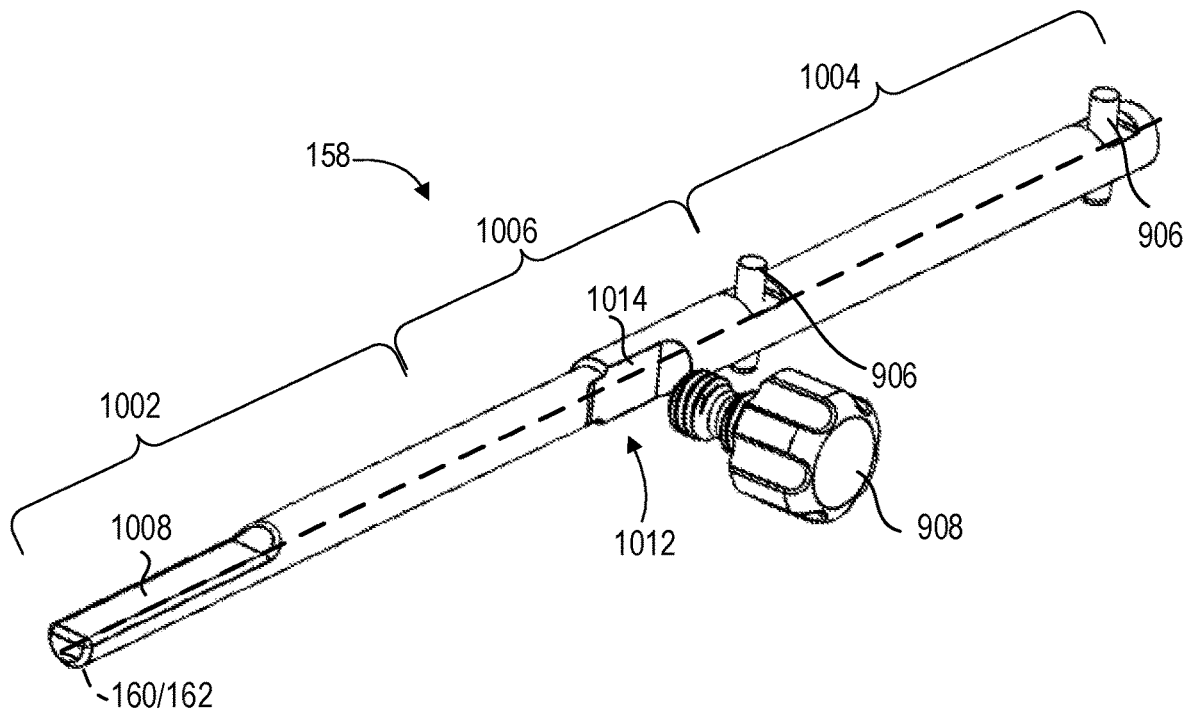

FIGS. 11A and 11B are perspective views of a lock-out mechanism 130 of a gap gauge 100, according to one embodiment of the present disclosure. FIG. 11A illustrates the lock-out mechanism 130 when the set screw 908 is in a set configuration. FIG. 11B illustrates the lock-out mechanism 130 when the set screw 908 is in an unset configuration. As used herein, a "set configuration" refers to an arrangement and/or relationship between a set screw and a pin such that the set screw prevents rotation of the pin about a longitudinal axis of the pin. In the set configuration, the set screw 908 has been advanced within the opening 910 to engage the planar surface 1014 of the section 1012.

As used herein, an "unset configuration" refers to an arrangement and/or relationship between a set screw and a pin such that the set screw permits rotation of the pin about a longitudinal axis of the pin. In the unset configuration, the set screw 908 has been retracted within the opening 910 to disengage the planar surface 1014 of the section 1012.

Figure 12:
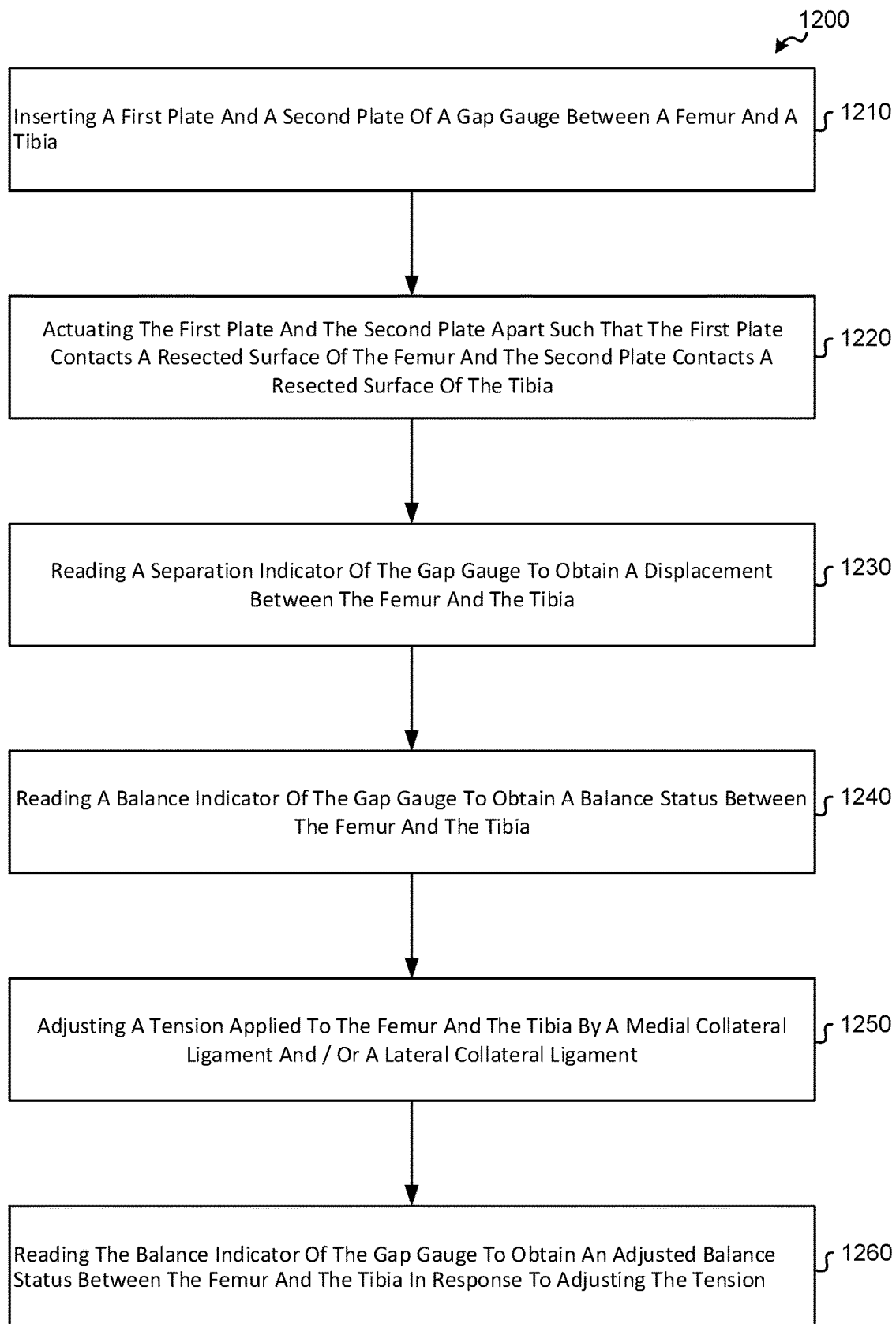
FIG. 12 illustrates a flowchart for measuring a gap and/or balance status between a femur and a tibia of a patient, according to one embodiment of the present disclosure.

FIG. 12 illustrates a flowchart for a method 1200 for measuring a gap and/or balance status between a femur and a tibia of a patient, according to one embodiment of the present disclosure. In general, the method 1200 may include the use of gap gauge that includes both a separation indicator and a balance indicator 126. In certain embodiments, the gap gauge may also include a balance gauge.

The method 1200 may begin with a step 1210 in which a first plate (e.g., inferior plate 120) and a second plate (e.g., superior plate 118) of a gap gauge may be inserted between a femur and a tibia. In certain embodiments, the gap gauge may be positioned such that a pivot axis of a hinge may be aligned with an anterior-posterior axis of a patient.

Once the gap gauge is positioned, the method 1200 may proceed to step 1220 in which the first plate and second plate are actuated apart such that the first plate contacts a resected surface of the femur and the second plate contacts a resected surface of the tibia.

Once the first plate and second plate have been actuated apart, the method 1200 may proceed to step 1230 in which a separation indicator of the gap gauge may be read to obtain a displacement between the femur and the tibia. Once the displacement has been read, the method 1200 may proceed to step 1240 in which a balance indicator of the gap gauge is read to obtain a balance status between the femur and the tibia.

A surgeon using the example gap gauge 100 may use the displacement amount and/or the balance status to choose from a set of prosthesis available for an arthroplasty procedure. In one example, a surgeon may choose a different prosthesis than one pre-operatively selected based on the balance status reported/measured by the balance indicator 126 and/or the example balance gauge 168. The different prosthesis may be selected to compensate for the balance status reported/measured by the balance indicator 126 and/or the example balance gauge 168. If a compensating prosthesis is selected, the surgeon may not need to make any changes to the joint 108 to accomplish a desired balance condition.

In another example, if the balance status indicates a varus condition, a first prosthesis may be selected during the procedure. If the balance status indicates a valgus condition, a second prosthesis may be selected during the procedure. Alternatively, or in addition, the displacement and/or balance status may be used by a surgeon to determine whether to do further resection of the femur 102 and/or tibia 104, whether to release one or more of the medial collateral ligament and the lateral collateral ligament, or take other steps of the arthroplasty procedure in an effort to accomplish a desired outcome for the arthroplasty procedure.

Once the displacement and the balance status has been read, the method 1200 may proceed to step 1250 in which tension applied to the femur and/or the tibia by a medial collateral ligament and/or a lateral collateral ligament is adjusted. Once the tension applied to the femur and/or the tibia is adjusted, the method 1200 may proceed to step 1260 in which the balance indicator of the gap gauge is read to obtain an adjusted balance status between the femur and the tibia in response to adjusting the tension. After reading the adjusted balance, the method 1200 may end with the balance of the joint having the desired balance status.

Alternatively, or in addition thereto, the method 1200 may proceed to a step in which a tension applied to the femur and the tibia by one or more of a medial collateral ligament and a lateral collateral ligament may be adjusted and the balance indicator of the gap gauge may be read to obtain an adjusted balance status between the femur and the tibia in response to adjusting the tension.

Alternatively, or in addition thereto, once tension applied to the femur and the tibia by one or more of a medial collateral ligament and a lateral collateral ligament is adjusted, the method 1200 may proceed to a step in which one or more of the medial collateral ligament and the lateral collateral ligament are released while the gap gauge remains between the femur and the tibia and remains actuated.

Alternatively, or in addition thereto, once tension applied to the femur and the tibia by one or more of a medial collateral ligament and a lateral collateral ligament is adjusted, the method 1200 may proceed to a step in which the gap gauge is removed from between the femur and the tibia. Once the gap gauge is removed from between the femur and the tibia, the method 1200 may proceed to a step in which one or more of the resected surface of the femur and the resected surface of the tibia is resected. Once one or more of the resected surface of the femur and the resected surface of the tibia are resected, the method 1200 may proceed to a step in which the first plate and the second plate of the gap gauge is re-inserted between the femur and the tibia. Once the first plate and the second plate of the gap gauge is re-inserted between the femur and the tibia, the method 1200 may proceed to a step in which the first plate and the second plate are actuated apart such that the first plate is in contact with the resected surface, or further resected surface, of the femur and the second plate is in contact with the resected surface, or further resected surface, of the tibia. Once the first plate and second plate are actuated apart, the method 1200 may proceed to a step in which the separation indicator of the gap gauge is read to obtain the displacement between the femur and the tibia. Once the displacement is obtained, the method 1200 may proceed to a step in which the balance indicator of the gap gauge is read to obtain the balance status between the femur and the tibia.

Figure 13:
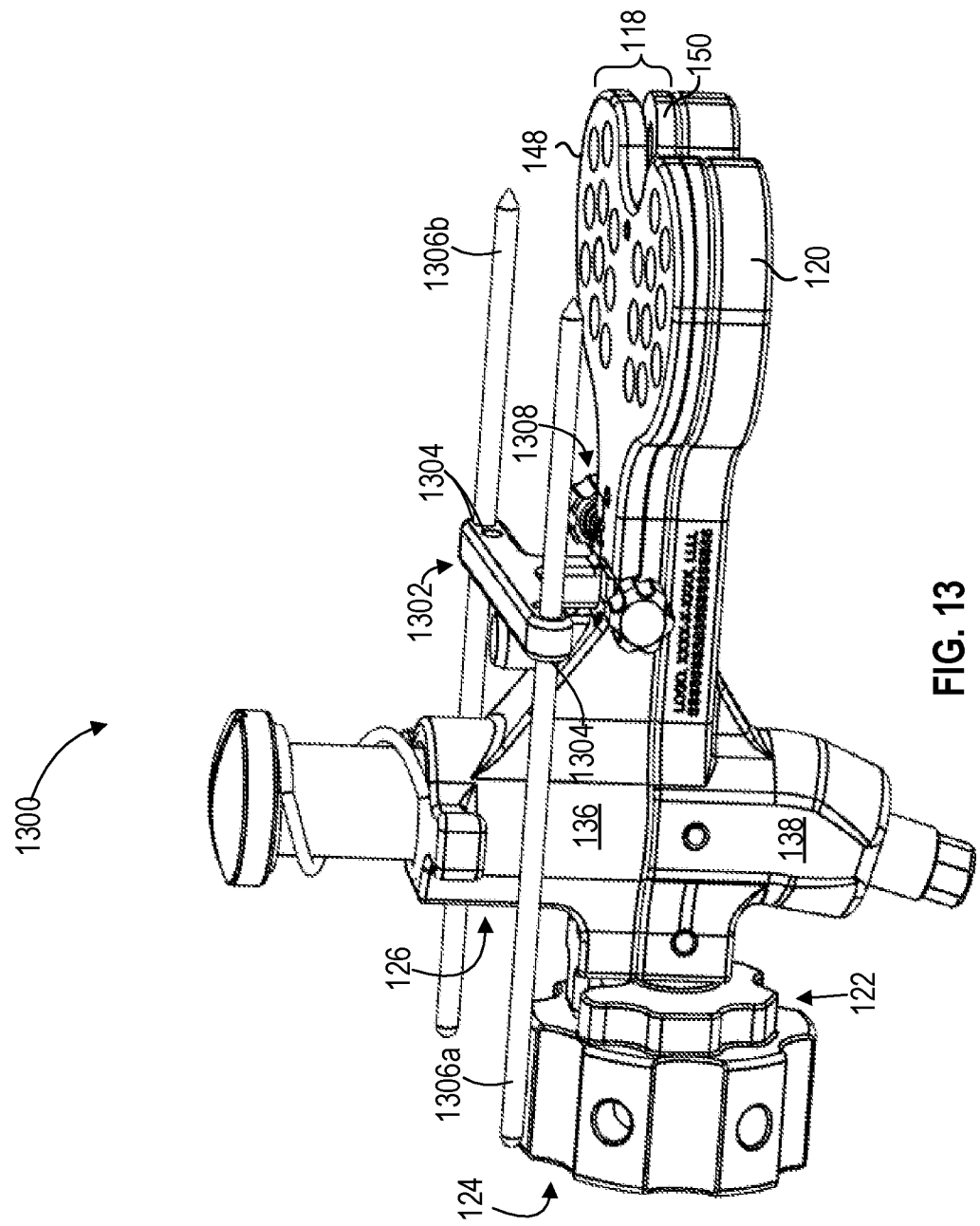
FIG. 13 is a perspective view of a gap gauge, according to one embodiment of the present disclosure.

FIG. 13 is a perspective view of an exemplary gap gauge 1300, according to one embodiment of the present disclosure. In one embodiment, the exemplary gap gauge 1300 may generally include a first plate and a second plate. In the illustrated embodiment, the first plate may be an inferior plate 120 and the second plate may be a superior plate 118. The superior plate 118 may include a pivot plate 148 and a support plate 150. The first plate 120 can be positioned in contact with a first bone, such as a tibia and the second plate 118 can be positioned in contact with a second bone, such as a femur. In one embodiment, the first plate and the second plate are sized for insertion between a first bone that is a tibia and a second bone that is a femur. The superior plate 118, inferior plate 120, pivot plate 148, and support plate 150 may be similar in structure, performance, and/or operation to like numbered components in other embodiments previously described.

The exemplary gap gauge 1300 may also generally include a separator 122, a separation indicator 124, a balance indicator 126, a handle 134 (not shown in FIG. 13), a superior body 136, and an inferior body 138 similar in structure, performance, and/or operation to like numbered components in other embodiments previously described.

In one embodiment, the exemplary gap gauge 1300 includes a pin guide 1302. As used herein, a "guide" refers to a part, component, or structure designed, adapted, configured, or engineered to guide or direct one or more other parts, components, or structures. A guide may be part of, integrated with, connected to, attachable to, or coupled to, another structure. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" that guides or directs the making or one or more cuts, and the like.

The pin guide 1302 can be connected and/or connectable to one of the second plate (e.g. superior plate 118) and the first plate (e.g. an inferior plate 120). The pin guide 1302 can include at least one pin hole 1304. Each pin hole 1304 may be configured to receive a pin 1306. A first pin hole can be positioned, sized, and configured to guide the insertion of a first pin 1306a into a bone (e.g., a femur 102). In one embodiment, the pin guide 1302 includes an attachment feature 1308. The attachment feature 1308 enables the exemplary gap gauge 1300 to have the pin guide 1302 attached or detached as desired or needed.

As used herein, a "pin hole" refers to a hole, void, opening, channel, space, or passage that extends from one side of a structure to another side of the structure. In certain embodiments, a pin hole is straight. A pin hole may have a circular or oval cross section. In certain embodiments, a pin hole is configured to accept a pin. A diameter of a pin hole may be just larger than a cross-sectional diameter of a pin such that the pin fits within the pin hole in a friction fit or a loose fit. In certain embodiments, a pin hole can include a beveled or chamfered edge at one or both openings of the pin hole. A pin hole may serve to accept alignment pins, attachment pins, securement pins or the like. Pins within the pin hole may sit within the pin hole temporarily during a procedure or permanently as part of procedures. Pin holes can be used in a variety of devices, components, apparatus, and systems, including but not limited to, fixation plates, measurement instruments, pin guides, cutting guides, and the like.

As used herein, an "pin" refers to an elongated structure. In certain embodiments, a pin can be configured to support a load (including a tension, compression, shear, torsion, and/or bending load). In certain embodiments, a pin may be a thin cylindrical structure. A pin can serve a variety of functions and may include a modifier identifying a particular function for example certain solutions may use alignment pins, attachment pins, securement pins, or the like. Pins may serve a temporary or permanent structural purpose. Pins can be used in a variety of devices, components, apparatus, and systems, including but not limited to, fixation plates, measurement instruments, pin guides, cutting guides, surgical instrumentation, and the like. A pin can have a variety of geometric cross-sectional shapes, including, but not limited to a circle, an ellipse, an ovoid, or other circular or semicircular shape, as well as a rectangle, a square, or other polygon. A pin has two ends one end can be blunt and the other end may come to a point. A pin can be made from a variety of materials including, metal, plastic, ceramic, wood, fiberglass, or the like. A pin may also be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others.

As used herein, "feature" refers to a distinctive attribute or aspect of something. (Search "feature" on google.com. Oxford Languages, 2021. Web. 20 Apr. 2021.) A feature may include a modifier that identifies a particular function or operation and/or a particular structure relating to the feature. Examples of such modifiers applied to a feature, include, but are not limited to, "attachment feature," "securing feature," "alignment feature," "adjustment feature," "guide feature," "protruding feature," "engagement feature," "disengagement feature," and the like.

In the illustrated embodiment, the pin guide 1302 includes two pin holes 1304 each configured to guide a pin 1306a,b into a bone (e.g., a femur 102). In certain embodiments, the pins 1306 may be parts of an exemplary gap gauge 1300. Alternatively, or in addition, the pins 1306 may be part of a kit or assembly such as a gap measurement and correction assembly for facilitating an arthroplasty procedure on a femur and a tibia of a patient. In certain embodiments, the gap measurement and correction assembly may also include a cutting guide.

As used herein, an "assembly" refers to a collection, set, or kit of two or more structures, components, parts, systems, and/or sub-systems that together may be used, connected, coupled, applied, integrated, or adapted to be used to perform one or more functions and/or features. An assembly may include a modifier that identifies one or more particular functions or operations that can be accomplished using the assembly. Examples of such modifiers applied to an assembly, include, but are not limited to, "measurement assembly," "correction assembly," "fixation assembly," "separation assembly," "cutting assembly," and the like.

In one embodiment, the proposed solution is a gap measurement and correction assembly for facilitating an arthroplasty procedure on a femur and a tibia of a patient. The assembly may include an exemplary gap gauge 1300, a cutting guide and optionally one or more pins 1306. The exemplary gap gauge 1300 may include a superior plate 118, inferior plate 120, separator 122, a balance indicator 126, and a pin guide 1302. The balance indicator 126 connects to one of the superior plate and the inferior plate and indicates a nonparallel orientation of the superior plate 118 relative to the inferior plate 120. As used herein, "orientation" refers to a direction, angle, position, condition, state, or configuration of a first object, component, part, apparatus, system, or assembly relative to another object, component, part, apparatus, system, or assembly. As used herein, "nonparallel orientation" refers to two structures that are oriented in a nonparallel configuration with respect to each other.

In one embodiment, a pin guide 1302 of an assembly guides insertion of a first pin into either one of a tibia and a femur of a patient. The first pin 1306a and/or a second pin 1306b can be used to attach, or connect, a cutting guide to one of the tibia and the femur. The cutting guide is designed to guide resection of the tibia or the femur having the inserted pin(s) 1306a,b. In one embodiment, the cutting guide is configured to counter a nonparallel orientation of the superior plate 118 relative to the inferior plate 120. Alternatively, or in addition, the pin guide 1302 may be configured to counter a nonparallel orientation of the superior plate 118 relative to the inferior plate 120.

FIGS. 14A-14D illustrate are a rear view, perspective side views, and a front perspective view, respectively of the pin guide 1302 of FIG. 13, according to one embodiment of the present disclosure. An exemplary gap gauge 1300 may include a variety of designs for a pin guide 1302 that is coupled or connected to the exemplary gap gauge 1300.

In one embodiment, the pin guide 1302 includes a base 1310, an arm 1312, and a mast 1314. The base 1310, arm 1312, and/or mast 1314 cooperate to position one or more pin holes 1304 for pins 1306 used in an arthroplasty procedure.

The base 1310 serves as a structural connection for the pin guide 1302 to the exemplary gap gauge 1300. As used herein, a "base" refers to a main or central structure, component, or part of a structure. A base is often a structure, component, or part upon which, or from which other structures extend, are coupled to, or connect to. A base may have a variety of geometric shapes and configurations. A base may be rigid or pliable. A base may be solid or hollow. In one embodiment, a base may include a housing, frame, or framework for a larger system, component, structure, or device.

In one embodiment, the base 1310 is shaped, sized, and designed to connect the pin guide 1302 to a second plate, such as a superior plate 118. For example, in one embodiment, the base 1310 includes an arcuate section that can facilitate mating the base 1310 to a section of a second plate, such as a superior plate 118.

The arm 1312 includes one or more pin holes 1304. In one embodiment, the pin holes 1304 are parallel with each other. As used herein, an "arm" refers to an elongated structure that extends from another structure such as a base or a body. In certain embodiments, an arm can be configured to support a load (including a tension, compression, shear, torsion, and/or bending load). In certain embodiments, an arm may comprise a generally planar structure. An arm can be a separate structure connected to, or integrated with, another structure. Based on how the arm connects to or extends from another structure, such as a base or body, the arm can resemble an arm of a human or animal in that the arm can be an appendage to another structure. An arm can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. An arm can be made from a variety of materials including, metal, plastic, ceramic, wood, fiberglass, or the like. One arm may be distinguished from another based on where the arm is positioned within a structure, component, or apparatus.

The mast 1314 extends from the base 1310 and connects the base 1310 and the arm 1312. As used herein, a "mast" refers to an elongated structure that extends from another structure such as a base or a body. In certain embodiments, a mast can be configured to support one or more other structures that connect to or extend from the mast. A mast can be configured to support a load (including a tension, compression, shear, torsion, and/or bending load). In certain embodiments, a mast may comprise a cylindrical structure. A mast can be a separate structure connected to, or integrated with, another structure. A mast can have a variety of geometric shapes and/or cross-sectional shapes, including, but not limited to a rectangle, a square, or other polygon, as well as a circle, an ellipse, an ovoid, or other circular or semi-circular shape. A mast can be made from a variety of materials including, metal, plastic, ceramic, wood, fiberglass, or the like.

In one embodiment, the mast 1314 can extend in a superior direction when the exemplary gap gauge 1300 is being used on a patient's knee. Alternatively, the mast 1314 can extend in an inferior direction when the exemplary gap gauge 1300 is being used on a patient's knee. The direction and manner that the mast 1314 extends may be determined by how the mast 1314 connects to the base 1310 and/or how the base 1310 connects to one or more plates of an exemplary gap gauge 1300.

The arm 1312 can include a first segment 1316 and a second segment 1318. In one embodiment, the first segment 1316 is a different length than the second segment 1318. Alternatively, the first segment 1316 and second segment 1318 can be substantially the same length. In the illustrated embodiment, the first segment 1316 includes two pin holes 1304 and the second segment 1318 includes two pin holes 1304. Those of skill in the art recognize that the first segment 1316 and second segment 1318 can have various numbers of pin holes 1304. In one embodiment, the exemplary gap gauge 1300 is configured for use on either a left knee or a right knee. Consequently, depending on the knee being used the first segment 1316 may extend in a medial direction from the mast 1314, and thus a medial side of a knee, or a lateral direction from the mast 1314, and thus a medial side of a knee when the exemplary gap gauge 1300 is placed within a gap between a femur and a tibia.

The pin holes 1304 can be used in a variety of ways for different arthroplasty procedures. For example, a first pin hole 1304*a* within a first segment 1316 and a second pin hole 1304*b* in a second segment 1318 may be used to position and place pins 1306 for a particular arthroplasty procedure. When the exemplary gap gauge 1300 is positioned anterior to a left knee the first segment 1316 may extend toward the medial side of the knee and the second segment 1318 may extend toward the lateral side of the knee. Of course, the sides may be reversed when the exemplary gap gauge 1300 is used on a right knee.

In such an example, the first pin hole 1304*a* and second pin hole 1304*b* may serve to position pins 1306 within a bone, such as a femur or a tibia. In one embodiment, first pin hole 1304*a* and second pin hole 1304*b* position pins 1306 within a femur (e.g., a second bone) in a manner that conveys, or communicates, a balance status of a knee by way of placement of the pins 1306. In one embodiment, the pin guide 1302, first pin hole 1304*a*, and second pin hole 1304*b* cooperate to align a first pin 1306*a* and a second pin 1306*b* with each other at an orientation relative to second plate (e.g., a superior plate 118 connected to the pin guide 1302) that matches the balance status of the knee. In this manner, the balance status can be transferred from the exemplary gap gauge 1300 to one of the bones, such as a femur.

Placement of the first pin 1306*a* and a second pin 1306*b* in one of the bones, such as a femur, enables coupling of a cutting guide to a bone, such as a femur. For example, holes in the cutting guide may permit the cutting guide to slide over the pins 1304*a,b* and contact the bone (e.g., femur). In this manner, the first pin 1306*a* and a second pin 1306*b* communicate a balance status from the exemplary gap gauge 1300 to the cutting guide.

Other pin holes, such as a third pin hole 1304*c* and/or a fourth pin hole 1304*d* may be used in the same arthroplasty procedure on the same patient. For example, third pin hole 1304*c* and/or a fourth pin hole 1304*d* may serve as alternative or additional pin placement locations in situations where a bone does not securely engage a pin due to conditions like osteoporosis. In another example, third pin hole 1304*c* and/or a fourth pin hole 1304*d* may serve as pin placement locations for patients of different ages or genders.

Figure 14A:
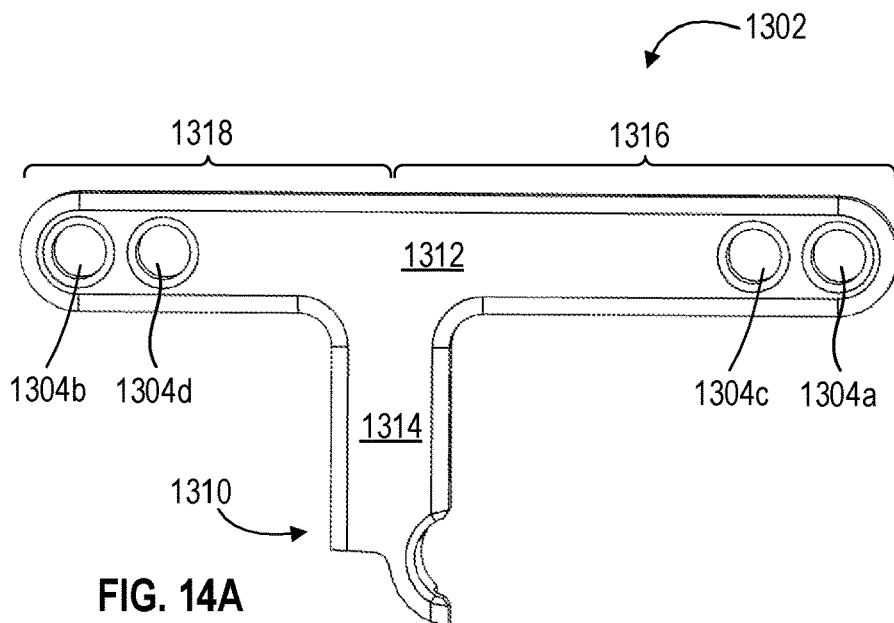
FIGS. 14A-14D are a rear view, perspective side views, and a front perspective view, respectively of the pin guide of FIG. 13, according to one embodiment of the present disclosure.
Figure 14B:
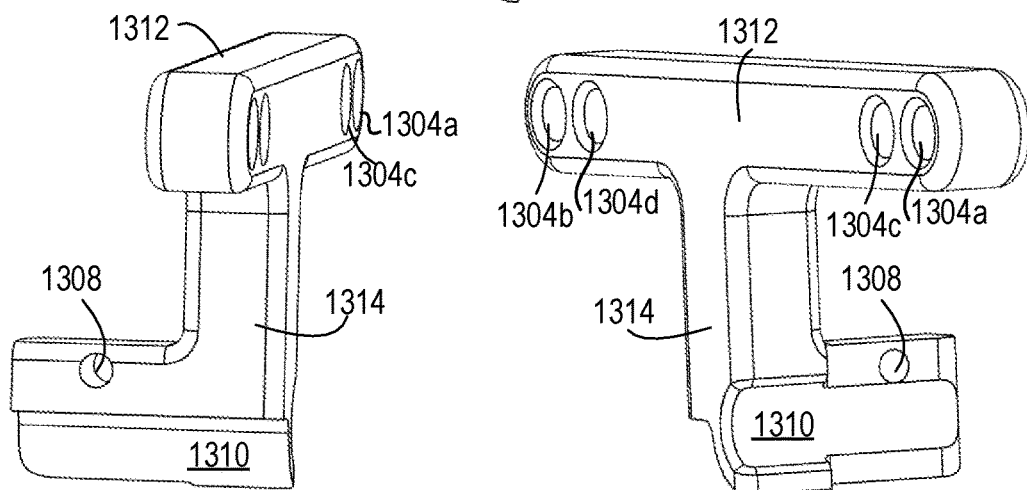
Figure 14C:
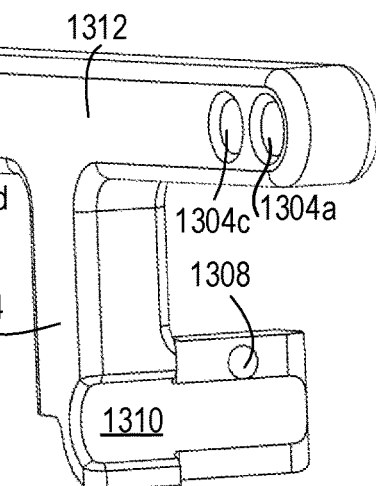

FIGS. 14B and 14C illustrate perspective side views of a pin guide 1302 in accordance with one embodiment. In one embodiment, the pin guide 1302 can be connected to a plate (e.g., superior plate 118, inferior plate 120, pivot plate 148, and/or support plate 150). For example, an attachment feature 1308 may include a hole in the base 1310 and a corresponding hole in a plate and a pin that can be inserted into both holes to secure the pin guide 1302 to the plate. Alternatively, or in addition, the attachment feature 1308 may enable the pin guide 1302 can be removably coupled to the exemplary gap gauge 1300.

Figure 14D:
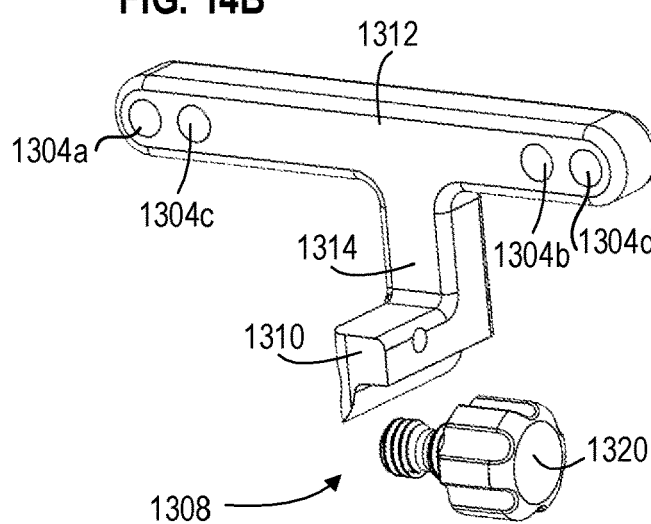

Referring now to FIG. 14D, for example, the pin guide 1302 may include an attachment feature 1308 that enables the pin guide 1302 to be removably coupled to one or more of the plates of an exemplary gap gauge 1300 (e.g., superior plate 118, inferior plate 120, pivot plate 148, and/or support plate 150). The attachment feature 1308 may include a hole in the base 1310 and a hole in a plate. The holes may include internal threads configured to engage external threads of a set screw 1320. The set screw 1320 may be similar to the screw 908 described earlier. Rather than contacting a pin, the set screw 1320 may engage a threaded hole in the plate to removably couple the pin guide to the plate.

Those of skill in the art will appreciate that the pin guide 1302 can be coupled or connected to different plates of the exemplary gap gauge 1300 and may extend from the exemplary gap gauge 1300 in a superior direction or an inferior direction when the exemplary gap gauge 1300 is in use.

In the illustrated embodiment, of FIG. 14D, the attachment feature 1308 removably couples the pin guide 1302 to a second plate, a superior plate 118, such that the pin guide 1302 guides insertion of a first pin 1306a (through first pin hole 1304a) into a second bone, such as a femur 102 such that the first pin 1306a is placed in the femur 102 according to the balance status between a first plate, an inferior plate 120, and the second plate, the superior plate 118. In such an embodiment, the pin guide 1302 may extend in a superior direction when the exemplary gap gauge 1300 is in use.

Specifically, the first pin 1306a can be placed in the femur 102 at a location that reflects the balance or imbalance of a gap in the knee. Because the pin guide 1302 is connected to the superior plate 118, and the superior plate 118 can pivot using the hinge 156, the pin can be placed in a position that reflects the balance, or imbalance, of the gap. Furthermore, a pin guide 1302 that includes a second pin hole 1304b for placement of a second pin 1306b, enable the placement of a first pin 1306a and a second pin 1306b parallel to each other in an orientation and/or relationship that reflects the balance status of the gap. Such orientation and/or relationship can be referred to as a nonparallel orientation.

As used herein, "imbalance" refers to a state or condition in which two opposing factors, features, attributes, aspects, conditions, or states are not balanced. "Imbalance" also refers to a lack of proportion or relation between corresponding things, structures, components, angles, or vectors. (Search "imbalance" on google.com. Oxford Languages, 2021. Modified. Web. 26 May 2021.) Examples of opposing factors, features, attributes, aspects, conditions, or states that can be imbalanced includes a varus condition and a valgus condition, a motive force and a friction force, and the like.

In another embodiment, the attachment feature 1308 may removably couple the pin guide 1302 to a second plate, a superior plate 118, such that the pin guide 1302 guides insertion of a first pin 1306a (through first pin hole 1304a) into a first bone, such as a tibia 104 such that the first pin 1306a is placed in the tibia 104 according to the balance status between a first plate, an inferior plate 120, and the second plate, the superior plate 118. In such an embodiment, the pin guide 1302 may extend in an inferior direction when the exemplary gap gauge 1300 is in use.

Specifically, the first pin 1306a can be placed in the tibia 104 at a location that reflects the balance, or imbalance, of a gap in the knee. Because the pin guide 1302 is connected to the superior plate 118, and the superior plate 118 can pivot using the hinge 156, the pin can be placed in a position that reflects the balance, or imbalance, of the gap. Furthermore, a pin guide 1302 that includes a second pin hole 1304b for placement of a second pin 1306b, enable the placement of a first pin 1306a and a second pin 1306b parallel to each other in an orientation and/or relationship that reflects the balance status of the gap. Such orientation and/or relationship can be referred to as a nonparallel orientation.

Figure 15:
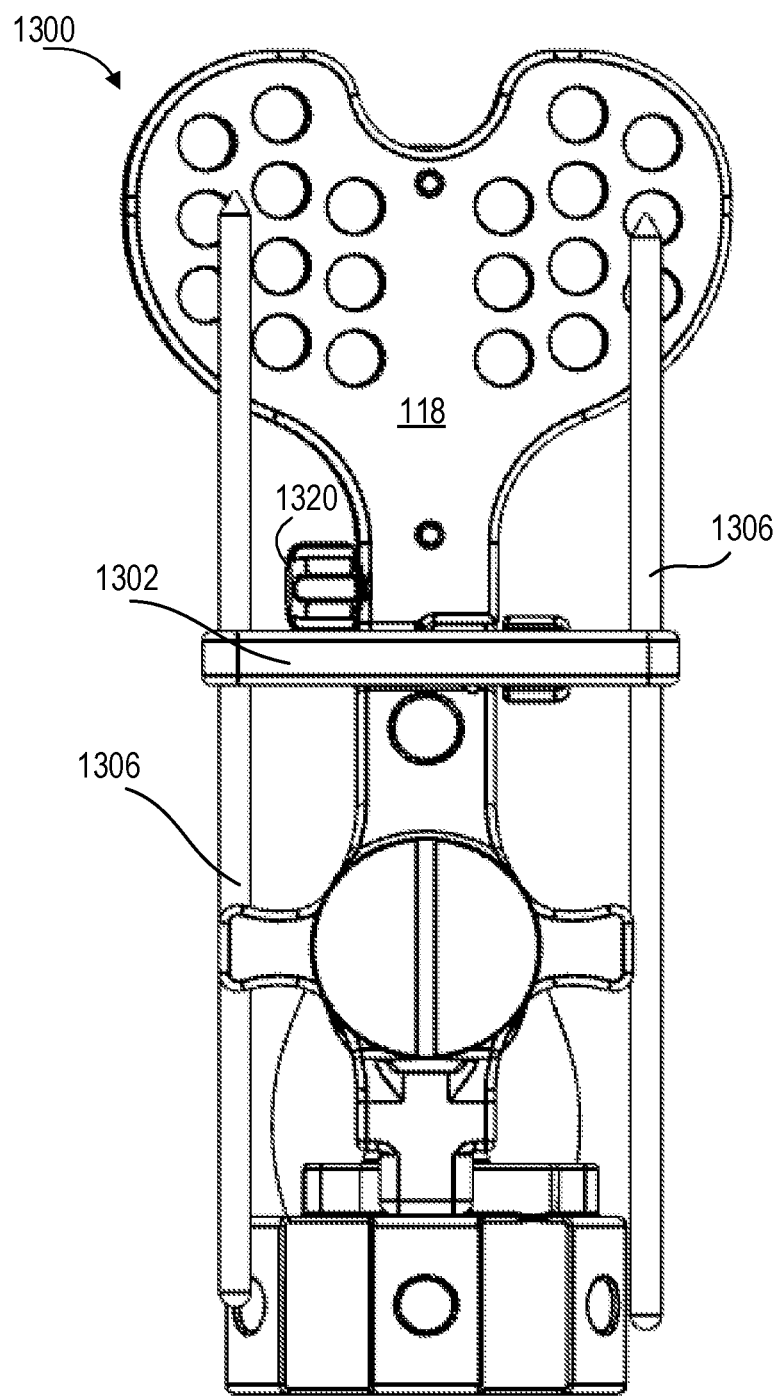
FIG. 15 is a top view of a gap gauge of FIG. 13, according to one embodiment of the present disclosure.

FIG. 15 is a top view of an exemplary gap gauge 1300 of FIG. 13, according to one embodiment of the present disclosure. The exemplary gap gauge 1300 includes a pin guide 1302 with two pins 1306 passing through corresponding pin holes in the pin guide 1302. In certain embodiments, the two pins 1306 may be long enough to facilitate securing them in one of a femur 102 and a tibia 104. In the illustrated embodiment, the pin guide 1302 can be connected to the superior plate 118 and extend above the superior plate 118 to position the pins 1306 in a femur 102. Alternatively, the pin guide 1302 can be connected to the superior plate 118 and extend below the superior plate 118 and inferior plate 120 to position the pins 1306 in a tibia 104.

FIG. 15 also illustrates an attachment feature 1308 embodied using a set screw 1320 and corresponding threaded holes that can connect the pin guide 1302 to one or more of the plates. In various embodiments, the set screw 1320 can connect the pin guide 1302 to a superior plate 118, such as a pivot plate 148 and/or support plate 150 or to an inferior plate 120.

Figure 16A:
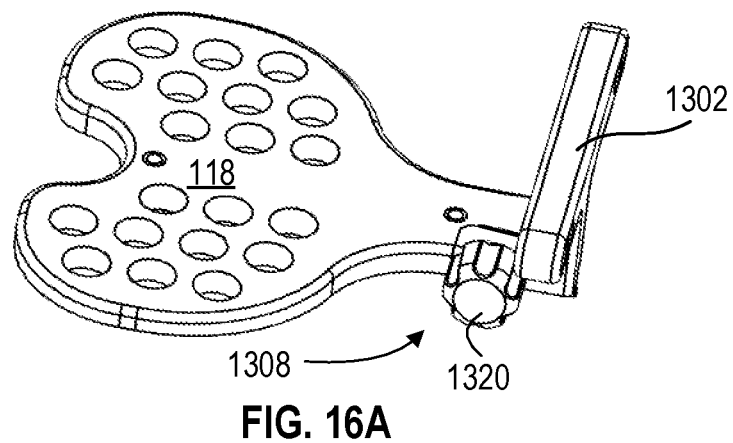
FIGS. 16A and 16B are side perspective views of a pin guide of FIG. 13, according to one embodiment of the present disclosure.
Figure 16B:
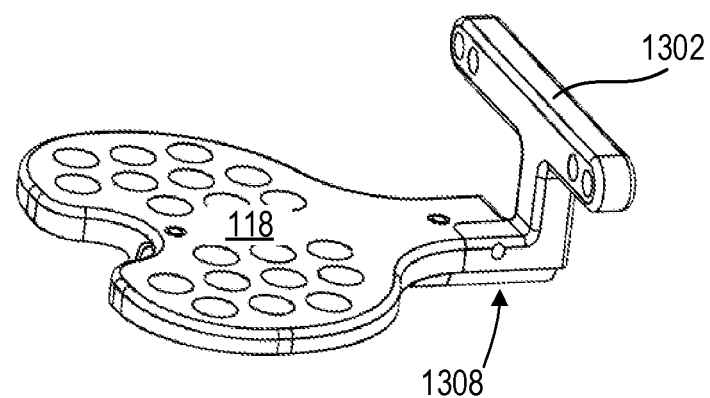

FIGS. 16A and 16B are side perspective views of a pin guide 1302 of FIG. 13, according to embodiments of the present disclosure. FIGS. 16A and 16B illustrate two alternative embodiments of an attachment feature 1308 that can be used. In FIG. 16A, an attachment feature 1308 embodied as a set screw 1320 can be used to removably couple the pin guide 1302 to a second plate, such as superior plate 118, such that the pin guide guides insertion of one or more pins into a bone according to a balance status between a first plate and a second plate. In FIG. 16B, an attachment feature 1308 embodied as a pin and corresponding hole(s) can be used to couple the pin guide 1302 to a second plate, such as superior plate 118, such that the pin guide guides insertion of one or more pins into a bone according to a balance status between a first plate and a second plate.

FIGS. 16A and 16B also illustrate how a base 1310 of a pin guide 1302 can be configured to interface with an opening in a plate as the pin guide 1302 couples to the plate. For example, the base 1310 may be shaped to fit within a corresponding opening in a superior plate 118.

Figure 17A:
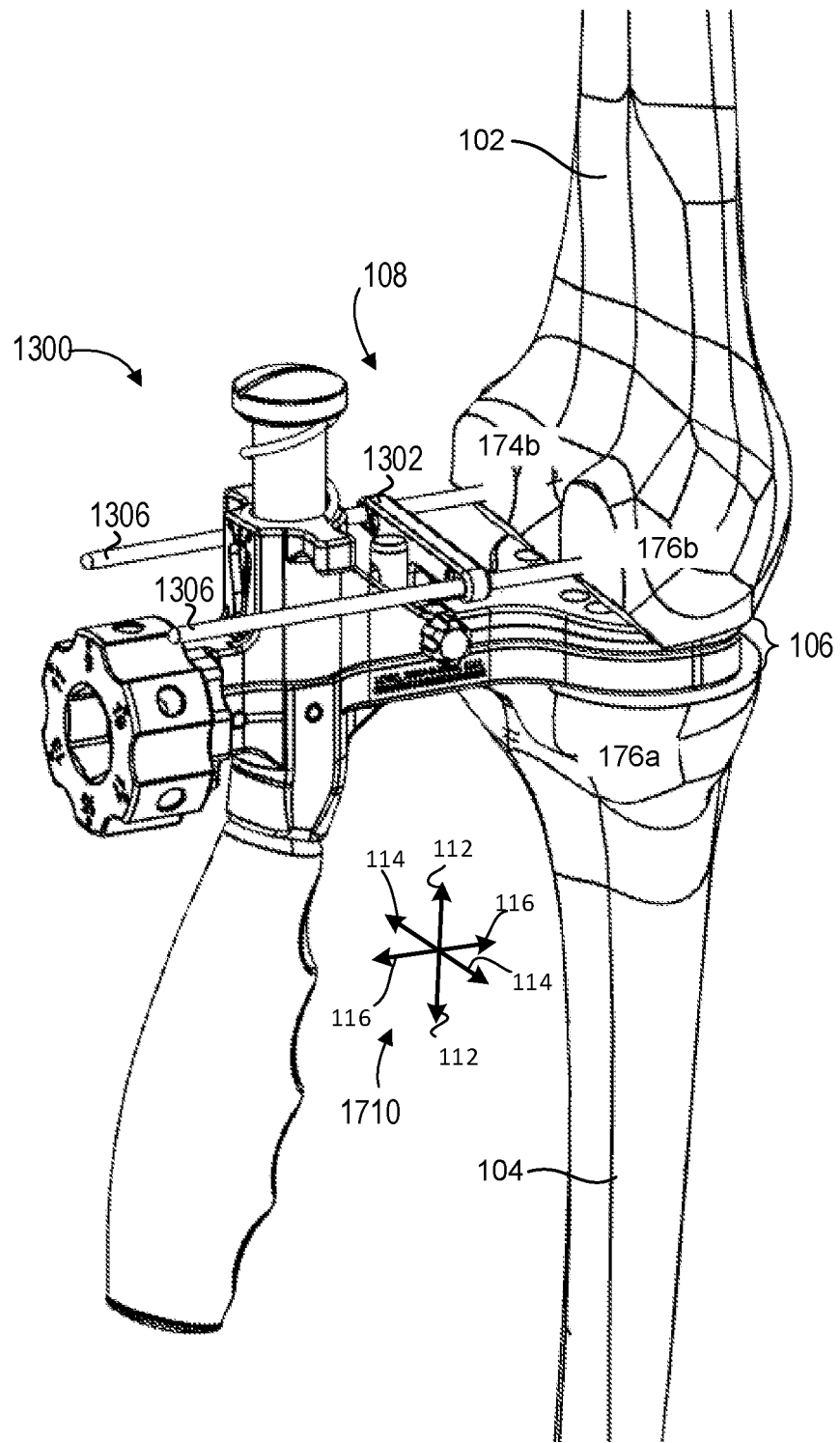
FIG. 17A is a perspective view of a gap gauge inserted between two bones, according to one embodiment of the present disclosure.
Figure 17B:
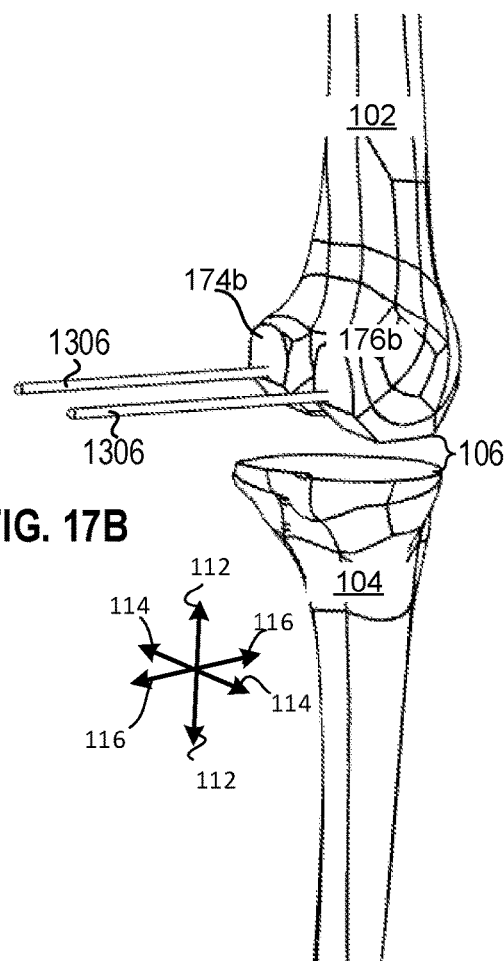
FIG. 17B is a perspective view of two pins in one of the bones of FIG. 17A, according to one embodiment of the present disclosure.
Figure 17C:
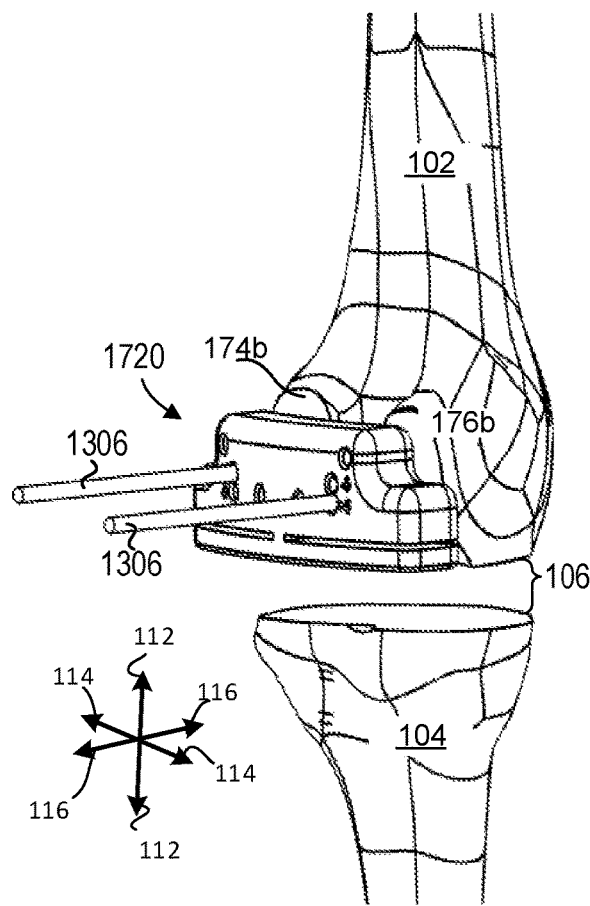
FIG. 17C is a perspective view of a cutting guide engaging the two pins in one of the bones of FIG. 17A, according to one embodiment of the present disclosure.
Figure 17D:
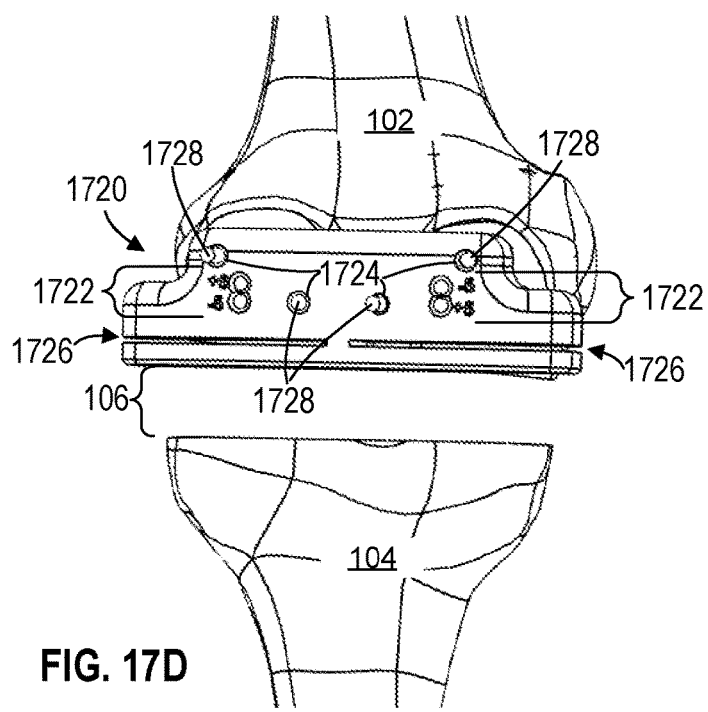
FIG. 17D is a front perspective view of the cutting guide secured to one of the bones of FIG. 17A, according to one embodiment of the present disclosure.

FIG. 17A is a perspective view of a gap gauge 1300 inserted between two bones, according to one embodiment of the present disclosure. FIG. 17A illustrates one stage of one possible arthroplasty procedure according to one embodiment of the present disclosure. FIGS. 17B-17D illustrate subsequent exemplary stages of a possible arthroplasty procedure according to one embodiment of the present disclosure.

FIG. 17A illustrates a three-dimensional axis 1710. The three-dimensional axis 1710 includes a cephalad-caudal axis 112, a medial-lateral axis 114, and an anterior-posterior axis 116 as described above. The three-dimensional axis 110 is used to identify how a gap gauge 1300 is positioned and/or oriented with respect to an anterior-posterior axis 116 and cephalad-caudal axis 112 of a patient who is in a reference anatomical position.

FIG. 17A illustrates a posterior perspective view of a knee joint 108 in extension, such as a left knee. The exemplary gap gauge 1300 can be inserted into an opening 106 by moving the exemplary gap gauge 1300 along the anterior-posterior axis 116. Once inserted, the exemplary gap gauge 1300 may be actuated to measure a size of the opening 106. The exemplary gap gauge 1300 may be actuated by engaging the superior plate 118 with a resected surface of a femur 102 and the inferior plate 120 with a resected surface of a tibia 104. In one embodiment, the inferior plate 120 is a first plate and the superior plate 118 is a second plate. The first plate and the second plate may be sized for insertion between the first bone which may be a tibia and the second bone which may be a femur. With the superior plate 118 and inferior plate 120 engaging the bones, an operator can determine a balance status by examining a balance indicator 126.

At this stage in a procedure, a surgeon can determine whether further resection of one, or the other, or both of the bones is desired. If resection is desired, an operator may pass, or insert, pins 1306 through the pin holes 1304 and into one of a medial condyle and a lateral condyle of the bone. In the illustrated embodiment, the operator may pass one pin 1306 through the pin guide 1302 and into a lateral condyle 176b of the femur 102 and another pin 1306 through the pin guide 1302 and into a medial condyle 174b of the femur 102. The pins 1306 may be pressed, pushed, forced, or driven into the femur 102 such that the pins 1306 are secured to the femur 102.

Advantageously, the pin guide 1302 aligns the pins 1306 with each other such that the pins 1306 are parallel when engaging the femur 102. In embodiments in which the pin guide 1302 is coupled to the superior plate 118 and pivots in accordance with the balance status, the parallel pins 1306 align with each other at an orientation relative to the superior plate 118 that matches the balance status.

FIG. 17B is a perspective view of two pins 1306 in one of the bones of FIG. 17A, according to one embodiment of the present disclosure. FIG. 17B illustrates a subsequent stage of one possible arthroplasty procedure according to one embodiment of the present disclosure. In this stage, an operator may remove the exemplary gap gauge 1300 by, for example by sliding the pin guide 1302 off the pins 1306 by moving the exemplary gap gauge 1300 in the anterior direction along the anterior-posterior axis 116. Alternatively, or in addition, an operator may drive the pins 1306 into the bone to create a mark, or pilot hole, in the bone. Next, the operator may remove the pins 1306 and the exemplary gap gauge 1300 and then replace the pins 1306 in the pilot holes made in the bone.

FIG. 17C is a perspective view of a cutting guide 1720 engaging the two pins 1306 in one of the bones of FIG. 17A, according to one embodiment of the present disclosure. FIG. 17C illustrates a subsequent stage of an arthroplasty procedure according to one embodiment of the present disclosure. In this stage, an operator may slide a cutting guide 1720 along the pins 1306 by coupling the pins 1306 with an alignment feature. In one example, an operator may pass the pins 1306 through an alignment feature, such as holes in the cutting guide 1720, and move the cutting guide 1720 in the posterior direction along the anterior-posterior axis 116 until the cutting guide 1720 contacts the bone, femur 102. In one embodiment, the pins 1306 are aligned with each other and positioned on the femur 102 in an orientation that represents the balance status of the joint 108. By coupling the cutting guide 1720 to the bone, femur 102, using the pins 1306, the balance status of the joint 108 is communicated to the cutting guide 1720.

FIG. 17D is a front perspective view of the cutting guide 1720 secured to one of the bones (e.g., a femur 102) of FIG. 17A, according to one embodiment of the present disclosure. In one embodiment, the cutting guide 1720 may include an alignment feature 1722, securing feature 1724, and guide feature 1726. FIG. 17D illustrates a subsequent stage to the stage illustrated in FIG. 17C. In one embodiment, the securing feature 1724 may include holes in a cutting guide 1720 and securing pins 1728.

Prior to the stage illustrated in FIG. 17D, an operator may pass pins, such as securing pins 1728, through holes of a securing feature 1724 of the cutting guide 1720. After securing pins 1728 securely connect the cutting guide 1720 to the bone, femur 102, an operator may remove the pins 1306 (which may also be referred to as alignment pins).

FIG. 17D illustrates the cutting guide 1720 secured to the bone using the securing pins 1728 of a securing feature 1724. In the illustrated embodiment, the cutting guide 1720 is secured to the bone such that performing a resection using the guide feature 1726 will resect the bone to counter for a balance status measured by the exemplary gap gauge 1300. FIG. 17D illustrates that a cut made in a slot of the guide feature 1726 on the lateral side will remove more bone and create a femur resected surface parallel to a tibia resected surface. Similarly, a cut made in a slot of the guide feature 1726 on the medial side may also remove more bone and create a femur resected surface parallel to a tibia resected surface.

Those of skill in the art appreciate that the embodiments of the present disclosure serve to measure a size of a gap or opening 106 in a knee joint 108, measure a balance status of a knee joint 108, and guide surgeon in making resection adjustments based on the balance status. Those of skill in the art appreciate that various embodiments of the present disclosure can be used to adjust the balance status such that the balance status reaches a desired balance status. A desired balance status may not be balanced, but may still be a desired balance status that can meet a patient's goals. Those of skill in the art also appreciate that various embodiments of the present disclosure can be used to adjust the balance status such that the balance status reaches a balanced status. In a balanced status, opposing resected surfaces of bones of a joint may be parallel to each other.

Those of skill in the art appreciate that there are various ways the components of the present disclosure can be arranged and/or embodied that can guide a surgeon in adjusting a balance status of the knee joint 108 to a desired balance status, such as a balanced status. Each of these ways, manners, arrangements, and embodiments are within the scope of this present disclosure and the included claims. A few examples of embodiments that can be used include those presented in connection with FIGS. 18A-18C, 19, 20, and 21. Of course, embodiments within the scope of this disclosure and claims can made that include aspects from each of the embodiments illustrated and described in relation to FIGS. 18A-18C, 19, 20, and 21. Such embodiments can be used for example to enable more fine levels of adjustments to a balance status to achieve a desired balance status.

Figure 18A:
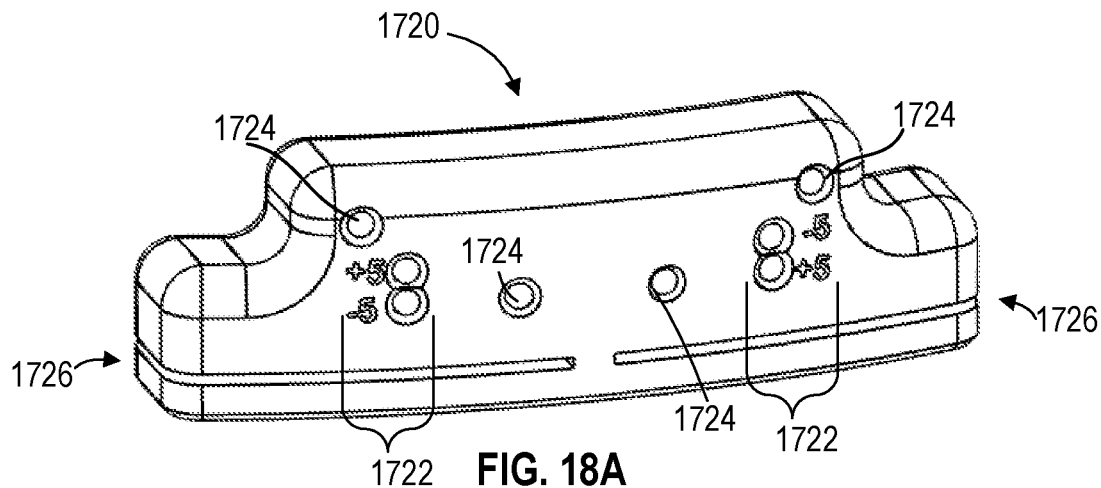
FIGS. 18A-18C are a front perspective view, font view, and a rear view of a cutting guide, according to one embodiment of the present disclosure.
Figure 18B:
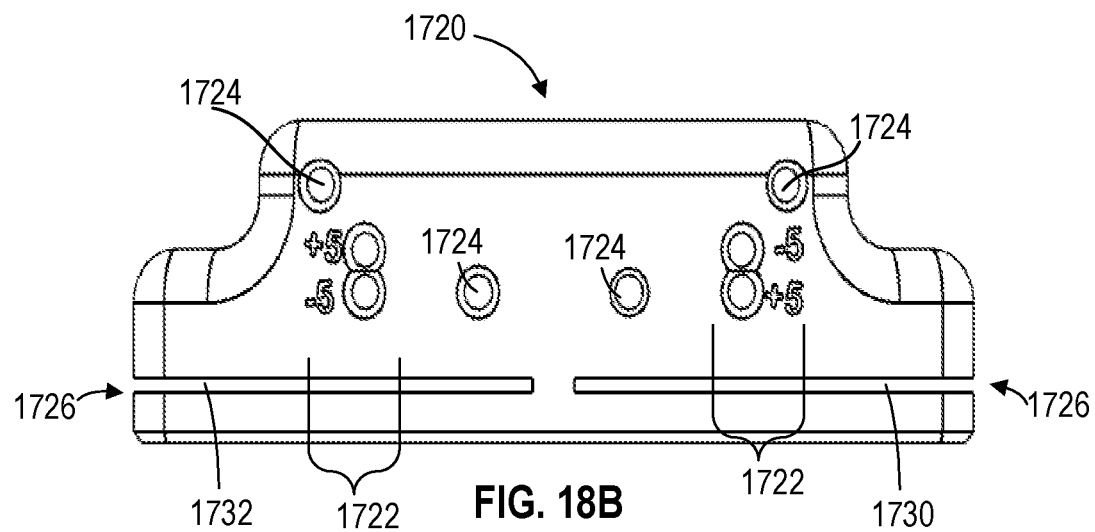
Figure 18C:
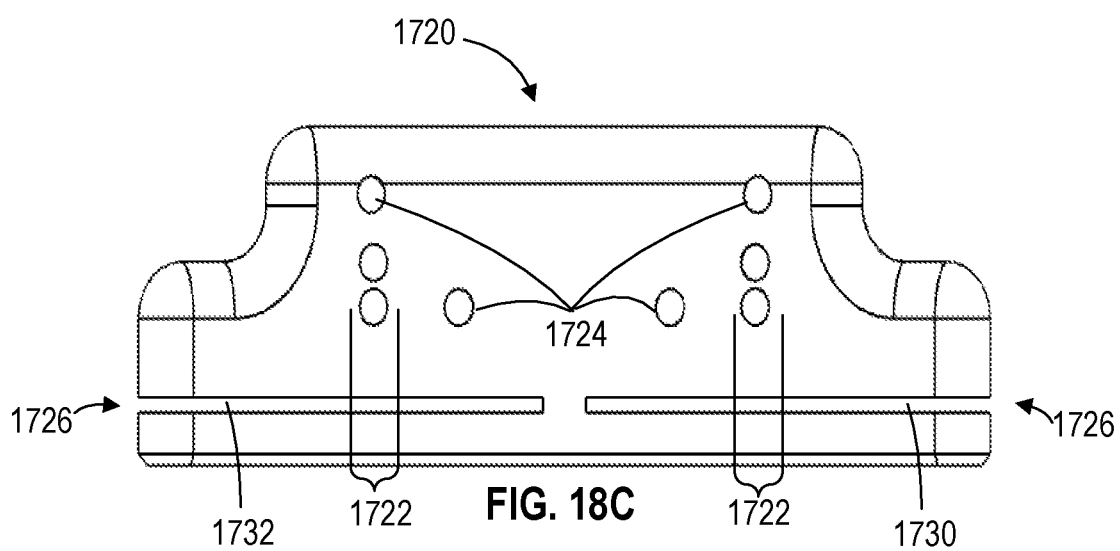

For example in one embodiment, an exemplary gap gauge 1300 can be used to determine a balance status and a cutting guide can be secured to a bone of the joint by use of a pin guide in such a way that resecting a bone using the cutting guide adjusts the balance status such that the joint has a balanced status (e.g., the resected surfaces are parallel after resecting using the cutting guide). FIGS. 18A-18C illustrate one example of such an embodiment. In this embodiment, one or more alignment features 1722 of a cutting guide 1720 cooperate with pins 1306 positioned by the pin guide 1302 to position the cutting guide 1720 on a bone to make a desired balance status adjustment.

FIGS. 18A-18C are a front perspective view, font view, and a rear view of a cutting guide 1720, according to one embodiment of the present disclosure. The cutting guide 1720 includes one or more alignment features 1722, securing features 1724, and one or more guide features 1726.

The alignment feature 1722, in one embodiment, can serve to position and align the cutting guide 1720 in relation to a bone such that performing a resection using the cutting guide 1720 creates a balanced status for the knee joint 108 and/or a desired balance status for the knee joint 108. In the illustrated embodiment, the alignment feature 1722 may include holes placed within the cutting guide 1720 that are configured to receive pins, such as pins 1306 positioned by a pin guide 1302. The holes can be positioned such that sliding the cutting guide 1720 on the pins 1306 enables a resection that counters, or adjusts, for a particular balance status (such as an imbalance status) reflected by a pin guide 1302 of the exemplary gap gauge 1300.

For example, where the pin guide 1302 is connected to a superior plate 118 such that the pin guide 1302 can pivot based on a balance status of a joint 108, the pins 1306 can be slid through corresponding holes in the cutting guide 1720 that will result in a compensating or adjusted resection. Referring to FIG. 18B, suppose a knee joint 108 is +5 degrees out of balance. The balance status can be read from a balance indicator 126. Said another way, the exemplary gap gauge 1300 may measure a nonparallel orientation of the superior plate 118 relative to an inferior plate 120.

An operator may place pins 1306 through the pin guide 1302 that positions the pins 1306 in the bone with the same +5-degree balance status. If the operator wants to counter or compensate for the +5-degree balance status, the operator can slide the cutting guide 1720 over the pins 1306 such that the pins 1306 are within the holes of the alignment features 1722 with a "+5" marking. Note the corresponding holes of the alignment features 1722 on each side of the cutting guide 1720 with a "+5" marking are not parallel with each other. They are offset at an angle such that resection with the cutting guide 1720 will result in resected surfaces of both bones of a joint 108 that are parallel.

In one embodiment, a cutting guide 1720 can include one or more alignment features 1722 that may be embodied in a plurality of sets of holes. Each set of holes may include two or more holes and each of the two or more holes can be configured to accept either a first pin 1306a or a second pin 1306b. Each set of holes can be configured to adjust for a different angular offset. A +5-degree marked hole on one side of the cutting guide 1720 and a +5-degree marked hole on another side of the cutting guide 1720 are one example of a set of holes that may embody one or more alignment feature 1722. A −5-degree marked hole on one side of the cutting guide 1720 and a −5-degree marked hole on another side of the cutting guide 1720 are one example of a set of holes that may embody one or more alignment feature 1722. Of course the alignment feature 1722 may include a number of holes on each side posited to compensate or adjust for a number of different angular offsets of the balance status.

The guide feature 1726 guides a cutter to resect a bone such as a femur 102 in the manner needed to make a desired adjustment. For example, the guide feature 1726 may be used to guide a planar cutting blade, an arcuate cutting blade, a drill or mill, a burr, and/or the like. The guide feature 1726 may guide a reciprocating planar blade, such as that of a surgical bone saw, that forms planar cuts. In one embodiment, the guide feature 1726 may take the form of a first slot 1730 and a second slot 1732, which may be positioned on each side of the cutting guide 1720. In alternative embodiments, a guide feature 1726 may be designed to guide a different type of cutter, such as a drill, mill, or side-cutting burr. In such embodiments, the guide feature may not be a slot, but may instead be a translatable or rotatable cutter retainer that guides translation and/or rotation of the cutter relative to the bone.

FIG. 18C illustrates a rear view of one embodiment of a cutting guide 1720. In certain embodiments, a rear surface of the cutting guide 1720 may be arcuate to more closely conform to a surface of a bone, such as a femur 102. The securing feature 1724 may be configured to accept securing pins 1728 at various angles of entry, including perpendicular.

In another example embodiment, an exemplary gap gauge 1300 can be used to determine a balance status and a cutting guide can be secured to a bone of the joint and an adjustment made using the cutting guide in such a way that resecting a bone using the cutting guide, as adjusted, adjusts the balance status such that the joint has a desired balanced status (e.g., the resected surfaces may be parallel or non-parallel after resecting using the cutting guide and the balance status is a desired balance status). In such an embodiment, an operator can make angular adjustments on the cutting guide rather than based on how the cutting guide couples to pins 1306 positioned by a pin guide 1302 of an exemplary gap gauge 1300.

Figure 19:
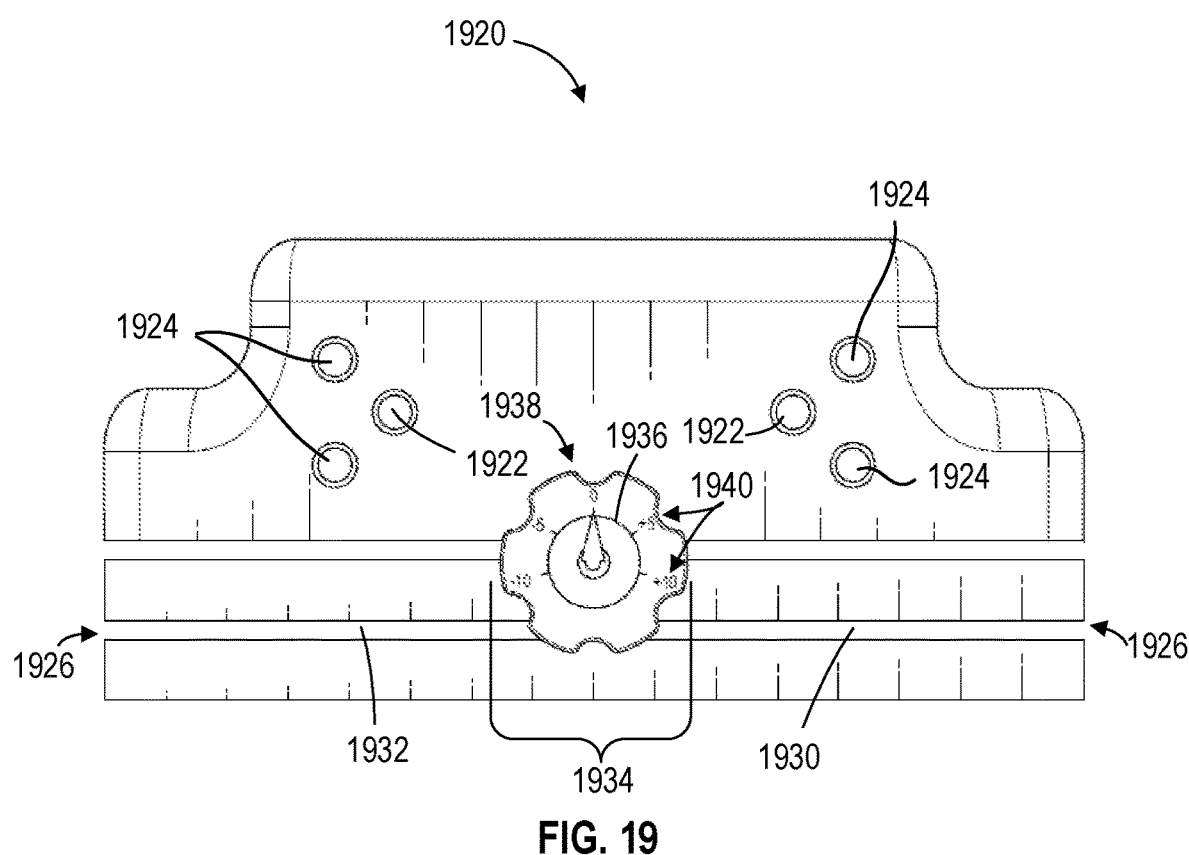
FIG. 19 is a front view of a cutting guide, according to one embodiment of the present disclosure.

FIG. 19 is a front view of a cutting guide 1920, according to one embodiment of the present disclosure. The cutting guide 1920 may be similar to other embodiments described herein. The cutting guide 1920 may include an alignment feature 1922 which may include a set of holes sized to accept pins 1306, one or more securing features 1924, and one or more guide features 1926.

The guide feature(s) 1926 may be embodied as a first slot 1930 and a second slot 1932 and guide motion of a cutter to resect a bone. The alignment feature(s) 1922 may include holes that are positioned and configured to accept a first pin 1306a and a second pin 1306b. The alignment feature(s) 1922 position the cutting guide on the bone for a resection. The securing feature(s) 1924 may include pins that pass through holes in the cutting guide 1920 and secure the cutting guide 1920 to the bone.

In certain embodiments, the cutting guide 1920 includes an adjustment feature 1934. The adjustment feature 1934 enables an operator to adjust for different angular offsets relative to a balance status or a nonparallel orientation. The adjustment feature 1934 may be configured to permit adjustment to a number of angular offsets within a range, such as between 0 and +20 degrees and between 0 and −20 degrees.

In one embodiment, the adjustment feature 1934 is configured to rotate one or more of the guide features 1926 relative to the alignment feature(s) 1922. For example, in one embodiment, the adjustment feature 1934 includes a knob 1936 that can be turned relative to the cutting guide 1920 to change an orientation of one or more guide features 1926 and set a different angular offset for guide features 1926 relative to the balance status and/or the nonparallel orientation.

The adjustment feature 1934 may include a face 1938 that includes one or more markings 1940 indicating different angular offsets. An operator can rotate the knob 1936 compensate, or counter, a balance status or nonparallel orientation. As the knob 1936 rotates the guide features 1926 may move in the direction of arrow A.

In another example embodiment, an exemplary gap gauge 1300 can be used to determine a balance status and a cutting guide can be secured to a bone of the joint and an adjustment made using a pin guide in such a way that resecting a bone using the cutting guide, as positioned by the adjusted pin guide, adjusts the balance status such that the joint has a desired balanced status (e.g., the resected surfaces may be parallel or non-parallel after resecting using the cutting guide and the balance status is a desired balance status). In such an embodiment, an operator can make angular adjustments on the pin guide rather than based on how the cutting guide couples to pins 1306 positioned by a pin guide 1302 or adjustments made on the cutting guide.

Figure 20:
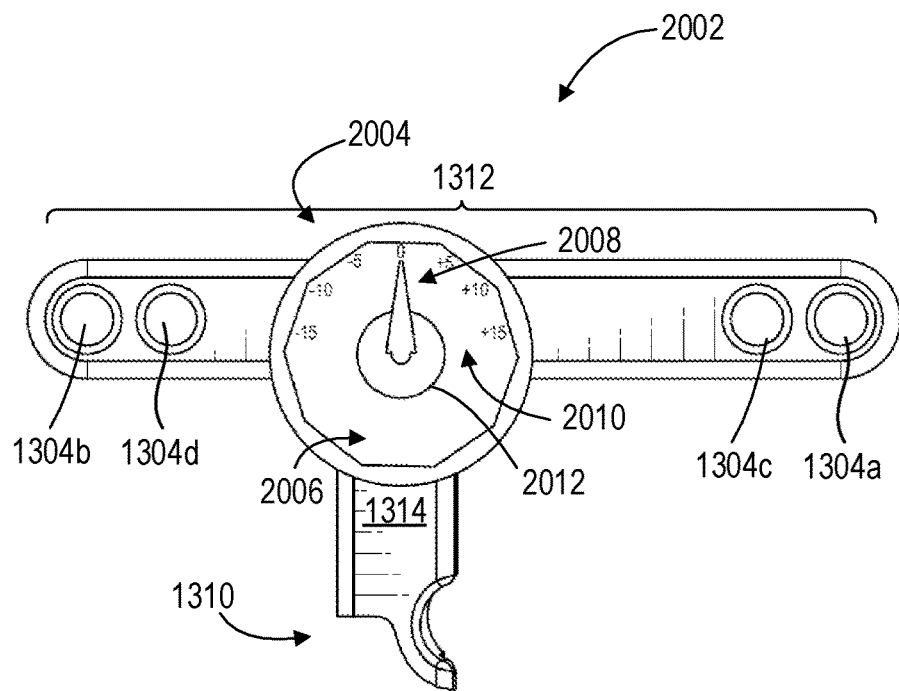
FIG. 20 is a front view of a pin guide, according to one embodiment of the present disclosure.

FIG. 20 is a front view of a pin guide 2002, according to one embodiment of the present disclosure. The pin guide 2002 may be connected to and/or removable coupled to a gap gauge such as exemplary gap gauge 1300. The pin guide 2002 may generally include a base 1310, arm 1312 with pin holes 1304 (e.g. first pin hole 1304*a* and/or second pin hole 1304*b*), and mast 1314 similar in structure, performance, and/or operation to like numbered components in other embodiments previously described. The first pin hole 1304*a* and second pin hole 1304*b* can be configured to guide insertion of a second pin 1306*b* parallel to a first pin 1306*a* into a bone.

In the illustrated embodiment, the pin guide 2002 may include an adjustment feature 2004. The adjustment feature 2004 may include a face 2006, a needle 2008, and a set of markings 2010. The adjustment feature 2004 may also include a knob 2012. The adjustment feature 2004 enables a user to rotate the knob 2012 to select a particular number of degrees away from balanced for a subsequent resection. This selected number of degrees may be opposite the number of degrees indicated on a balance indicator 126 of the exemplary gap gauge 1300. For example, if the balance indicator 126 indicates −5 degrees a user may rotate the knob 2012 to point to +5 degrees such that the −5 degrees of imbalance is countered or compensated for.

Rotating the knob 2012 may cause the arm 1312 to rotate such that the first pin hole 1304*a* and second pin hole 1304*b* rotate together to counter different angular offsets of the balance status. The knob 2012, or another structure may tighten the adjustment feature 2004 such that arm 1312 maintains the orientation after the knob 2012 is rotated to a desired setting, angular rotation. Once the pin guide 2002 is configured to compensate for a balance status, an operator may insert the first pin 1306*a* and second pin 1306*b* through corresponding first pin hole 1304*a* and second pin hole 1304*b*.

Next, as described above, the exemplary gap gauge 1300 may be slid off of the pins 1306 and a cutting guide may be slide over the pins 1306 and secured to a bone. In such an embodiment, the cutting guide may not include angular adjustment features and may instead include securing feature(s) and one or more guide features. In this manner, the pin guide 2002 may provide an angular adjustment for a resection.

In another example embodiment, an exemplary gap gauge 1300 can be used to determine a balance status and a cutting guide can be secured to a bone of the joint by use of a pin guide coupled to the exemplary gap gauge 1300 in such a way that resecting a bone using the cutting guide adjusts the balance status such that the joint has a balanced status (e.g., the resected surfaces are parallel after resecting using the cutting guide). In such an embodiment, an operator can secure a cutting guide a bone by use of a pin guide coupled to the exemplary gap gauge 1300 in such a way that using a cutting guide (that does not include adjustment features) adjusts the balance status such that the joint has a balanced status. Angular adjustments using the pin guide or cutting guide are not needed.

Figure 21:
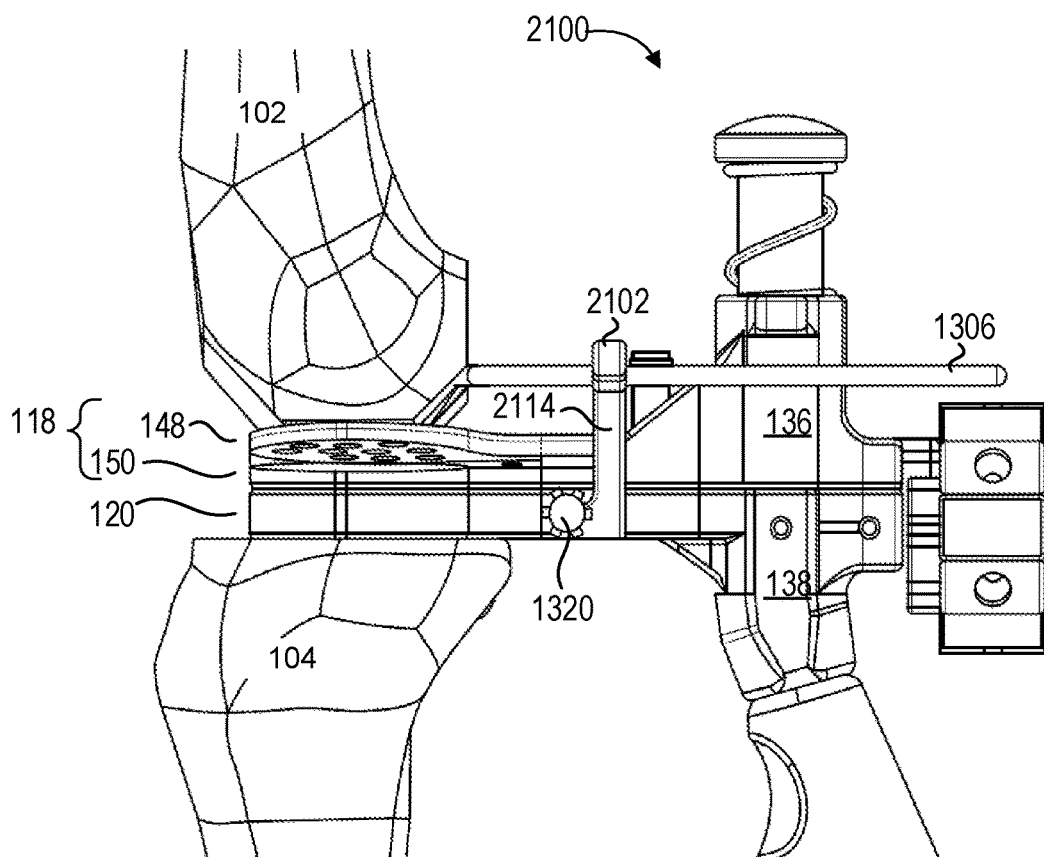
FIG. 21 is a side perspective view of a pin guide, according to one embodiment of the present disclosure.

FIG. 21 is a side perspective view of a pin guide 2102, according to one embodiment of the present disclosure within an embodiment of an exemplary gap gauge 2100. In one embodiment, the exemplary gap gauge 2100 may generally include a first plate and a second plate. In the illustrated embodiment, the first plate may be an inferior plate 120 and the second plate may be a superior plate 118. The superior plate 118 may include a pivot plate 148 and a support plate 150. The first plate 120 can be positioned in contact with a first bone, such as a tibia 104 and the second plate 118 can be positioned in contact with a second bone, such as a femur 102. In one embodiment, the first plate and the second plate are sized for insertion between a first bone that is a tibia and a second bone that is a femur. The superior plate 118, inferior plate 120, pivot plate 148, and support plate 150 may be similar in structure, performance, and/or operation to like numbered components in other embodiments previously described.

The exemplary gap gauge 2100 may also generally include a separator 122, a separation indicator 124, a balance indicator 126, a handle 134, a superior body 136, and an inferior body 138 similar in structure, performance, and/or operation to like numbered components in other embodiments previously described.

In one embodiment, the exemplary gap gauge 2100 includes a pin guide 2102 similar in structure, performance, and/or operation to like numbered components in the embodiment illustrated in FIG. 14A, with the following exceptions. In the illustrated embodiment, the pin guide 2102 may include a mast 2114 that is long enough to connect or couple the pin guide 2102 to the inferior plate 120, rather than a superior plate 118, pivot plate 148, or support plate 150. In another embodiment, the pin guide 2102 may include a base configured to connect or couple the pin guide 2102 to the support plate 150. The methods or operation and use described herein can be used with the exemplary gap gauge 2100 to complete an arthroplasty procedure.

In the illustrated embodiment, the pin guide 2102 extends in the direction of a second bone, such as the femur 102. The pin guide 2102 guides insertion of a first pin 1306*a* and a second pin 1306*b* into the second bone, the femur 102. The pin guide 2102 aligns the first pin 1306*a* and second pin 1306*b* with each other at an angle relative to the second plate (superior plate 118) that counters a balance status between the first plate (inferior plate 120) and the second plate (superior plate 118). The pin guide 2102 may be couplable to the exemplary gap gauge 2100 by way of a set screw 1320 similar to that described above.

When the exemplary gap gauge 2100 is in use in a knee joint 108, the inferior plate 120 contacts the tibia 104 and the superior plate 118 contacts the femur 102. An operator can then review and adjust for a gap and a balance status. The balance status can be measured, at least in part, because the pivot plate 148 is configured to pivot relative to the support plate 150 and/or inferior plate 120. Because the pin guide 2102 connects, or is connectable, to a non-pivoting plate (such as the inferior plate 120 or support plate 150) and the arm 1312 is perpendicular to the mast 2114 and the mast 2114 is perpendicular to the non-pivoting plate, pins 1306 inserted into parallel pin holes 1304 of the pin guide 2102 are parallel to the non-pivoting plate. Consequently, a cutting guide guided by the pins 1306 and secured to the femur 102 and having a guide feature parallel to the two aligned pins 1306 will guide a resection that counters the balance status between the first plate (inferior plate 120) and the second plate (superior plate 118). In this manner, no further angular adjustment may be needed from the pin guide or the cutting guide.

Figure 22:
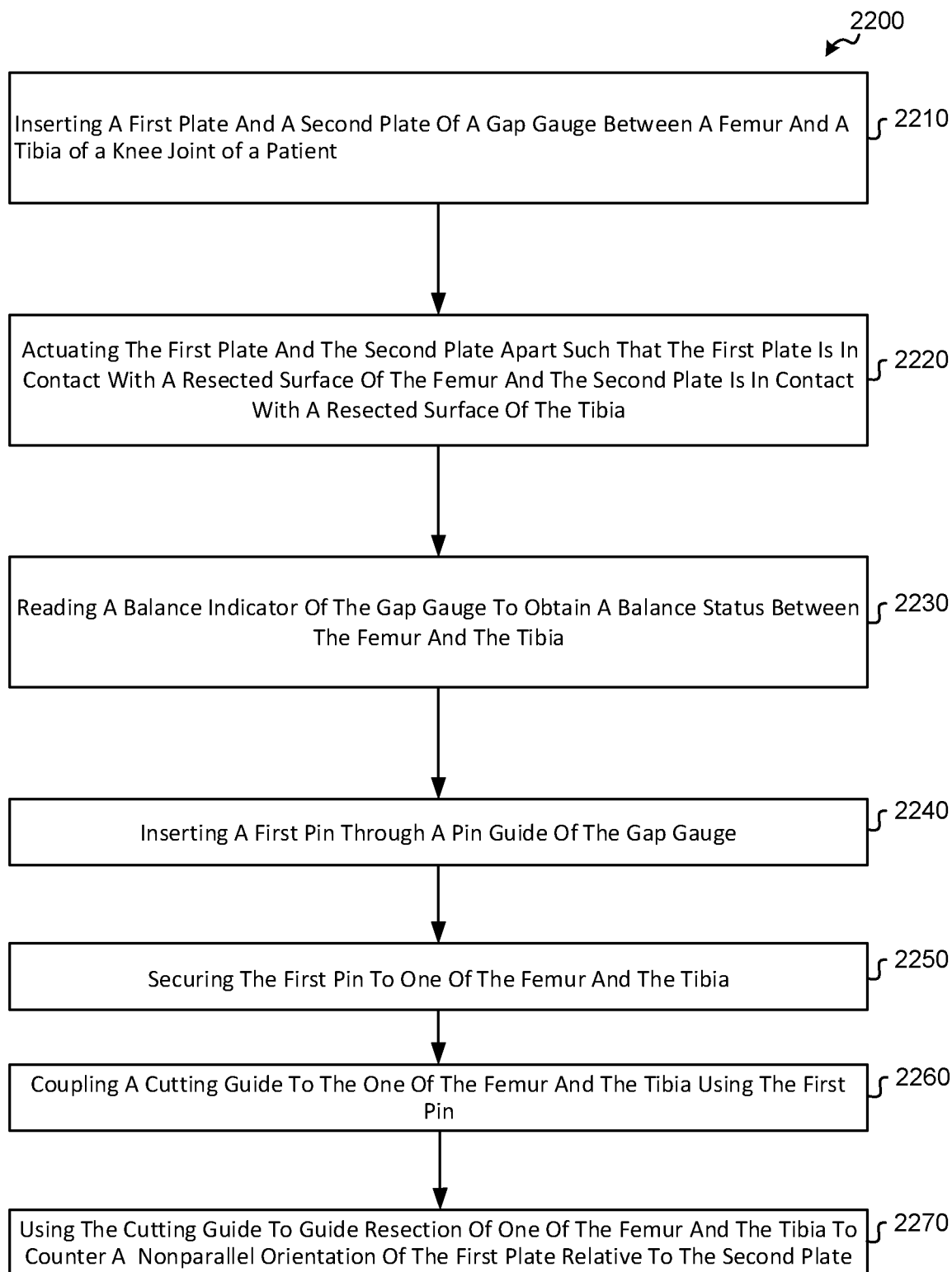
FIG. 22 illustrates a flowchart for measuring and correcting imbalance for an arthroplasty procedure on a femur and a tibia of a patient, according to one embodiment of the present disclosure.

FIG. 22 illustrates a flowchart for a method 2200 for measuring and adjusting imbalance for an arthroplasty procedure on a femur and a tibia of a patient, according to one embodiment of the present disclosure. In general, the method 1200 may include the use of gap gauge that includes both a balance indicator 126 and a pin guide. In certain embodiments, the method 1200 may also include a cutting guide as part of an assembly.

The method 2200 may begin with a step 2210 in which a first plate (e.g., inferior plate 120) and a second plate (e.g., superior plate 118) of a gap gauge may be inserted between a femur and a tibia. In certain embodiments, the gap gauge may be positioned such that a pivot axis of a hinge may be aligned with an anterior-posterior axis of a patient.

Once the gap gauge is positioned, the method 2200 may proceed to step 2220 in which the first plate and second plate are actuated apart such that the first plate contacts a resected surface of the femur and the second plate contacts a resected surface of the tibia.

Once the first plate and second plate have been actuated apart, the method 2200 may proceed to step 2230 in which a balance indicator of the gap gauge is read to obtain a balance status between the femur and the tibia.

A surgeon may use the balance status to determine whether to do further resection of the femur 102 and/or tibia 104, and/or where to position a cutting guide for the resection.

Once a balance status has been read, the method 2200 may proceed to step 2240 in which a first pin is inserted through a pin guide of the gap gauge. The method 2200 may then proceed to step 2250 in which the first pin is secured to one of the femur and the tibia. Next the method 2200 may then proceed to step 2260 in which a cutting guide is coupled to the one of the femur and the tibia using the first pin. Once the cutting guide is coupled to the one of the femur and the tibia, the method 2200 may then proceed to step 2270 in which the cutting guide is used to guide resection of one of the femur and the tibia to counter a nonparallel orientation of the first plate relative to the second plate.

After performing the resection, the method 2200 may end with the two bones resected to a desired balance status.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. A system for facilitating an arthroplasty procedure on a first bone and a second bone of a patient, the system comprising:
    a gap gauge comprising;
        a first plate positionable in contact with the first bone;
        a second plate positionable in contact with the second bone, wherein the second plate is displaced from the first plate by a displacement;
        a balance indicator configured to indicate a balance status between the first plate and the second plate; and
        a pin guide configured to couple to one of the second plate and the first plate, the pin guide comprising a first pin hole configured to guide insertion of a first pin into the second bone;
    wherein the pin guide comprises:
        a second pin hole configured to guide insertion of a second pin parallel to the first pin into the second bone; and
        an adjustment feature configured to rotate the first pin hole and the second pin hole together to counter different angular offsets of the balance status.

2. The system of claim 1, wherein the pin guide further comprises an attachment feature configured to removably couple the pin guide to the second plate such that the pin guide guides insertion of the first pin into the second bone according to the balance status between the first plate and the second plate.

3. The system of claim 1, wherein the pin guide further comprises an attachment feature configured to removably couple the pin guide to the second plate such that the pin guide guides insertion of the first pin into the first bone according to the balance status between the first plate and the second plate.

4. The system of claim 1, wherein:
    the pin guide comprises a second pin hole configured to guide insertion of a second pin into the second bone; and
    the pin guide is coupled to the first plate and extends from the first plate such that the pin guide guides insertion of the first pin and the second pin into the second bone such that the first pin and the second pin align at an angle relative to the second plate that counters the balance status between the first plate and the second plate.

5. The system of claim 1, wherein the first pin hole guides insertion of the first pin into one of a medial condyle and a lateral condyle of the second bone and the pin guide comprises a second pin hole configured to guide insertion of a second pin into the other one of the medial condyle and the lateral condyle of the second bone.

6. The system of claim 1, wherein the pin guide comprises:
a base configured to connect to the second plate;
an arm comprising the first pin hole; and
a mast extending from the base, the mast connecting the arm and the base.

7. The system of claim 6, wherein the arm comprises a second pin hole, the first pin hole and the second pin hole each positioned in the arm on one of a medial side and a lateral side of a knee when the gap gauge is in place relative to the knee.

8. The system of claim 1, wherein the pin guide comprises a second pin hole configured to guide insertion of a second pin into the second bone such that the first pin and the second pin align with each other at an orientation relative to the second plate that matches the balance status; and
the system further comprises a cutting guide configured to be coupled to the second bone by way of the first pin and the second pin such that the balance status is communicated to the cutting guide.

9. The system of claim 8, wherein the cutting guide comprises an alignment feature comprising a plurality of sets of holes, each member of a set of holes configured to accept one of the first pin and the second pin, each set of holes configured to adjust for a different angular offset for the balance status.

10. The system of claim 8, wherein the cutting guide comprises:
a guide feature configured to guide motion of a cutter to resect a bone; and
an alignment feature configured to accept the first pin and the second pin and position the cutting guide on the bone.

11. The system of claim 1, wherein the first plate and the second plate are sized for insertion between the first bone that comprises a tibia and the second bone that comprises a femur.

12. A system for facilitating an arthroplasty procedure on a knee joint comprising a femur and a tibia of a patient, the system comprising:
a gap gauge comprising;
a first plate positionable in contact with a first bone comprising one of the femur and the tibia;
a second plate positionable in contact with a second bone comprising the other of the femur and the tibia, wherein the second plate is displaced from the first plate by a displacement;
a balance indicator configured to indicate a nonparallel orientation between the first plate and the second plate;
a pin guide configured to couple to one of the second plate and the first plate, the pin guide comprising a first pin hole configured to guide insertion of a first pin into the second bone; and
a cutting guide attachable to one of the tibia and the femur via the first pin, wherein the cutting guide is configured to guide resection of the other one of the tibia and the femur that counters the nonparallel orientation.

13. The system of claim 12, wherein:
the pin guide comprises a second pin hole configured to guide insertion of a second pin into the second bone; and
the pin guide is coupled to the first plate and extends from the first plate such that the pin guide guides insertion of the first pin and the second pin into the second bone such that the first pin and the second pin align at an angle relative to the second plate that counters the nonparallel orientation between the first plate and the second plate.

14. The system of claim 12, wherein:
the pin guide comprises a second pin hole configured to guide insertion of a second pin into the second bone such that the first pin and the second pin align with each other at an orientation relative to the second plate that matches the nonparallel orientation;
the cutting guide is configured to be coupled to the second bone by way of the first pin and the second pin such that the nonparallel orientation is communicated to the cutting guide; and
the cutting guide comprises an alignment feature comprising a plurality of sets of holes, each member of a set of holes configured to accept one of the first pin and the second pin, each set of holes configured to adjust for a different angular offset for the nonparallel orientation.

15. The system of claim 12, wherein:
the pin guide comprises a second pin hole configured to guide insertion of a second pin into the second bone such that the first pin and the second pin align with each other at an orientation relative to the second plate that matches the nonparallel orientation;
the system further comprises a cutting guide configured to be coupled to the second bone by way of the first pin and the second pin such that the nonparallel orientation is communicated to the cutting guide; and
the cutting guide comprises:
a guide feature configured to guide motion of a cutter to resect a bone;
an alignment feature configured to accept the first pin and the second pin and position the cutting guide on the bone; and
an adjustment feature configured to rotate the guide feature relative to the alignment feature to adjust for different angular offsets from the nonparallel orientation.

16. A system for facilitating an arthroplasty procedure on a knee joint comprising a femur and a tibia of a patient, the system comprising:
a gap gauge comprising;
a first plate positionable in contact with a first bone comprising one of the femur and the tibia;
a second plate positionable in contact with a second bone comprising the other of the femur and the tibia, wherein the second plate is displaced from the first plate by a displacement;
a balance indicator configured to indicate a nonparallel orientation between the first plate and the second plate; and
a cutting guide attachable to one of the tibia and the femur such that the cutting guide guides resection of one of the tibia and the femur to counter the nonparallel orientation.

17. The system of claim 16, further comprising a pin guide comprising:
a first pin hole configured to guide insertion of a first pin into the second bone; and a second pin hole configured to guide insertion of a second pin into the second bone;
wherein the pin guide is coupled to the first plate and extends from the first plate such that the pin guide guides insertion of the first pin and the second pin into the second bone such that the first pin and the second pin align at an angle relative to the second plate that counters the nonparallel orientation between the first plate and the second plate.

18. The system of claim 16, further comprising a pin guide comprising:
a first pin hole configured to guide insertion of a first pin into the second bone;
a second pin hole configured to guide insertion of a second pin parallel to the first pin into the second bone; and
an adjustment feature configured to rotate the first pin hole and the second pin hole together to counter different angular offsets of the nonparallel orientation.

19. The system of claim 16, further comprising:
a pin guide comprising:
 a first pin hole configured to guide insertion of a first pin into the second bone; and
 a second pin hole configured to guide insertion of a second pin into the second bone such that the first pin and the second pin align with each other at an orientation relative to the second plate that matches the nonparallel orientation; and
a cutting guide configured to be coupled to the second bone by way of the first pin and the second pin such that the nonparallel orientation is communicated to the cutting guide;
wherein the cutting guide comprises an alignment feature comprising a plurality of sets of holes, each member of a set of holes configured to accept one of the first pin and the second pin, each set of holes configured to adjust for a different angular offset for the nonparallel orientation.

20. The system of claim 16, further comprising:
a pin guide comprising:
 a first pin hole configured to guide insertion of a first pin into the second bone; and
 a second pin hole configured to guide insertion of a second pin into the second bone such that the first pin and the second pin align with each other at an orientation relative to the second plate that matches the nonparallel orientation; and
a cutting guide configured to be coupled to the second bone by way of the first pin and the second pin such that the nonparallel orientation is communicated to the cutting guide;
wherein the cutting guide comprises:
 a guide feature configured to guide motion of a cutter to resect a bone;
 an alignment feature configured to accept the first pin and the second pin and position the cutting guide on the bone; and
 an adjustment feature configured to rotate the guide feature relative to the alignment feature to adjust for different angular offsets from the nonparallel orientation.

* * * * *